(12) United States Patent
Gustafsson et al.

(10) Patent No.: US 6,280,999 B1
(45) Date of Patent: Aug. 28, 2001

(54) SORANGIUM POLYKETIDE SYNTHASES AND ENCODING DNA THEREFOR

(75) Inventors: Claes Gustafsson, Belmont; Mary C. Betlach, San Francisco; Gary Ashley, Alameda; Bryan Julien, Oakland; Rainer Ziermann, San Mateo, all of CA (US)

(73) Assignee: Kosan Bioscience, Hayward, CA (US)

( * ) Notice: Subject to any disclaimer, the term of this patent is extended or adjusted under 35 U.S.C. 154(b) by 0 days.

(21) Appl. No.: 09/144,085

(22) Filed: Aug. 31, 1998

Related U.S. Application Data

(63) Continuation-in-part of application No. 09/010,809, filed on Jan. 22, 1998, now Pat. No. 6,090,601.

(51) Int. Cl.[7] ............... C12N 1/20; C12N 15/00; C12N 5/00; C12N 9/00; C07H 21/04
(52) U.S. Cl. ............. 435/252.3; 435/183; 435/320.1; 435/325; 536/23.2
(58) Field of Search ............... 435/320.1, 252.3, 435/325, 183; 536/23.2

(56) References Cited

U.S. PATENT DOCUMENTS

| | | | |
|---|---|---|---|
| 4,874,748 | 10/1989 | Katz et al. | 514/29 |
| 5,063,155 | 11/1991 | Cox et al. | 435/76 |
| 5,098,837 | 3/1992 | Beckmann et al. | 435/172.3 |
| 5,116,756 | 5/1992 | Dumont et al. | 435/253.5 |
| 5,149,639 | 9/1992 | Katz et al. | 435/76 |
| 5,672,491 | 9/1997 | Khosla et al. | 435/148 |
| 5,712,146 | 1/1998 | Khosla et al. | 435/252.35 |

FOREIGN PATENT DOCUMENTS

| | | |
|---|---|---|
| WO 93/13663 | 7/1993 | (WO) . |
| WO 95/08548 | 3/1995 | (WO) . |
| WO 96/40968 | 12/1996 | (WO) . |
| WO 97/02358 | 1/1997 | (WO) . |
| WO 98/27203 | 6/1998 | (WO) . |

OTHER PUBLICATIONS

Fu et al, *Biochemistry* 33:9321–9326 (1994).
McDaniel et al., *Science* 262:1546–1550 (1993).
Motamedi et al., "Structural organization of a multifunctional polyketide synthase involved in the biosynthesis of the macrolide immunosuppressant FK506", *Eur. J. Biochem.*, 244, pp. 74–80.
Rohr, *Angew. Chem. Int. Ed. Engl.* 34(8):881–888 (1995).
Schwecke et al., "The bioynthetic gene cluster for the polyketide immunosuppressant rapamycin", *Proc. Nat'l Acad. Sci. USA* 92 (Aug. 1995), pp. 7839–7843.
Cortes et al., Nature, 348, 176–178, Nov. 1990.*

\* cited by examiner

*Primary Examiner*—Ponnathapu Achutamurthy
*Assistant Examiner*—Maryam Monshipouri
(74) *Attorney, Agent, or Firm*—Kevin R. Kaster; Carolyn A. Favorito; Kate H. Murashige

(57) ABSTRACT

Novel Sorangium polyketide synthases, and domains thereof, and polynucleotides encoding therefor. Additionally, chimeric polyketide synthases that include domains, or subsets of domains, patterned on said novel polyketide synthases. Methods to prepare polyketide combinatorial libraries are described, as are recombinant host cells in which polyketides are produced.

8 Claims, 21 Drawing Sheets

```
GATCCCCAGCAGCGGCTGGTGCTGGAGACGGCGTGGGAGGCATTGGAGCCGTGCCGGCCGTGCGCCCGTCGGCGCTGAGCGG
GAGCGCCACCGGAGTGTATCTCCGGGTCGATGGGCTCGGACTACGGTGCTCTTCATACCGGCGGGCTGGAAGCGCTGGACG
GGTACCGGGGCACCGGGAGCGCGGCGAGCGTGCCTCTCAGGCCGTGTGGCCTACGTGCTCGGGTTGCAGGGCCCAGCGATC
ACGGTGGACACGGCGTGCTCGTCGTCGCTGGTGTCGCTGCACCTCGCGTGCACGGCGTTGCGTCAGGGTGAATGCGACCT
GGCGCTGGCCGGCGGGGTGACGGTGATGAGCACCCCGCGTTGTTCGTGGAGTTCAGCCGGCTCAAGGGGATGGCCCGCG
ACGGCCGCTGCAAGAGCTTCTCTGCGCGAGCTGACGGCGTCACCTGGTCCGAGGGGTGCGGGATGCTGGTGCTGAAGCGG
CTGTCGGACGCGCGGCGCGACGGTGACCGTGTGCTTGCGGTGGTCCGCGGGTCAGCGGTGAACCAGGACGGTCGCAGCCA
GGGCCTGACGGCGCCCGAACGGTCCCGCGCAGCAGCGGGTGGTCCAGCGGGCGCTCTCGTCGTGCGGGCTGTCGCCCGAGG
ACATCGACGCGGTGGAGGCGCACGGGACAGGCACGAGCCTCGGAGATCCGATCGAGGCGGGAGCGCTCGCGGAGGTGTTC
GGGCCTGGGCCGCAAGGCCGAGCGACCGCTGTACCTGGGCTCGTCGAAGTCCAACCTGGGGCATACGGGGCCTGCGGCGGG
TGTAGTCGGTGTGCTCAAGATGGTGCTGTCGATGCAGCACGAGGTGCTGCCGCGGACGCTGCACGCGGAGCAGCCGAGCC
CGCACATTGGGTGGGAGGGAGCGGGCTGTCGT GCTGCAAGAGGCGCGTCCGTGGCGGCGCAACGGCCGGGCGCGGCGC
GCGGGCGTGTCGTCGTTCGGGATCAGCGGGACGAACGCGCATGTCATCCTCGAAGAGGCGCCGGTGGAGGCGGCGCGCGA
GCCGGTGGAGGCGGTGCGCGAGCCGTTGGCGACGGAGGGTGTTGCGATGCCGCTGTTGCTGTCGGGGCGAGACGAGGCCT
CGGTGGCGGCGCAGGCGGAGCGCTGGGCGAAGTGGCTGGAAGAGCACGCGGAGGTGGGGTGGTCGGACGTGGTGAGGACA
GCGGCGCTGCACCGGACGCACTTCGCCTCACGCGCATCCGTGCTTGCGGCGAGCGTGTCGGAGGCGGAGGAGGCGCTGCCG
GGCGCTGTCGCAGGGTCGCCGGCCACCGGGCGGTGTCGGCGGGCACGGCGCGTGCGCGAGGCAAGGTGGTGTTCGTGTTCC
CCGGCCAAGGGAGCCAGTGGCCCGGGGATGGGCCGGGCGCTGCTGGAGCAGAGCGCGGCGTTCGCGGAGGCGGTGCAGGCC
TGCGATGAGGCGCTGCGGCCGTGGACGGGCTGGTCTGTGCTGTCGGTGCTGCGCGGCGAGGCGGGTGAGGCAGGTGAGGA
GCAGCCGTCGCTGGAGCGGGTGGACGTGGTGCAGCCCGCGCTGTTCGCGATGTGCGTGGGTCTGGCCGCGGCGTGGAGGT
CGCTGGGGCTGGAGCCTGCGGCGGTGGTGGGCCACAGCCAGGGCGAGGTGTCGGCGGCGGTGGTGCGGGGCGCTGTCG
CTTGCGGAGGGAGCGCGGGTAGTGGCGCTGCCGCAGCCAGGCGGTGCGGCAGCGGTCGGGGATGGGGCCGATGATGCTGGT
CGAGCGGCCGGTGTCGGAGGTGCAGGAGCGCATCGCGCCGTACGGGGAGGCGCTTGCGATAGCGGCGGTGAACACGTCGA
GCTCGACGGTGGTGTCGGGTGACGTGGAGGCGGTGGACGGGCTGATGGGGGAGCTGACGGCAGAAGGTGTGTTCTGCCGG
AAGGTGAACGTCGACTACGCGTCGCACAGCGCGCACATGGATGCGCTGCTGCCCGAGCTAGGAGCGAAGCTGTCGTCGCT
CAGGCCGAAGGCCGACGCAGCTGCCGTTTTACTCGACGGTGGCAGGAGAGGTGTCGCGGAGGCGAGGCGCTGGACGGCGAGT
ACTGGTGCCGCAACCTTCGGCAGACGGTGCGCCTGGACCGAGCGCTGTCGAAGCTGCTGGAGGACGGGCACGGTGTGTTC
GTGGAGGTGAGCGCGCACCCGGTGCTGGCGATGCCGCTGACGACGGCGTGCGGGGAGGCGCAGGGGTGGTGGTGGGGAG
CCTGCAGCGCGACGAAGGTGGGTTGTCGCAGCTGTACAGGACGCTGGGGCAGCTGCACGTGCAGGGGCACGAGGTGGACT
GGGCACGGGTGCTGCCGGGCCATGGCGGTCGTGCCCTGGAGCTGCCGACGTACGCATTCCAGCGGCAGCGCTACTGGCTG
GAGGCGCCGAGGGCGCGCGGTGACGTGAGCTCGGCGGGGCTGAAGGCGGCCGCCCATCCCGCTGCTCGGCGCCGCGACCAA
GCTCGCCGACGGCCAGGGGCACCTGTTCACAGGGAGGCTGTCGCCTGGCGGAGCATGCGTGGCTTCGGGATCATGGTGTGT
TTGGCCAGGTGGTGTTTCCGGGCACGGGCATGCTGGAGGTTGCGCTGGCGGCTGGGCGCGCGGTGGGCAGCCGGTCGCTG
TCGGAGCTCACGCTCGCCCGAGCCGCTGGTGCTGGCCGAGGACGGCGCGGCGCGGCTGCAGGTGATGATCGGAGCGCCAGA
TGCCGGCGGGCCGGCGCGAGGTGGGGCTGTACAGCCAGCCTGAGCATGCCCCGGAGGACGCGCCGTGGGTGCAGCACGCGA
CGGGAGTGTTGACGGACGAGCTCCCCGGCATCCCTGACGAGCTCGACGAGCTGTCGATGTGGCCTGTGCCGGGGCGCCGAG
GAGGTGGACCTGTCCGGGTTTTACGAGCGGCTGCCGTGAGCCGGGCTCCACTACGGTCCGACGTTCCAGGGCCTCGTGGA
GCTGTCGCGCCAAGGCACCAGGCTTTATGGCCGGGTGGTGCTGCCAGGAACCGAGAAGGACAGGGCGGAGGCGTATGGCT
TGCATCCCGTCCTGATGGATGCAGCACTGCAGGTGCTTGGCGCAGCCGGCGAGGGGCATTGGGAGGCGGATGCCGTTGTTT
ATGCCCTTCTCCTGGGCAGACGCCGCAACGCATGCCACGGGTCCGAGCGAGCTTCGGGTGCGCGTGGAGCTCGAAGAGAC
AGACGGCTCCACGCAGGCAACGGCATCTCTGTGCGCTGCAGATGCCGCAGGCCAGCCGGTGGCGAGCGTCGGTGCTTTGC
GTTTGCGCCCGTGACGGCCGAGCAATTGAGGGCGGTCACCCGCACCGATGAGCAGCACCTGTACCGGGTGAGCTTCCAG
CCCGTGAGCCTCGCGCAAGCCCCCTGGAGGCGGGCTCGCTGGTGGTCCTCGCTGCAGCGGAGGGACGAGGGCAGCTGGC
CGACACCCTGGGGGCGGAGGCGATTGCCGATCTCGATGCATTGCGCGCTTGGATCGAGCGGGGCGCGCCAACGCCTGTGC
GGGTGGTGATCGACACGAACGCTGCCAGCTCACCGCGCTCGGACGTGGCGGGGTCGTCGCACGAGGCGACGAGGCAGGCG
CTGTCGCTGCTGCAAGCGTGGTTGTCGGAGCCGCGGCTCGACGCTGTCGAGCTGGTGTGGGTGACGCGGGGCGCGGTCAG
CGCAGCTCCGGACGACGCCGTCGAGGACCTGGCGCACGGGCCGCTGTGGGGCTTATTCGCACGGCGCGCACCGAGCACC
CCGAGCGCCGGCTGCGCTTGATCGATGTGGGGACCGAGCCCGTGGACGCTGGGCTGCTGGCCGCGGGCGCTGCCGACGGCC
GCGGAGCCGGAGCTTGCGCTGCGCGGGGGCGCGGTGCTGGCCGCGCGGCTGGTGCCGCGTACAGGCGGCAGCGGAAGAGCT
CACCCGAGCCCGCGGGCTGGACCCTGCGGGCACCGTGCTGGTGACCGGAGCCGTGGGCGGTCTGGGGCAGGCGGTGACAC
GCCATCTGGTGCCGCGCGCACGGGGTGAGGCACCTTGTGCTGACGTCGCGCCGGGGCTGGAGGCGCCCGGGGCCCGCGAG
CTTGTGCAATCGCTCGAGGAGCTCGGCGCCGAGACCGTGTCGATGGTGGCGTGCCGACGTGTCGAAGCGGGAGGAGATCGC
GCGCGTGCTGGCCCGGCATCGACGCGGCGCGCCCGCTGAGCGCGGTGCTGCACCTGGCTGGCGTGGTCCATGATGGCGTGA
TTCAGACGCAGACGGCCGAGCGCCTCGGCGTGGGTGCTGGCGCCGAAGGTGGACGGGCGCTGCACCTGCACCGAGCTGACG
```

FIG.1A

```
CGGGAGCTGGATCTCGCGGCGTTCGTGCTGTTCTCGTCGGCGGCCGGTACGTTGGGCATGGCGGGCCAGGGCAATTACGC
GGCCGCGAATACGTTCCTCGACGCGTTCGCGGCGCACCGCCGCGGCCGCGGGCTCGCGGCGACGAGCCTCGCCTGGGGTG
TCTGGACACCGGCCGGTGGTGGCATGGCGGCACAGCTGGGGGCCGCGGAGCTGGCACGGTTCAGTCGCTACGGAGTCGTG
TCGATGTCCGTGGAAGAGGGGCTTTCGCTGCTGGACGCCGCGCTGTCACGCCCTGAAGCGAGCCTGGTCCCTATGCACCT
GGATCTCGCGCAGCTGCAGCGTGGGCTGGAGGCCAACGGCGAGCTGCCGGCGCTGTTTCGTGCGCTGTTGCGCCCCAGCT
TGCGCAAGGCGTCCACGGCGACGAGGCGAGACGCCTCGGCGCTGCGCGGGCGCCTCTCGGCGCTGCCGGAGGCGGAGCGG
CTGAATGCGCCTCATCGAGCTGGTGCGGGGCGAGGTCGCCGCGGTGCTCGGGCTCCAGCGCAGCGAGGCCGTGGGGCGGA
GCAGGTGCTGAAGGGCCTCGGGCTCGACTCGCTGATGGCGGTGGAGCTGCGCAACCGCCTCGCCGCCCGGACCGAGACGT
CCTTGCCGGCGACGCTGGTCTTCGACTACCCGACGCCGCGGGCCATCGCGGAGTTGCTCCTGAAGCTGGCCTTTTCGGGA
CCGCAGGTGATGGAGCCCGCAGGGGGGTGCGTCGTCATGCGGGGAAAGACGAGGCGGTGGCCGATCGTATCGATGGCCGTG
CCCGCTGCCGGGAGGCGTCGAGACGCCCGAAGACTACTGGCGTCTCTTGGCCGAGGGGAAAGACGTGATCGAGGGCCTCC
CTGCGCGCTGGGAGACGCTTTCGGTCTACGACCCCGACCCGGAGGCGGTGGGCAAGAGCTACGCCGCGCGAGGGTGGATTC
TTGCCGGACATCGACCTGTTCGACGCGGACTTCTTCGGGATATCGCCCCGAGAGGCGCAGGCGATGGATCCCCAGCAGCG
GCTGGTGCTGGAGACGGCATGGGAGGCATTGGAGCGTGCCGGCGTGCGCCCGTCGGCGCTGAGCGGGAGCGCCACCGGGG
TGTATCTGGGGGCCGCGGGTTCGGACTATGGCGCTTACCAGGGTGGCGGGCTGGAGATGCTGGACGGGTACCGGGGCATC
GGGAGCGCGGCGAGCGTGCTCTCAGGCCGTGTGGCCTACGTGCTCGGGCTGCATGGCCCAGCGATGACGGTGGACACGGC
GTGCTCGTCGTCGCTGGTGTCGCTGCACCTCGCGTGCACGGCGTTGCGTCAGGGTGAATGCGACCTGGCGCTGGCCGGCG
GGGTGACGGTGATGAGCACCCCCGCGTTGTTCGTGGAGTTCAGCCGGCTCAAGGGGATGGCCCGAGACGGCCGCTGCAAG
AGCTTCTCTGGGCAGGCGGACGGCGCGGGCTGGTCGGAGGGGTGCGGGATGCTGGTGCTGAAGCGGCTGTCGGACGCGCG
GCGCGACGGTGACCGTGTGCTTGCGGTGGTCCGTGGGTCAGCGGTGAACCAGGACGGTCGCAGCCAAGGCCTGACGGCGC
CGAACGGCCCCGCGCAGCAGCGGGTGATCCAGCAGGCGCTGTCGTCGTGCGGGCTGTCGCCCGAGGACATCGACGCGGTG
GAGGCGCATGGTACGGGCACGAGCCTCGGAGATCCGATCGAGGCCGGAGCGCTCGCGGAAGTGTTCGGGCCTGGGCGCAA
GGCCGAGCGACCGCTGTACCTTGGCTCGTCGAAGTCGAACCTTGGGCACGCGCAGGCTGCGGCGGGCCGTAGCCGGTGTGC
TCAAGATGGTGCTGTCGATGCAGCACGAGGTGCTGCCGAAGACGCTGCACGCGGAGCAGCCGAGCCCGCACATTGGGTGG
GAGGGGAGCGGGCTGTCGTTGCTGCAAGAGGCGCCTCCGTGGCGGCGCAACGGCCGGGCGCGGCGCGCGGGCCGTGTCGTC
GTTCGGGATCAGCGGGACGAACGCCCATGTCATCCTCGAAGAGGCGCCGGTGGAGGCGGCTCGCGAGCCCGGTGGAGGCGG
TGCGCGAGCCGGTGGAGGCGGAGGGTGTTGCGATACCGCTGTTGCTGTCGGGGCGAGACGAGGCCTCGGTGGCGGCGCAG
GCGGGGCGGTGGGCGAAGTGGCTGGAAGAGCACGGGGAGGTGGGGTGGTCGGACGTGGTGAGGACGGCGGCGCTGCACCG
GACGCACTTCGAGTCGCGGGCGTCGGTGCTTGCGGCGAGCGCTGCGGGAGCTGTGGAGGGTCTTCGCGCGCTGTCGTCGG
GGCGGCCGGATGCGGCGGTGGTGAGCGGGACGGCGAAGCGAGGCGGGAAGCTTGCGGTGCTGTTCACGGGGCAGGGCAGC
CAGCGGCTCGGGATGGGGAAGAGGCTTTACGAAGTGTACCCCGTGTTCCGTGCGGCGTTCGACGAGGTGTGCGAGGCGCT
GGACGCGCATCTCGACCGTGGGTTGAGAGAGGTGGTGTTCGCGGCCGCGGGCAGCGAGGAAGGAGCGTTGCTGGAGCGGA
CGGAGTACACGCAGCCCGGGCTGTTTGCGCTGGAAGTGGCGCTGTACCGTCAGTGGGAGTCGTKGGGGCTGAARCCCGCT
GCGCTKCTKGGGCACTCGATAGGAGAGCTGAGCGCTGCGCACGTGGCGGGTGTGCTGAGCCTTGCGGACGCAGCGAAGCT
AGTGTGCGCCCGCGGTCGGCTGATGCAGGGGTGCGAGGCCGGGGAGCCGATGGTGTCGGTGGAGGCCTCGGAGCCGGATG
TGCAGCGGGCGCTGTCGGAGGTCGGGGCGCAGGGGCCGACTGAGCATCGCCGGGCTGAACGCGCCGATGCAGACGGTGCTG
AGCGGGGACGAAGCGGCCGGTGCTCGCGGTGGCGCGACGGCTGGAGGCGCAGGGCCGGCGCACCGCGGCGTCTGCGTGTGTC
GCACGCGTTCCACAGCGCCGCACATGGACGGGATGCTGGAGGAGTTCGGGAAGGTGGCGCGGGGGTGCACGTACGCGCGGC
CACGGCTGGCGGTGGTGAGCGGCCTGACGGGCGAGCTCGGTGGCGAAGAAGCGCTGATGTCGGCCGAGTACTGGGTGAGG
CAGGTGCGCGAGGCGGTGCGCTTCCTGGACGGGATGCGCACGCTTGCGGCGGCGGGGGTGAGCACATACGTCGAGTGTGG
GCCGGATGGCGTGCTGTGCGCGCTGGGGGCGGGGTGCCTGCCGGAGGGAGCCGAGGCGACGTTTGTGACGAGCCTGCGGC
GAGAGCAGGAGGAAGAGCGCCGCGCTTGCGACGGCGGTGGCGACAGTGCACGTGCAGGGGCACGAGGTGGACTGGGCCCAG
GTGCTGTCGGGCCGTGGCCGGCCGGCCCGTGGAGCTGCCGACGTACGCGTTCCAGCGGCAGCGCTACTGGCTGGAGGCCCC
CAAGACGACGGCGGCACAGGCGAATGTCTCGTGGCCGGAGCCGTGCGTTGTGGGACGCGGTGCAGAAAGGCGAAGGCGTTG
CGGATCTGCTGGAGCTGCCTGACGACGTGCCGCGAGAGCGTCGCGCCGCTGCTGCCGTACCTTGCGGCGTGGCGCCGGAGA
AGGGACGCAGAAGCCACGGTGTCTGGCTGGTTGTACGAGGAGGCGTGGCAAAGGGAAGCCAGCGCTGCCAGGGGCAAGCC
GGACGTGAGGGGCAGATGGCTGCTGGTGTCATCTCCCGCGTGCCGGAGGGCTGACCGCGGCGGTGAGTGATGCGCTCGGAG
CTGCCGGGTGCAGAGGTGATCATCGAGCCGGCGACCGAAGAGCGAGCGCAGCTGGCGGCCGAGGTTGAGAGGGCTGGAGGGC
GAGCTGCGTGGCGTCGTGGCGCTGAGCGCGCCTGGGGAGCAAGGTGCCCTGGAGGAAGGGCGAGGGCCTCGCGGAGTGTA
CGAGGTGCTGGCGCTGGCCGCAGGCGCTCGGTGACGCTGGGCTCGATGCGCGGCTCTGGGTGTTGACGCAGGGAGCGGTGA
GCACGGAGGCAAGCGAAGGGGTGTCCGACCCTGCCGCAGGCGCTGACGTGGGGGTTGGGGCGGGTGGTGGGGCTGGAGCAC
CCCGAGCGCTGGGGTGGACTGGTAGACCTGCCGGCGGAGGTGGACGCCGAAGCGGTGCAGCAGGTGCTGAGGACGCTCGT
TGCCCGAGGACCACCAGGACCAGGTGGCCGGTGCCGACGCCGGTGGGCGTCTTGTGCGGCGCATCGTGCGGGTGAGTGGAGAGG
ACGGCGGAGCGGGGTGGAAGCCCGCGTGGCACGGTGCTCATCACGGGTGGAGTGGGAGGGCTCGGGAGCCATCTGGCTCGC
```

FIG.1B

```
TGGTTGGCGGAGCGGGGAGCAGAGCACCTGGTGCTGGCGTCACGCCGGGGCGCCGCGGCAGCGGGCGCGCGCGAGCTTCG
GGAGGAGCTTGAGGGGCGGGGCGCGCGCCTGACGCTTGCGGCGTGCGATGTGTCGGAGCCGAGCGCAGGTCGAGGCGCTGG
TGAGGGAGCTTGAGCAGGACGAAGCGCCGCTGAGCGCGGTGGCGCATCTGGCGGGGATAGTCCGCCGCGTGCCGGTGCGA
GAGCTCGCGCCCGAGATGCTGGCGCAGGAGCTCGCGGCGAAGGTCAACGGAGCATGGCACCTGCAGGAGCTGCTGGCAGA
GCGCGAGCTGGATGCCGTTCGTGCTTTTATGGCAGCATCGCTGGGCTGTGGGGCTCTGGGACGCAGGCCGGGTACGGCGCGG
CGAACGCAGGGCTCGACGCCCTCGCGCGCTACCGGCGTGCCCGAGGGCAGACGGCGACGGTGCTGCACTGGGGCCCGTGG
TCCGGAGGCGGGATGGTGAGCGACGAGGCCGAGCCGCAGCTCCGGAGCCGCGGGCTGGTGCCGATGTCGCCCGACAAGGC
GCTTTGCGGGCTCGAGGTTGGGCTGCGGCGCACGTCGGTGGCGATCGCGGACGTGGACTGGTCGCGCTTCGCGCCCGCTGT
TCTGCGCGGCGCGGGCCGAGGCCGCTGCTGTACGGGATCGAGCAAGCGCGCCATGCGCTGGAGGGCCGGACACCGCAGCAG
GCCGCGGGCGGAGCGGGGACAAGGCGCTGCGGGAGATGCTGCTCGGCCTGCCGGCTGTGGAGCGGAGCCGAGCGGCTGCCG
CGAGCTCGTGGCGAGCGAGACGGCGGCCGTGCTGGGCGTGAAGGATCCGAGCGGGCTGGACCCGGAGCGAGGCTTTCTGG
ACCTCGGGCTGGACTCGTTGATGGCGGTGGAGCTGTCGAAGCGGCTGCAGCAGCGGACGGGGGTGTCGGTCACAAGGACG
TTGATCTTCGATTATCCGACGCAAGGCGAGGTAACGCGCTGGCTGCTGGAGCAGCTGATGCCGCCGGAGCGACCGGCGGC
GGACGAGCACGGCGTGAGCCGTGGACCGGAGCGGAGCGCGCCGATAGCGATCGTGGGCGTGGGGCTGCGCATGCCGGGCG
GAGCGAACGATCTGGAGAGCTTCTGGCAAGTGCTCGTGGAGGGGCGGGATACGCTAAGGCCGATCCCGACCGACCGTTTC
GACGTGGAGGCGATGTACGATCCTAACCCCGAGGCCAAGGGCAAGACGTACGTGAAGCATGCCTCGCTGCTGGACGACGT
GGCATCGTTTGACGCGGGGTTCTTCGGGATAAGCCCGCGCGAGGCGGAGCCGATGGATCCGCAGCACCGGCTGCTGCTGG
AGACTGCGTGGAGCGCGCTGGAGGACGCGGGAGTGCGTCCAGACCAGCTGAAGGGCTCGGACACGGGTGTGTTCGTGGGC
GTGGCGCCGAGCGAGTATGCGAGCTATCGCGGCAAGAGCGCGAACGAAGATGCGTATGCGCTGACGGGGACCGCGCTGAG
CTTCGCAGCGGGCCGTGTGGCATATCATCTCGGGCTGCAAGGCCCTGCGGTGTCGGTCGATACGGCGTGCAGCTCGTCGC
TGGTGGCGCTGCACCTGGCGTGCGACGCATTGAGGCGCGGCGATTGCGAGGTGGCTCTGGCCGGCCGGCGTGCAGGTGCTC
GCGAACCCGGCGGGGTTTGTGCTGCTGTCGCGCACGCGTGCGGTCTCGCCCGACGGACGGTGCAAGACGTTCTCGCAGGC
GGCCGACGGCTACCGGCCGCGGCGAGGGCGTCGGGGTGGTGGTGCTGATGCGTCTTTCGGACGCACAGGCGCAGGGGATGC
GGGTGCTGGGCGTGGTGCGGGGCACGGCGGTCAATCAGGACGGCGCGAGCAGCGGGATCACGGCGCCGAACGGCACGGCC
CAGCAGAAGGTGGTGCGCGCGGCGCTGCGGAACGCGGGGCTGGAGGCGTCGAGCATCGATGTGGTCGAGTGCCACGGTAC
GGGCACGTCGCTGGGCGATCCGATCGAGGTGCAAGCGCTCGGCGCGGTGTACGGGCAAGGCAGGGAGGCGACTCGCCCCGC
TGCGGCTTGGAGCGGTCAAGAGCAACATCGGTCACCTGGAGTCGGCCGCCGGCATCGCCGGAGTGTGCAAGATCCTGGCG
GCGTTTCGGCATGAGGCCCTGCCGGCGACGTTGCACAGCTCGCCGCGCAACCCCCAGATCTCCTGGGAGAGTCTGCCGGT
GCAGGTGGTCGACCGCCTGACCGGCTGGCCTCGGCGCGCCGACGGCCTCCCCCGCTTTGCGGGCGTGTCGTCGTTTGGCA
TCAGCGGGACGAACGCGCATGTCATCCTCGAAGAGGCGCCGCTTGAGGCGGTGCGCGAGCCGGCGGCGGTGCGCGAGCCG
TTGGCGGCGGAGGGTGTCGCGATCCCGCTGTTGCTGTCGGGGCGAGACGAGGCCTCGGTGGGGGCGCAGGCGGAGCGCTG
GGCGAAGTGGCTCGGAGAGCACGCGGAGGTGCCGGTGGCCGGACGTGGTGAGAACGGCGGCGCTGCACCGGACGCACTTCG
CCTGGCGCGCATCGGTGCAGGCGGCCGAGCGTGTCGGAGGCGGTGGAGGGCTGAGGCGCTGTCGGAGGGTCGAGCCGCG
GCAGGTGTGGTGCGCGGGACGGAGGGCGCGGGGGGAAGCTTGCGGTGCTGTTCACGGGGCAGGGGAGCCAGCGGCTCGG
GATGGGGAAGAGACTTTACGAAGTGTACCCCGTGTTCCGTGCGGCGTTCGACGAGGTGTGCGAGGCGCTGGACGCGCATC
TCGACCGTGGGTTGAGAGAGGTGGTGTTCGCGGAAGCGGGCAGCGAGCAGGAGGCGCTGCTGGAGCGGACGGAGTACACG
CAGCCCGGGTTGTTTGCGCTGGAAGTGGCGCTGTACCGGCAGTGGGAGGCGTGGGGAGTGAGGCCCGCGGCGCTGCTGGG
GCACTCGATAGGAGAGCTGAGCGCTGCGCACGTGGCGGGCGTGCTGAGCCTTGCCGACGCAGCGAAGCTAGTGTGCGCCC
GCGGTCGGCTGATGCAGAGGTGCCAGGCGGGCGGAGCGATGATGTCGGTGGAAGCGTCGGAGCCGGAGGTGCAGGGGGCG
CTGTCGGCGATGGGGCTGGAGGGCCGGCTTGGGATCGCGGGCATCAACGGTCCGAGCCAGACGGTGCTGAGCGGGGACGA
AGCGGCGGTGCTGGAGGTGGGCAGGCGGTTCGAGGCGCAGGGCCGGCGCACGCGGCGTCTGCGCCGTGTCGCACGCATTCC
ACAGCGCGCACATGGACGGGATGCTGGAAGAGTACGGGAGGGTGGCGCGGGAGTGCGCGTATGGGAGGCCGCAGGTACCC
GTGGTGAGCGGCCGTGACGGGCGAGCTCGGTGGCGAAGAATCGCTGATGTCGGCCGAGTACTGGGTGAGGCAGGTGCGCGA
GGCGGTGCGCTTCCTGGACGGGATGCGCACGCTTGCCGGCGGCGGGGTGAGCACATACGTCGAGTGCCGGTCCGGATGGCG
TGCTGTGCGCGCTGGGGGCGGGGTGCCTGCCGGAGGGAGCCGAGGCGACGTTTGTGGCGAGCCTGCGGCGAGAGCAGGAG
GAAGAGCGCGCGCTTGTGACGGCGGTGGCGACGGTGCACGTGCAAGGGCACGAGGTGGACTGGGCCCAGGTGCTGTCGGG
CCATGGCCGGCCGGCCCGTGGAGCTGCCGACCTACGCCGTTCCAGCGGCAGCGCTACTGGCTGGAGCGCCGAGGGCGCGCC
GCGACGTGGGCTCGGCGGGGCTGAAGGCCGGCCGCCCATCCGCTGCTCGGCGCCGCGACGAAGCTCGCCGACGGCGAGGGG
CACCTGTTCACAGGGAGGCTGTCGCTGGCCGGAGCATGCGTGGCTTCGGGATCATCAGGTGTTTGGCAAGGTGGTGTTTCC
GGGCACGGGGATGCTGGAGCTGGCGCTGGCCGGCGGGGCGCGCGGTGGGCAGCCGGACCGTGTCGGAGCTGGTTCTGGCCG
AGCCGCTGGTGCTGGCCCGAGGAGGCCGCGGCGCGGCTGCAGCTGTCGGTCGGAGCGCCGGACGCGGCGGGCCGGCGCGAG
GTAGGGCTGTACAGCCAGTCCGAGCAGGCGCCGGAGGACGCGCCGTGGGTGCAGCACGCCACGGGCGTGTTGACGGACGA
GATCCCCGGCGCCCCCGGCGAGCTCGACGAGCTGTCGACGTGGCCTGTGCCGGGCCGCCGAGGAGGTGGACCTGTCCGGGT
TTTACGAGCCGGCTGCCGTGAGGGCCGGGCTCGACTACGGTCCGGTGTTCCAGGGCCTCGTGGAGCTCTGGCGTCGAGGCCGCG
```

FIG.1C

```
AGGCTTTACGGCCGGGTGGTGTTGCCCGGGAGCGCGAGGGGCAGCGCCGAGGCGTATGGGGTGCATCCGGCGCTGATGGA
CGCCGCGCTCCACACGATGGTCGCAGCTTTCTCTCAGATGTCAGGGCCAGACGGCGTGTTGTTGCCCGTTCGCCTGGTCGG
ACGTGGCGCCGCACGCGACGGGGGCGAGCGAGCTTCGGATCCGAGTGGAGATGCAGGAACAAAGCGCACAGCAGCCAGCG
GCTTCGCTGTACGTCGCAGACTGCACGGGGCAGGTCGTGGCGAGCATCGGCGCTCTACGTCTGCGCCGGGCGACGGCCGA
GCAGCTGCGGACCGCCGTTCACGCTGGTGGCCAACATATGTATCAGGTGAGCTTCCAGCCTGTGGACCTCGCAGCACCTC
CCTTGGTGACGGGCTCGCTGGTGGTCATCGGTGCACCGAAGGGAGGAGCGCGGCTGGCCGAAGCCCTGGGGGCGGAGGCG
ATTGCCGATCTCGATGCATTGGTTGTGCGCCTCGAGCATGGCGCGAGCGCGCCTGAGCGGGTGGTGGTCGACGTCACCGC
CGCGAGCCCGAGCCCGTTGGACGTGGCGGGGTCGTCGCATGAGGCGACGAGGCAGGCGCTGTCGCTGCTGCAAGCGTGGC
TGTCGGAGCCGCGGCTCGAAGCGACCGAGCTGGTGTGGATCACGCGGGGCGCGGTGGGCGCGGCGCCAGACGACGCCGTC
GAGGACCTGGCCGCGCGCCGCTGTGGGGGCTTGTCCGCGCCGCGCGAAGCGAGCACCCCGAACGCGGGCTGCGCTTGAT
GGATGTGGGGACCGAGCCCGTGGACGCTGGGCTGCTGGCCGCGGGCGCTGGCGACGGCGGCGGAGCCGGAGCTTGCGCTGC
GCGGGGGCGCTGCGCTGGCCGCGCGCCTGGTGCCGCGCACAGGCGGTAGCGGAAGAGCTCACCCGAGCCCGCGAGCTGGAC
CCTGCGGGCACGGTGCTGGTGACCGGCGGGACAGGGGAGCTGGGTCAGGCGGTCGCGGCCGCACCTGGTGCCGCGCACGG
GGTGCGGCACCTTGTGCTGACGTCGCGGCGCGGGCTGGAGGCGCCCGGGGCCCGCGAGCTTGTGGAATCGCTCGCGGAGC
TCGGCGCCGAGACGGTGACGGTGGCCGCGTGCGACGTGTCGAAGCGGGAGGAGGTCGCGCGTGTGCTGGCCGGCATCGAC
GCGGCGCGCCCCGCTGAGCGCGGTGCTGCACCTGGCCGGCGCGCTCGACGACGGCGTGCTCGCCGGCCAGACGGCCGAGCG
CCTCTCGCGGGTGCTGGCGCCGAAGGTGGACGGGGCGCTGCACCTGCACGAGCTGACGCGGGAGCTGGATCTCGTGGCGT
TCGTGCTGTTCTCGTCGGTGGCCCGGTACGTTTGGCACGGCGGGCCAGAGCAACTACGCGGCGGCGAATACGTTCCTCGAC
GCGCTCGCGGCGCACCGGCGCGGCTGCGGGCTCGCGGCGACGAGCCTGGCGTGGGGGTTGTGGGCGCAAGCGGGCGTGGG
GATGACAGCGCACCTGGGCGAGGCCGAACTGTCGCGCATCAGGCGCGCAGGGCTCGTGCCGATATCGGTCGACGAGGGCC
TCGCTCTGCTGGACGCCCGCTCTCACGCTCTGAAGCGAGCCTGGTGCCAGTGCACCTGGATCTCGCGCAGCTGCAGCGT
GGGCTGGAGTCCAGCGGCGAGCTGCCGGCGCTGCTTCGCGGCGCTGGTGCGCCCCGGGCTGCGCAAGGCGTCCTCTGCCGC
GAGGAAGGAGGCGTCGACGCTCCGCGAGCGCCTCTCGGCGCTGCCGGAGGCGGAGCGCCTGAGCTCGCTCATCGACCTTG
TGCGGGCCGAGGTCGCCCGCGGTGCTCGGGCTTCAGCGCGGTGACGCGATTCCTACGGCCCAGCCCTTGAGGGAGCTCGGA
ATGGATTCGCTCATGGCCGTCGAAGTCCGCAATCGGCTCGCCTTGCTGGTCGGAAGCAACTTGCCTGCCACTTTGCTTTT
CGACCATCCATCTGCCACGCACATCGCGAAGTTCCTCCTGTCAAAGTTCGGAAACGGTGAGCGCCGGAATCTGCTGCGTA
CAGCGGACTCCATGTCCGACGAGGAAATTCGCGCGTTCATGCTCAGCCTGTCCGTCAGTCTCGTGCGTCGTTCAGGCCTC
CTCCCCAAGCTCTTGGAGCTGCGGGGGCCGTCCGAAACATCCGTCGAGGTTCCGGTTCCCATTTCCGATTTCGAAGATCT
CGCCGACGAGCAGCTGGCCTTGCAAGCCTTGCAAATGATTTCGAACTCAGAGGATCTCCATGAATAGCAGCGCCGCCTCT
CCTACGCTTCGTGAGGCGTTGACCCGTGCATTGAAAGAGTTGCAGAGGCTGCAGGCCAGCCACTCGGATCTCCGTTCAGG
GCCCATCGCCATCGTATCGATGGCGTGCCGGCTGCCGGGGGCGTCGCTACGCCGGAAGACTACTGGCGTCTCCTGGAGG
AGGGGAGAGATGCGATCGAGGCCTTCCCTGCGCGCTGGGATGCACCTTCGATTTACGACCCCGATCCGGAGGCGGTGGGC
AAGACCTACGTGCCGCGAGGGTGGATTCCTGCGGGACATCGACCTGTTCGATGCGGGTTTCTTCGGGATATCGCCCCGAGA
GGCGCAGGCGATGGATCCCCAGCAGCGGCTGGTGCTGGAGACGGCGTGGGAGGCACTGGAGCGGGCTGGCCGTGCGCCCGT
CGGCGCTGAGCGAGAGCTCCACCGGGGTGTACCTGGGCTCGATGGGCTCGGACTACGGTGCTCTTTACGGCAGCGACCTG
GCGGCGTTGGACGGCTACCGGGGCACCGGGAGCGCGGCGAGCGTGCTCTCAGGCCGTGTGGCGTACGTGCTCGGGCTGCA
GGGCCCAGCCGATCACGGTGGACACGGCGTGCTCGTCGTCGCTGGTGTCGCTGCACCTGGCGTGCACGGCCCTGCCGTCAGG
GCGAGTGCGATCTGGCCCTTGACCGGTGGGGTGATGGTGATGACCACACCCGCGGGATTCGTGGAGTTCAGCCGCCTCAAG
GCCCTTGCACGGGACCGGTCGTTGCAAGAGCTTCTCTGCCGCAGCTGACGGCGTCATCTGGTCCGAGGGGTGCGGGATGCT
GGTGCTGAAGCGGCTGTCGGACGCGCGGCGCGACGGTGACCGTGTGCTGGCGGTGATCCGTGGGTCAGCGGTGAACCAGG
ACGGTCGCAGCCAGGGTTTGACGGCGCCGAACGGCCCTGCCCAGCAGCGGGTGATCCAACAGGCGCTCTCGTCGTGCCGG
CTGTCGCCCGAGGACATCGACGCGGTGGAGGCGCATGGGACGGGCACGAACCTGGCGACCCGATCGAGGCCCGGAGCGCT
CGTGGAGGTGTTCGGGCCTGGGCGCAAGGCCGAGCGGCCCGCTGTACCTTGGCTCGTCGAAGTCGAACCTGGGACACGCGG
GGCCTGCGGCGGGCGTCGCCCGGTGTGCTCAAGATGGTGCTGTCGATGCAGCACGAGGTGCTGCCGCCGGACGCTGCACGCG
GAGCAGCCGAGCCCGCACATTGGGTGGGAGGGGAGCGGGCTGTCGTTGCTGCAAGAGGCGCGTCCGTGGCGGCGCAACGG
CCGGGCGCGGCGCGCGGGCGTGTCGTCGTTCGGGATCAGCGGGACGAACGCGCATGTCATCCTCGAAGAGGCGCCGGTGG
AGGCGGCGCGCAGCCGGTGGAGGCAATGCGCGAGCCGTTGGCGACGGAGGGTGTTGCGATGCCGCTGTTGCTGTCGGGG
CGAGACGAGGCCTCGGTGGGGGCGCAGGCGGAGCCGCTGGGCGAAGTGGCTCGGAGAGCACGGGGAGGTGCAGTGGTCGGA
CGTGGTGAGGACAGCGGCCGCTGCACCGGACGCACTTCGCCTCACGCGCATCGGTGCTTGCGGCGAGCCGTGTCCGAGGCGG
AGGAGGCGCTGCGGGCGCTGTCGCAGGGTCGCGGCCACCGGGCGGTGTCGGCGGGTACGGCGCGTGCGCGAGGCAAGGTG
GTGTTCGTGTTCCCCGGCCAAGGGAGCCAGTGGCCGGGGATGGGCCGGGCGCTGCTGGAGCAGAGCGCGGCGTTCGCGGA
GGCGGTGCAGGCGTGCGATGAGGCGCTGCCGGCCGTGGACGGCTGGTCTGTGCTGTCGGTGCTGCGCGGAGATGGCGGGG
AGGAGCAGCCGTCGCTGGAGCGGGTGGACGTGGTGCAGCCCGCGCTGTTCGCGATGTGCGTGGGTCTGGCCGCGGCGTGG
CGGTCGCTGGGGCTGGAGCCTGCGGCGGTGGTGGGCCACAGCCAGGGCGAGGTGTCGGCGGCGGTGGTGTGCCGGAGCGCT
```

FIG.1D

```
GTCGCTTGCGGAGGGAGCGCGGGTAGTGGCGCTGCGCAGCCAGGCGGTGCGGCAGCGGTCGGGGATGGGGGCGATGATGC
TGGTCGAGCGGCCGGTGTCGGAGGTGCAGGAGCGCATCGCGCCGTACGGGGAGGCGCTTGCGATAGCGGCGGTGAACACG
TCGAGCTCGACGGTGGTGTCGGGTGACGTGGAGGCGGTGGACGGGCTGATGGTGGAGCTGACGGCAGAAGGTGTGTTCTG
CCGGAAGGTGAACGTCGACTACGCGTCGCACAGCGCGCACATGGATGCGCTGCTGCCCGAGCTAGGAGCGAAGCTGTCGT
CGCTCAGGCCCGAAGGCGACGCAGCTGCCCGTTTTACTCGACGGTGACAGGAGAGGTGTCGCGGGGCGAGGCCGCTGGACGGC
GAGTACTGGTGCCGCAACCTTCGGCGGACGGTGCGCCTGGACCGAGCGCTGTCGAAGCTGCTGGAGGACGGGCACGGTGT
GTTCGTGGAGGTGAGCGCGCACCCGGTGCTGGCGATGCCGCTGACGACGGCGTGCGGGAGGCGCAGGGGGTGGTGGTGG
GGAGCCTGCAGCGCGACGAAGGTGGGTTGTCGCAGCTGTACAGGACGCTGGGGCAGCTGCACGTGCAGGGGCACGACGTG
GACTGGACACGGGTGCTGTCGGGCCACGGCGGTCGTGTCGTGGAGCTGCCGACGTACGCGTTTCAGCGGCAGCGTTACTG
GCTGGATATCTCGAAGGCGCGTAGCGACGTGAGCTCGGCGGGGCTCAAGGCAGCAGCACACCCGCTGCTCGGCGCCGCGA
CGAGGCTCGCCGACGGCGAGGGGCACCTGTTCACAGGGCGGCTGTCGCTGGCGGAGCATCCGTGGCTTCGGGATCATGAG
GTGTTTGGCCAGGTGGTGCTTCCGGGCACGGGGACGCTGGAGCTGGTGCTGGCGGCGGGGCGCGCGGTGGGCAGCCGGTC
GCTGTCGGAGCTCACGCTGGCCGAGCCGCTGGTGCTGGCCGAGGGCGCGGCGCGGCTGCAGGTGATGATCGGAGCGCCGG
ACGCGGCGGGCCGGCGCGAGGTGGGGCTGTACAGCCAGCCTGAGCAGGCCCCGGAGGACGCGCCGTGGGTGCAGCACGCG
ACGGGAGTGTTGACGGAGGAGCCCCCCGGCATCCCTGTCGAGCTCGACGAGCTGTCGACGTGGCCCTGTGCCGGGCGCGGA
GGAGGTGGACCTGTCCGGGCTTTACGAGCGGCTGCGTGAGCGCGGGCTCCACTACGGCCCGGCGTTTCAAGGGCTCGTGG
AGCTGTCGCGCCAAGGCACAACCTACTTCGGTCGGGTGGTGCTGCCGGGGACCGAGAAGGACAGGGCGGAGGCGTATGGC
GTGCACCCGGCGTTGATGGACGCCGCGCTCCACACGATGGTCGCGGCCTTCTCCGAGAGCCCAGGGGCGAACGAGGTGCT
CGTGCCGTTTGCCTGGTCGGACGTGGCGCTGCACGCGACGGGGCGAGCGAGCTTCGGGTCCGGGTAGAGCTCCAGGACG
GAGGCGCACACCAGGACACCGCTTCGCTGCAAGTCGCAGACTCCACGGGGCAGGCCGTGGCGAGCATCGGCGCTCTACAT
CTGCGCCGGCCGACGGCCGAGCAGCTGCGGACCGCCGTTCACGCTGGTGGCCAACATATGTATCAGGTGAGCTTCCAGCC
TGTGGAGCTCGCCGCAGCCCCCTGGAGGCGGGCTCGCTGGTGGTCGTCGGTGCAGCGGAGGGACGAGGCAGGCTGGCCG
AAGCCCTGAGGGCGGAGGCGATTGCCCGATCTCGAAGCATTGGTTGCGCGCCTCGAGCAGGGCGCGAGCGCGCCTGCCGG
GTGGCGGTCGACACGACAGCTTTAGGACAGAGTCAGTCGGGAGTGGCGTCGTTGTCCCACGAGGCGACGAGGCAGGCGCT
GTCGCTGCTGCAAGCGTGGCTGTCGGAGCCGCGGCTCGACGCTGTCGAGCTGGTGTGGGTGACGCGGGGCGCGGTGGGCG
CGGCGCCGGACGACGCCGTCCAGGATCTGGCGCGCGCGCCGCTGTGGGGGCTTGTTCGGCGGCGCGCAGCGAGCACCCC
GAGCGCCCGGCTGCGCTTGATCGATGTGGGGACCGAGCCCGTGGACGCTGGGCTGCTGGCCGGGGCGCTGGCCGACGGCGGC
GGAGCCGGAGCTTGCGCTGCGCGGGGCGCTGCGCTGGCCGCGCGCCTGGTGCGCGCGCAGGCGGCAGCGGAAGAGCTCA
CCCCGAGGAGCCCGCGAGCTGGACCCTGCGGGCACGGTGCTGGTGACCGGCGGGACAGGGGAGCTGGGTCAGGCGATCGCG
GCGCACCTGGTGCGCGCGCACGGGGTGAGGCACCTTGTGCTGACGTCGCGTCGCGGGCTGGAGGCGCCCGGGGCCCGCGA
GCTCGTGCAGTCACTCGAGGAGCTCGGCGCCGAGACGGTGACGGTGGCTGCGTGCGACGTGTCGAAGCGGGAGGAGGTCG
CCCGTGTGCTGGCCGGCATCGACGCGGCGCGTCCGCTGAGCGCGGTGCTGCACCTGGCCGGCGTGCTCGACGACGGCGTG
CTCACCGCCCAGACGGCCGAGCGCCTCTCGCGGGTGCTGGCGCCGAAGGTGGACGGGGCGCTGCACCTGCACGAGCTGAC
GCGGGAGCTGGATCTCGCGGCGTTCGTGCTGTTCTCGTCGGCGGCCGGTACGTTTGGCGCGGCGGGCCAGAGCAACTACG
CGGCGGCCAACACGTTCCTCGACGCGCTCGCGGCGCACCGGCGCGGCGGCGGGCTCGCGGCGACGAGCCTGGCGTGGGGC
TTCTGGACACAGGCGGGCGTGGGGATGACAGCGCACCTGGGCGAGGCCGAGCTGTCGCGCATGAGGCGCAATGGGTTCGT
GCCCGATGCCGGTGGAAGAGGGCCTCGCTCTGCTGGACGCCGCGCTCTCACGCCCTGAAGCGAGCCTGGTCCCAGTGCACC
TGGATCTCGCGCAGCTGCAGCGTGGGCTGGAGTCCAGCGGCCGAGCTGCCGGCGCTGTTTCGTGCCGCTGTTGCGCCCCGAGC
TTGCGCAAGGCGTCCTCGGCAACGAGGCGAGACGCCTCGGCGCTCCGCGAGCGCCTCTCGGCGCTGCCCGGAGGCGGAGCG
GCTGAATGCCGCTCGTCGAGCTGGTGCGGGGCGAGGTTGCGGCCGTGGCAGGGCTTCAGCGCGGCGAGGCTGTGGCAGCGG
ATCAGGTGCTCAAGGAGCTGGGGCTCGACTCGCTGATGGCGGTGGCGCTGCGCAACCGCCTCACGTCCCGTACCGAGACG
TCCTTGCCGGCGACGCTGGTCTTTGACTACCCGACGCCGGGGCGATCGCAGAGCTGCTGCTGAAGCAGGCGTTCTCGGG
GCTGCAGGTGAAGGAAGCGCGGGCGCGGGTGCGTCGTCGTGCAGGGAAAGACGAGCCGATCGCGATCGTGTCGATGGCGT
GCCGGCTGCCGGGAGGCGTTGCCGACGCCGGACGACTACTGGCGTCTCTTGGCCGAGGGGAAGGACGCGATCGAAGGCCTC
CCAGCCGCTGGGACGGGTTCGAGGTCTACGACCCTGATCCGGAGGCCGCAGGCAAGAGCTACGCGCGCGAAGGTGGGTT
TGTTCGGGACATCGACCTGTTCGACGCGAACTTCTTCGGGATATCGCCGCGCGAGGCGCAGTCGATGGATCCGCAGCATC
GGCTGGTGCTGGAGACGGCGTGGGAGGCATTGGAGCGTGCCGGCGTGCGCCCGTCGGCGCTGAGCGGGAGCGCCACCGGA
GTGTACCTGGGTTCGATGGGCTCGGACTACGGTGCTCTTCATACTGTCGATCTGAAGGAGCTGGACGGGTACCGGGGCAT
CGGGAGCCGCGGCCGAGCATCCTCTCGGGCCGGGTGGCCTACGCGCTGGGGCTGCAGGGCCCAGCCGATGACGGTGGACACGG
CGTGCTCGTCGTCGCTGGTGTCGCTGCACCTGGCGTGCACGGCGCTGCGCCAGGGCGAATGCGACCTGGCGCTGGCCGGC
GGGGTGACGGTGATGAGCACCCCCGCGCTGTTCGTGGAGTTCAGCCGTCTCAAGGGGATGTCCCGCGACGGTCGGTGCAA
GAGCTTCTCGGTGCAGGCGGACGGCCGGGCTGGGCCGAGGGTTGCGGGATGCTGTTGTTGAAGCGGCTGTCTGACGCGC
AGCGCGACGGCGACCGTGTGCTGGGGGTGATCCGTGGCTCTGCCGGTGAACCAGGACGGTCGCAGCCAGGGTCTGACGGCG
CCGAACGGCCCTGCCCAGCAGCGGGTGATCCGGCAGGCGCTGTCGTCGTGTGGTCTGTCGCCCGAGGACATCGACGCCGGT
```

FIG.1E

```
GGAGGCGCACGGTACGGGCACGAGCCTTGGAGACCCGATCGAGGCCGGAGCGCTGGCGGAGGTGTTTGGACCGGAGCGTA
GCCCCGAGCGTCCGCTGTACCTGGGATCGTCGAAGTCGAACCTCGGACATGCGCAGGCGGCCGGCGGGCGTGGCGGGCCGTG
ATCAAGATGGTGCTGTCGATGCAGCACGAGGTGCTGCCGAAGACGCTGCACGCGGAGCAGCCGAGCCCGCACATTCGGTG
GGAAGGAAGCGGGCTGTCGCTGCTGCAAGAGGCGCGTCCGTGGCGGCGCAACGGCCGGGTCCGTCGTGCCGGCGTGTCGT
CGTTCGGGATCAGCGGGACGAACGCGCATATCATCCTCGAAGAAGCGCCGGCCGAGGCGCGGCGCGAGCCTGTCGAGGCC
GAGGCGGCGCCTGCGCTATTGCCGCTGGTGCTGTCGGGTCGAGACGAGGCCGCGGTGAATGCGCAGGCGGGGCGGTGGGC
GAAGTGGCTGGAAGAGCACGGGGAGGTGGGGTGGTCGGACGTGGTGCGCACGGCGGCGCTGCACCGGACGCACTTCGAGT
CGCGGGCGTCGGTGCTTGCGGCGAGCGCTGCGGGAGCTGTGGAGGGTCTTCGCGCGCTGTCGTCGGGGCGGCCGGATGCCG
GCGGTGGTGAGCGGGACGGCGAAGCGAGGCGGGAAGCTTGCGGTGCTGTTCACGGGGCAGGGCAGCCAGCGGCTCGGGAT
GGGGAAGAGGCTTTACGAAGTGTACCCCGTGTTCCGTGCGGCGTTCGACGAGGTGTGCGAGGCGCTGGACGCGTATCTCG
ACCGTGGGTTGAGAGAGGTGGTGTTCGCGGCCGCGGGCAGCGAGGAAGGAGCGTTGCTGGAGCGGACGGAGTACACGCAG
CCCCGGGCTGTTTGCGCTGGAAGTGGCGCTGTACCGTCAGTGGGAGTCGTGGGGGCTGAAGCCCGCTGCGCTGCTGGGGCA
CTCGATAGGAGAGCTGAGCCGCTGCCGCATGTGGCGGGTGTGCTGAGCCTTGCGGACGCAGCGAAGCTAGTGTGCGCCCGAG
GTCGGCTGATGCAAGGGTGCGAGGCCGGGGAGCGATGGTGTCGGTGGAGGCCTCGGAGCCGGAGGTGCAGCGGGCGCTG
TCGGAGGTCGGGGCGCAGGGGCGACTGAGCATCGCCGGGCTGAACGCGCCGATGCAGACGGTGCTGAGCGGGGACGAAGC
GGCGGTGCTCGCGGTGGCGCGGCGGCTGGAGGCGCAGGGCCGGCGCACGCGGCGTCTGCCGTGTGTCGGCACGCGTTCCACA
GCGCGCACATGGACGGGATGCTGGAGGAGTTCGGGAAGGTGGCGCGGGAGTGCACGTACGCGCGCGGCCACGGCTGGCGGTG
GTGAGCGGCGTGACGGGCGAGCTCGGTGGCGAAGAAGCGCTGATGTCGGCCCGAGTACTGGGTGAGGCAGGTGCCGCGAGGC
GGTGCGCTTCCTGGACGGGATGCGCACGCTTGCCGGCGGCGGGGGTGAGCACATACGTCGAGTGTGGGCCGGATGGCCGTGC
TGTGCGCGCTGGGGGCGGGGTGCCTGCCGGAGGGAGCCGAGGCGACGTTTGTGACGAGCCTGCGGCCGAGAGCAGGAGGAA
GAGCGCGCGCTGGCGACGGCGGTGGCGACAGTGCACGTGCAGGGGCACGAGGTGGACTGGGCCCGGGTGCTGTCGGGCCG
TGGCGGCCGGCCCGTGGAGCTGCCGACGTACGCGTTCCAGCGGCAGCGCTACTGGCTGGAAGCGCCGAAGAGCGCGGCGA
CCGAGGTGAATGTCTCCAGCGCGGAGCAGGCGCTGTGGAATGCGGCGCTGGAGGGCGAGGGAGATGGCGTTGCGGAGCTG
CTGGAGCTGCCTGACGACGTGCGCGCCAGCGTCGGGCCGCTGCTGCCGTACCTCGCGGCGTGGCGCCAGAGAAAGCAGGC
AGAAGCGGCGGCGGCGAGCTGGCTGTATGAGGAAGCGTGGCAAAAACCGTCCGAGGCGTGTGACGGGTAGTCCGGATGTAA
GGGGCACCTGGCTCGTGGTGTCACCTCCGCTTGCCGGAGAGCTTGCGGAGGTGGTGCGTGGTGCGCTCGGCGCCGCGGGG
GCCGAGGTGATCGTGCACATCGCCGGCCGTGGAGCGAGCGCAGCTCGCAGCGTGGCTGAGAGAGCAAGCGCGCCTGAGAAA
GGAGGAGGGCGAGCTGCCGTGGCGTCATCGCGCTCACGGCCTCAGGCGAGGAAGGCGCGCTGGAGCAAGGGCAGGCGCCCC
GCAGCCTGTACCAGACGCTGGCCGGTGGTGCAGGCGCTCGGCGACGCCCGGAATCGGCGCGCGGCTGTGGTTGCTCACGCAG
GGAGCGGTCAGCACCGAGCCAAGCGAAGCGGTGGTGCACCCGTTGCAGGCGCTGACGTGGGGACTGGGACGGGCGTTGGG
GCTGGAGCACCCCGAGCGCTGGGGCGGGCTGCTGGACGTGCCGGCGGAGCTGGACGCGGGCGTGATGCAGCACGTCTTGA
CCACGCTTGTGTCCGACGACAACGAAGATCAGGTGGCGGTGCGGCGCGGCGGGCGCCTCGTGAGGCGCATTGTGCGTGTG
CGCGGCGAGGGCGACGGCGAGGGCTGGAAGCCGCGCGGCACGGTGCTCATCACGGGCGGCGTGGGCGGCTCGGAGGTCA
TCTTGCCCGCTGCCTGGCCCGGGCGTGGCGCAGAGCACCTTGTGCTGGCCGTCGCGCCGCGGCGCGTCGGCGCCCCGGGCGA
GCGAGCTGCGGGACGAGCTTGTGGCGCGGGGCATTCGGGTGACGCTGGCGGCCGTGTGACGTGTCGGAGCGCGCGCAGCTC
GCGGCGCTGCTCGCGGAGCTGGAGCAGGATGAAGCGCCCGCTGAGGGCGGTGGCGCACCTCGCGGGCATAGGCCGCCGTGT
TCCGCTGCCGAGAGCTCGAGCCTGAGCAGCTCGAGCAGGAGCTCGCGGCGAAGGTGAAGGGGGCGTGGCACCTGCATCAGC
TGCTGGGGAAGCGGGAGCTGGATGCCGTTCGTGCTCTATGGCAGCATCGCCGGGCTGTGGGGCTCCGGGGCGCAGGCTGGG
TACGGCGCAGCCGAACGCAGGGCTGGACGCGCTCGCGCGGTACCGGCGCGCGCGAGGGCAGGCTGCCGACGGTGTTGCACTG
GGGCCCCTGGGCGGGAGAAGGGATGGTGACCAGCGAGCTCGAGTCGCAGCTGCGGATCCGCGGGGTCGCGGTGATGTCGC
CCGACAAGGCGCTCGCCCGGGCTGGAGATGGCGCTGCCGGCTGGGGCGCACGTCGGTGGCGATCGCCGACCGTGGACTGGTCG
CGCTTCCGCGCCGTCGTTCAGCGCGGCGAGGCCGAGGCCGCTCCTGGACGGGATCGAGGAGGCCCGGCGGGCGCAGGAGAG
CCGCGGCCCGCAGCCGGCCGCAGGCGGGACCGCGCTGAGAGACACCTTGCTGGGCCTGAGCGAGGCCGAGCGGCGCGAGC
GGGTACGTCAGCTGGTGGCGAGCGAGACGGCCGCGGTACTGGGCATGACGGACCCGAGCCGGCTTGACCCGGACCGTGGC
TTTCTGGACCTCGGGCTGGATTCGCTGATGGCGGTGGAGCTGTCGAAGCGGCTGCAGAAGCGCACGGGCATGACGGTACC
GAGCACGCTGAGCCTTCGATCACCCGACGCAGAGCGACGTGGCGCGCTGGCTGCTGGAGCAGCTCACACCTCAGCCGCGAC
CGGAGCCGGCGGTGCGCGAGGTGAGCCGGGAAGAGGGGTGGAGCACGCCGATAGCGATCGTGGGCCGTGGGCTGCGCATG
CCTGGCCGAGCCAGCCGACCTGGAGAGCTTCTGGCAGGTGCTGGTCGAAGAGCGGGATACGCTGCGGCCGATCCCGGCCCA
ACGATTCGACGTCGAGGCGCTGTACGATCCTGACCCCGACCCGAAGGGCAAGACGTACGTGCGGAACGCGTCGCTGCTCG
ACGACGTGGCGTCGTTCGACCCTGGGTTCTTCGGGATAAGTCCGCGGGAGGCGGAGCCGATGGATCCGCAGCACCGGCTG
CTGCTGGAGACGGCGTGGAGCGCCCTGGAGGACGCGGGGGTGCGTCCAGAGCACCTGAAGGGCTCGGACACGGGAGTGTT
CGTGGGCGTGGCGCCGAGCCGAATACGCGAGCTACCGAGGAAAGAGCGCGAACGAAGATGCGTATGCGCTGACAGGGACGG
CGCTGAGCTTTGCTGCGGGACGGGTGGCCTACCACCTCGGGCTGCAAGGCCCTGCGGTGTCGACCGACACGGCCTGCAGC
TCGTCGCTGGTAGCGGTGCACCTGGCCGTGCCGACGCGCTGCGCCGGGGCCGATTGCGAGGTGGCGCTGGCCGGCAGGTGTGCA
```

FIG.1F

```
GGTGCTGGCCGAACCCGGCGGGGTTTGTGCTGCTGTCGCGCACGCGCGCGTTGTCGCCGGACGGGCGGTGCAAGGCGTTCT
CGCAGGCGGCGGACGGTTATGGCCGTGGCGAGGGAGTCGGGGTGCTGGTGCTGATGCGGCTGTCCGAGGCGCAGCAGCAG
GGGAAGCGGGTGCTGGGTGTGGTGCGCGGCACGGCGGTCAATCAGGACGGCGCGCAGCAGCGGGATCACGGCGCCCGAACGG
CACGGCCGCAGCAGAAGGTGGTGCGCGCGGCGCTGCGGAACGCGGGGCTGGAGCCGGCGAGCATCGATGTGGTGGAGTGCC
ACGGTACGGGCACGTCGCTGGGCGACCCGATCGAGGTGCAGGCGCTCGGCGCGGTGTACGGGCAAGGTCGGGATATGGCT
CGTCCGCTGCAGCTGGGCGCGGTCAAGAGCAATATCGGTCATCTCGAGTCCGCCGCGGGCATCGCAGGGGTGTGCAAGAT
CCTGGCCGGCCGTTCCGTTACGAGTCGCTGCCGGCGACGCTGCACAGCTCGCCCGCGCAATCCCCGCATCCCGTGGGAGAACC
TGCCGGTGCAGGTGGTCGATCGCCTGACCCCCTGGCCTCGGCGCGCAGAGGGCCCCCCGCGCCGTGCCGGCGTGTCGTCG
TTCGGGATCAGCGGGACGAACGCGCATGTCATCCTCGAAGAAGCGCCCGGCCGAGGCGCGGCGCGAGCCTGTCGAGGCCGA
GGCGGCGCCTGCGCCTATTGCCGCTGGTGCTGTCGGGTCGAGACGAGGCCGCGGTGAATGCGCAGGCGGGGCGGTGGGCGA
AGTGGCTGGAAGAGCACGGGGAGGTGGGGTGGTCGACGTGGTGCGCACGGCGGCGCTGCACCGGACGCACTTCGAGTCG
CGGGCGTCGGTGCTTGCGGCGAGCGCTGCGGGAGCTGTGGAGGGTCTTCGCGCGCTGTCGTCGGGGCGGCCGGATGCGGC
GGTGGTGAGCGGCACGGCGAAGCGAGGCGGGAAGCTTGCGGTGCTGTTCACGGGGCAGGGCAGCCAGCGGCTCGGGATGG
GGAAGAGGCTTTACGAAGTGTACCCCGTGTTCCGTGCGGCGTTCGACGAGGTGTGCGAGGCGCTGGACGCGCATCTCGAC
CGTGGGTTGAGAGAGGTGGTGTTCGCGGCCGCGGGCAGCGAGGAAGGAGCGCAGCTGGAGCGGACGGAGTACACGCAGCC
CGGGCTGTTTGCGCTGGAAGTGGCCGCTGTACCGTCAGTGGGAGTCGTGGGGGCTGAAGCCCGCTGCCGCTKCTGGGGCACT
CGATAGGAGAGCTGAGCGCTGCGCACGTGGCGGGTGTGCTGAGCCTTGCGGACGCAGCCGAAGCTAGTGTGCGCCCGCGGT
CGGCTGATGCAGGGGTGCGAGGCCGGGGGAGCGATGGTGTCGGTGGAGGCCTCGGAGCCGGAGGTGCAGCGGGCGCTGTC
GAAGGTCGGGGCGCAGGGGCGACTGAGCATCGCCCGGGCTGAACGCGCCGATGCAGACGGTGCTGAGCGGGGACGAAGCGG
CCGTGCTCCGCGGTGGCGCGACGGCTGGAGGCGCAGGGCCGGCGCACGCGGCGTCTGCCGTGTGTCGCACGCGTTCCACAGC
GCGCACATGGACGGGATGCTGGAGGAGTTCGGGAAGGTGGCGCGCGGGAGTGCACGTACGCGCGGCCCGCAGCTGGCGGTGGT
GAGCGGCCGTGACGGGCGAGCTCGGTGGCCGAAGAAGCGCTGATGTCGGCCGAGTACTGGGTGAGGCAGGTGCGCGAGGCGG
TGCGCTTCCTGGACGGGATGCGCACGCTTGCGGCGGCGGGGGTGAGCACATACGTCGAGTGTGGGCCGGATGGCGTGCTG
TGCGCGCTGGGGGCGGGGTGCCTGCCGGAGGGAGCCGAGGCGACGTTTGTGGCGAGCCTGCGGCGAGAGCAGGAGGAAGA
GCGCGCGCTGGCCGACGGCGGTGGCCGACAGTGCACGTGCAGGGGCACGAGGTGGACTGGGCCCAGGTGCTGTCGGGCCGTG
GCGGCCGGCCCGTGGAGCTGCCGACGTACGCGTTCCAGCGGCAGCGCTACTGGCTGGAAGCGCCCAAGGCGCGTACCGAC
GTGGGCTCGGCGGGCTTGAGGGAGTCGGGGCATCCGCTGCTCGGAGCGGCAACGAAGCTGGCCGACGGCGACGGCCATCT
ATTCACAGGCCGGCTGTCGCTGGGCGAGCAGCCGTGGCTTCGCGACCATGCGGTGTTTGGCGAGGTGGTCTTCCCGGGCA
CGGGGATGCTGGACCTCGCGCTGGCGGCTGGGCGCACGGTGGGCAGCGGGGCGCTGTCGGAGCTCACGATCTCCGAGCCG
CTGATGCTCGCGGAGGACGTGGCCGTGCCGGCTGCAGCTCTCGGTCGGGGCGCCCGACGCCGCGGGGCGGCGTGCGTTTGG
GCTGTACAGCCAGCCGGAGCAGGGACCGGGAGATGCCCCTGGGTGCAGCACGCGACGGGCGTGTTGACCGACGAGACCC
TCGCCACCTCCGGCGAGCTCGATGAGCTGACGACGTGGCCAGTGCCCGGCGCCGAGGCGGTGGACCTCTCCGGGTTCTAC
GAGCGGCTGCATGAGCGTGGACTCCGCTACGGCCCGGCCTTCCAGGGGCTCGTGGAGCTGTCGCGTCGAGACGCGACCTT
CTTCGGCCGGGTGGTGTTGCCCAAAAGACGCGACCGACAGCGCCCGAGGACTACGGGGTGCATCCGGCGCTGATGGACGCCG
CGCTGCATACGATGGTCGCAGCCGTTTGCGGAGGTATCAGCGCCCGGACGACGTGCTGCTGCCTTTCTCGTGGTCGGACGTG
GCGTTGCACGCCACGGGGGCGAGCGAGCTCCGGGTGAGGCTGGAGCTCGCAGGAGGCAGAGACTCGGCACAGGCAGCCGC
CTCGCTGCCGCGTTACAGATGCCGCCGGCCAGCCGGTGGTGAGCGTCGGTGCCCTGCATCTGCGCCGGGCGACGGCCGAGC
AGCTGCGGGCAGCGACGCATGCCGAGGCGCAGCACCTGTACCGGGTGGACTTCCAGCTCGTGAGCCTCGTGGAGGCGGGC
TCGAAGGTGGACTCGCTGGTGGTGCTCCGTGCGCCTGAGGGGCGAGGGCGACTGGGCGAAGCGCTGGGTGTGGAGGCGAT
CGCAGGCCTCGATGCATTGCTCGCGCCGGATCGAGCAGGGAACCCGATTGCCTGAGCGGGTGCTGGTCGACATGACGGCTG
GCAGCTCACAGCGCTCGGACATGGTGATATCGTCGCACGAGGCGACGGGACAGGCGCTGTCGCTGCTGCAAGCGTGGCTG
TCGGAGCCCCGGCTCGAGGGGTGGAGCTGGTGTGGGTGACGCCGAGATGCCGGTCAGCGCCGCTCCGGGCGACGGTGTCCA
AGACCTGGCGCACGCGCCGCTGTGGGGCTTGTTCGCACGGCGCGAAGCGAGCACCCCGAGCGCCGGCTGCCGCCTGATCG
ACGTTGGGACCGAGCCTCTGGACGGCGGGCTGCTGGCCGCGCGCGCTGGCGACGGCGACGGAGCCCGGAGCTTGCGCTGCGT
GGCGGCGCGGCGATGGCGGCCGCGCCTGGTGCGCGTGCCGGCCGGCAGCGGAAGGGCTCACGCCGGCGCGCGGGCTGGACCC
GACGGGCACGGTCCTGGTGACCGGAGGAACAGGCGAGCTGGGTCAGGCCGTCGCCGGAGCATCGGTGCGCGCACACGGGG
TGCGGCACCTCGTGCTGACGTCGCGCCGTGGGCTGGAGGCGCCCGGGGCCCCAGGCTTCGTGCAGCGCGCTGGAGAAGCTC
GGTGCCGAGACCGTGACGGTGGCGGCCGTGTGACGTGTCGAAGCGGGAGGAGGTCGCGCGCCGTGCTGGCCGGCATCGAGGC
CGCACATCCGCTGACCGCGGTGCTGCACCTGGCCGGCGTGCTCGACGATGGCGTCATCACCGCGCAGACGCCCGAGCGTC
TCTCGCGGGTGCTGGCGCCGAAGGTGAACGGGGCGCTGCACCTGCACGAGCTGACAGAGGATCTCGATCTCTCGGCCTTC
GTGCTGTTCTCCTCGATGTCCGGGACGCTCGGGACGGCGGGCCAGAGCAACTACGCGGCGGCCAACAGCTTCCTCGACGC
GTTCGCGGCGCATCGCCGCAGCCGCGGGCTCGCGGCGACGAGCCTGGCGTGGGGCTTCTGGGCGCAAACGGGCGTGGGCA
TGACAGCGCACCTGGGCGAGGCGGAGCTCTCACGTATCCAGCGCGCCGGACTTGTGCCCGATACGGGTCGAGGAGGGCCTT
TCGCTGCTGGACGCCGCGCTTCTGCGCCCCGAAGCGAGCCTGGTGCCTGCGCACCTCGATCTTGCGCAGATGCAGCGGGG
```

FIG.1G

```
GCTGGAGGCCAGCGGCGAGCTGCCCGCGCTGCTTCGCGCGCTGCTGCGCCCTGGGCTGCGCAAGGCGTCATCCGCCACGA
GGAAGGAAGCCTCGGCGCTCCGCGAGCGCCTCTCGGAGCTGCCGGAGGCGGAGCGCCTGAGCTCGCTCGTCGAGCTGGTT
CGGGCCGAGGTGGCCGCGGTGCTCGGGCTGCCGCGCAGCGAGGCCCGTTGCGGTAGATCAGGTGCTGAAGGACCTAGGGCT
AGATTCGTTGATGGCGGTGGAGCTGCGCAGTCGGCTCAGCGCCCGAGCCGAGATCCCCCTCCCGGCGACGCTGGTGTTCG
ACTACCCGACGCCGCGCGCCGTCGCAGAGCTGCTCCTGAGACAGGCTTTCTCGAAGCAGCAGGTGACGGCAGCGCGGGCG
CGTCGCCGGACGAAGGAAGACGAGGCGATCGCGATCGTATCGATGGCGTGCCGGTTGCCAGGGGGCGTGGCGACGCCGGA
AGACTACTGGCGTCTCCTGGCGGAAGGGAAGGACGCCATCGAGCGCTTTCCCTCCCGTTATGACGCGTTCTCTGTTTATG
ACCCCGATCCGGAGGCGGTGGGCAAGAGCTACGTGCGCGAGGGTGGATTCCTGCGGGATATCGATGTCTTCGACGCAGGC
TTCTTCGGGATCTCGCCGCGCGAGGCGCAGGCGATGGATCCCCAGCAGCCGGCTGGTGCTGGAGACGGCGTGGGAGGCGCT
GGAGCGAGCCGGCGTGCGGCCCTCGATGCTGAGCGAGAGCGCCACCGGGGTATACCTGGGCTGGATGGGCTCGGACTACG
GTGCTCTTCTCGGCAATGACCTCGCCGCGCTGGACGGGTACCAGGGTACGGGGAGCGCGGCGAGCGTGCTTTCAGGCCGG
GTGGCTTACGTGCTGGGGCTTCAGGGCCCAGCGATCACGGTGGACACGGCGTGCTCGTCGTCGCTGGTGTCGCTGCACCT
GGCGTGCACGGCGCTGCGCCAGGGCGAATGCGACCTGGCGCTGACCGGCGGGGTGATGGTGATGACCACGCCCGCGGGAT
TCGTTGAGTTCAGTCGTGCCCGGGGGCTTGCGCGAGACGGTCGGTGCAAGAGCTTCTCTGCCCAGGCTGACGGCGTCATC
TGGTCCGAAGGGTGCGGGATGCTGTTGCTGAAGCGGCTGTCTGACGCGCGGCGCGACGGCGACCGTGTGCTGGGGGTGAT
CCGTGGCTCTGCGGTGAACCAGGACGGTCGCAGCCAGGGTCTGACGGCGCCGAACGGCCCTGCCCAGCAGCGGGTGATCC
GGCAGGCGCTGTCGTCGTGTGGTCTGTCGCCCGAGGACATCGACGCGGTGGAGGCGCATGGGACGGGTACGAGCCTCGGA
GACCCGATCGAGGCCGGAGCGCTGGCGGAGGTGTTTGGACCGGAGCGTAGCCCCGAGCGTCCGCTGTACCTGGGGTCGTC
GAAGTCGAACCTGGGACATGCGCAGGCCGGCCGCGGGTGTGGCGGGCGTGATCAAGATGGTGCTGGCGCTGCAGCACGAGG
TGCTGCCGAAGACGCTGCATGCGGAGCAGCCGAGCCCGCACATCGCGTGGGAGGGGAGCGGGCTGTCATTGCTGCAAGAG
GCGCGTCCGTGGCGGCGCAACGGCCCGGGTCCGTCGTGCCGGCGTGTCGTCGTTCGGGATCAGCGGGACGAACGCGCATAT
CATCCTCGAAGAAGCGCCGGCCGAGGCGCGGCGCGAGCCTGTCGAGGCCGAGGCGGCGCCTGCGCTATTGCCGCTGGTGC
TGTCGGGTCGAGACGAGGCCTCGGTGGCCGGCCCAGGCCGGGCCGGTGGGCCGAAGTGGCTGGAAGAGCACGGGGAGGTGGGG
TGGTCGGACGTGGTGCGCACGGCGGCGCTGCACCGGACGCACTTCGAGTCGCGGGCGTCGATGCTTGCGGCGAGCGTGTC
CGAGGTGGTGGAGGTGCTGCGGGCGCTGTCAGAGGGTCGCGGCCACCGGGCGGTGTCCGTGGGCACGGCGCGTGCGCGAG
GCAAGGTGGTGTTCGTGTTCCCCGGCCAAGGGAGCCAGTGGCCGGGGATGGGCCGGCGCTGCTGGAGCAGAGCGCAGCCG
TTCGCGGAGGCGGTGCAGGCGTGCGATGAGGCGCTGCCGGCCGTGGACGGGCTGGTCTGTGCTGTCGGTGCTGCGCGGAGA
TGGCGGGGAGGAGCAGCCCGTCGCTGGAGCGGGTGGACGTGGTGCAGCCTGCGCTGTTCGCGATGTGCGTGGGTCTGGCCG
CGGCGTGGCGGTCGCTGGGGCTGGAGCCTGCGGCGGTGGTGGGCCACAGCCAGGGCGAGGTGTCGGCGGCGGTGGTGTGC
GGGGCGCTGTCGCTTGCGGAGGGAGCGCGGGTAGTGGCGCTGCGCAGCCAGGCGGTGCGGCAGCAGTCGGGGATGGGGGC
GATGATGCTGGTCGAGCAGCCCGGTGTCGGAGGTGCAGGAGCGCATCGCGCCGTACGGGAGGCGCTTGCGATAGCGGCGG
TGAACACGTCGAACTCGACGGTGGTGTCGGGTGACGTGGAGGCGGTGGACGGGCTGATGGTGGAGCTGACGGCAGAAGGT
GTGTTCTGCCGGAAGGTGAACGTCGACTACGCGTCGCACAGCGCGCACATGGATGCGCTGCTGCCCGAGCTAGGAGCGAA
GCTGTCGTCGCTCAGGCCGAAGGCGACGCAGCTGCCCGTTTTACTCGACGGTGACAGGAGAGGTGTCGCGGGGCGAGGCGC
TGGACGGCGAGTACTGGTGCCCGCAACCTTCGGCAGACGGTGCGCCTGGACCGAGCGCTGTCGAAGCTGCTGGAGGACGGG
CACGGTGTGTTCGTGGAGGTGAGCGCGCACCCGGTGCTGGCCGATGCCGCTGACGACGGCGTGCGGGGAGGCGCAGGGGT
GGTGGTGGGGAGCTTGCAGCGCGACGAAGGTGGGTTGTCGCAGCTGTACAGGACGCTGGGGCAGCTGCACGTGCAGGGGC
ACGAGGTGGACTGGGCACGGTGCTGTCGGGCCATGGTGGTCGTGCCGTGGAGCTGCCGACGTACGCGT:TCCAC:CGGC
AGCGCTACTGGCTGGATATCTCGAAGGCGCGTAGCGACGTGAGCTCGGCGGGGCTGAAGGCGGCCGCCCATCCGCTGCTG
GGAGCAGCAACG:AAGCTGGCTGAGGGCGATGGCCATCTGTTCACCGGCCGGCTGTCGCTGGGCGAGCATGCCGTGGCTCC
GCGACCATG:AGGTGTTTGGTAACTTGGTGTTCCCCCGGGCGCGGGGRATGCTGGAGCTTGCGCTGGCGGCTGGGCCGCA
CGGTGGGCAACGGGGGCTTTTCGGGAAAG
```

FIG.1H

Contig1_orf1
Asp Pro Gln Gln Arg Leu Val Leu Glu Thr Ala Trp Glu Ala Leu Glu Arg Ala Gly Val
Arg Pro Ser Ala Leu Ser Gly Ser Ala Thr Gly Val Tyr Leu Gly Ser Met Gly Ser Asp
Tyr Gly Ala Leu His Thr Gly Gly Leu Glu Ala Leu Asp Gly Tyr Arg Gly Thr Gly Ser
Ala Ala Ser Val Leu Ser Gly Arg Val Ala Tyr Val Leu Gly Leu Gln Gly Pro Ala Ile
Thr Val Asp Thr Ala Cys Ser Ser Ser Leu Val Ser Leu His Leu Ala Cys Thr Ala Leu
Arg Gln Gly Glu Cys Asp Leu Ala Leu Ala Gly Gly Val Thr Val Met Ser Thr Pro Ala
Leu Phe Val Glu Phe Ser Arg Leu Lys Gly Met Ala Arg Asp Gly Arg Cys Lys Ser Phe
Ser Ala Arg Ala Asp Gly Val Thr Trp Ser Glu Gly Cys Gly Met Leu Val Leu Lys Arg
Leu Ser Asp Ala Arg Arg Asp Gly Asp Arg Val Leu Ala Val Val Arg Gly Ser Ala Val
Asn Gln Asp Gly Arg Ser Gln Gly Leu Thr Ala Pro Asn Gly Pro Ala Gln Gln Arg Val
Val Gln Arg Ala Leu Ser Ser Cys Gly Leu Ser Pro Glu Asp Ile Asp Ala Val Glu Ala
His Gly Thr Gly Thr Ser Leu Gly Asp Pro Ile Glu Ala Gly Ala Leu Ala Glu Val Phe
Gly Pro Gly Arg Lys Ala Glu Arg Pro Leu Tyr Leu Gly Ser Ser Lys Ser Asn Leu Gly
His Thr Gly Pro Ala Ala Gly Val Val Gly Val Leu Lys Met Val Leu Ser Met Gln His
Glu Val Leu Pro Arg Thr Leu His Ala Glu Gln Pro Ser Pro His Ile Gly Trp Glu Gly
Ser Gly Leu Ser Leu Leu Gln Glu Ala Arg Pro Trp Arg Arg Asn Gly Arg Ala Arg Arg
Ala Gly Val Ser Ser Phe Gly Ile Ser Gly Thr Asn Ala His Val Ile Leu Glu Glu Ala
Pro Val Glu Ala Ala Arg Glu Pro Val Glu Ala Val Arg Glu Pro Leu Ala Thr Glu Gly
Val Ala Met Pro Leu Leu Leu Ser Gly Arg Asp Glu Ala Ser Val Ala Ala Gln Ala Glu
Arg Trp Ala Lys Trp Leu Glu Glu His Ala Glu Val Gly Trp Ser Asp Val Val Arg Thr
Ala Ala Leu His Arg Thr His Phe Ala Ser Arg Ala Ser Val Leu Ala Ala Ser Val Ser
Glu Ala Glu Glu Ala Leu Arg Ala Leu Ser Gln Gly Arg Gly His Arg Ala Val Ser Ala
Gly Thr Ala Arg Ala Arg Gly Lys Val Val Phe Val Phe Pro Gly Gln Gly Ser Gln Trp
Pro Gly Met Gly Arg Ala Leu Leu Glu Gln Ser Ala Ala Phe Ala Glu Ala Val Gln Ala
Cys Asp Glu Ala Leu Arg Pro Trp Thr Gly Trp Ser Val Leu Ser Val Leu Arg Gly Glu
Ala Gly Glu Ala Gly Glu Glu Gln Pro Ser Leu Glu Arg Val Asp Val Val Gln Pro Ala
Leu Phe Ala Met Cys Val Gly Leu Ala Ala Ala Trp Arg Ser Leu Gly Leu Glu Pro Ala
Ala Val Val Gly His Ser Gln Gly Glu Val Ser Ala Ala Val Val Cys Gly Ala Leu Ser
Leu Ala Glu Gly Ala Arg Val Val Ala Leu Arg Ser Gln Ala Val Arg Gln Arg Ser Gly
Met Gly Ala Met Met Leu Val Glu Arg Pro Val Ser Glu Val Gln Glu Arg Ile Ala Pro
Tyr Gly Glu Ala Leu Ala Ile Ala Ala Val Asn Thr Ser Ser Ser Thr Val Val Ser Gly
Asp Val Glu Ala Val Asp Gly Leu Met Gly Glu Leu Thr Ala Glu Gly Val Phe Cys Arg
Lys Val Asn Val Asp Tyr Ala Ser His Ser Ala His Met Asp Ala Leu Leu Pro Glu Leu
Gly Ala Lys Leu Ser Ser Leu Arg Pro Lys Ala Thr Gln Leu Pro Phe Tyr Ser Thr Val
Ala Gly Glu Val Ser Arg Gly Glu Ala Leu Asp Gly Glu Tyr Trp.Cys Arg Asn Leu Arg
Gln Thr Val Arg Leu Asp Arg Ala Leu Ser Lys Leu Leu Glu Asp Gly His Gly Val Phe
Val Glu Val Ser Ala His Pro Val Leu Ala Met Pro Leu Thr Thr Ala Cys Gly Glu Ala
Gln Gly Val Val Val Gly Ser Leu Gln Arg Asp Glu Gly Gly Leu Ser Gln Leu Tyr Arg
Thr Leu Gly Gln Leu His Val Gln Gly His Glu Val Asp Trp Ala Arg Val Leu Pro Gly
His Gly Gly Arg Ala Val Glu Leu Pro Thr Tyr Ala Phe Gln Arg Gln Arg Tyr Trp Leu
Glu Ala Pro Arg Ala Arg Gly Asp Val Ser Ser Ala Gly Leu Lys Ala Ala Ala His Pro
Leu Leu Gly Ala Ala Thr Lys Leu Ala Asp Gly Glu Gly His Leu Phe Thr Gly Arg Leu
Ser Leu Ala Glu His Ala Trp Leu Arg Asp His Gly Val Phe Gly Gln Val Val Phe Pro
Gly Thr Gly Met Leu Glu Val Ala Leu Ala Ala Gly Arg Ala Val Gly Ser Arg Ser Leu
Ser Glu Leu Thr Leu Ala Glu Pro Leu Val Leu Ala Glu Asp Gly Ala Ala Arg Leu Gln
Val Met Ile Gly Ala Pro Asp Ala Ala Gly Arg Arg Glu Val Gly Leu Tyr Ser Gln Pro
Glu His Ala Pro Glu Asp Ala Pro Trp Val Gln His Ala Thr Gly Val Leu Thr Asp Glu
Leu Pro Gly Ile Pro Asp Glu Leu Asp Glu Leu Ser Met Trp Pro Val Pro Gly Ala Glu
Glu Val Asp Leu Ser Gly Phe Tyr Glu Arg Leu Arg Glu Arg Gly Leu His Tyr Gly Pro
Thr Phe Gln Gly Leu Val Glu Leu Ser Arg Gln Gly Thr Arg Leu Tyr Gly Arg Val Val
Leu Pro Gly Thr Glu Lys Asp Arg Ala Glu Ala Tyr Gly Leu His Pro Val Leu Met Asp
Ala Ala Leu Gln Val Leu Gly Ala Ala Gly Glu Gly His Trp Glu Ala Asp Ala Leu Phe
Met Pro Phe Ser Trp Ala Asp Ala Ala Thr His Ala Thr Gly Pro Ser Glu Leu Arg Val
Arg Val Glu Leu Glu Glu Thr Asp Gly Ser Thr Gln Ala Thr Ala Ser Leu Cys Ala Ala

FIG.3A

Contig1_orf1

Asp Ala Ala Gly Gln Pro Val Ala Ser Val Gly Ala Leu Arg Leu Arg Arg Val Thr Ala
Glu Gln Leu Arg Ala Val Thr Arg Thr Asp Glu Gln His Leu Tyr Arg Val Ser Phe Gln
Pro Val Ser Leu Ala Gln Ala Pro Leu Glu Ala Gly Ser Leu Val Val Leu Gly Ala Ala
Glu Gly Arg Gly Gln Leu Ala Asp Thr Leu Gly Ala Glu Ala Ile Ala Asp Leu Asp Ala
Leu Arg Ala Trp Ile Glu Arg Gly Ala Pro Thr Pro Val Arg Val Val Ile Asp Thr Asn
Ala Ala Ser Ser Pro Arg Ser Asp Val Ala Gly Ser Ser His Glu Ala Thr Arg Gln Ala
Leu Ser Leu Leu Gln Ala Trp Leu Ser Glu Pro Arg Leu Asp Ala Val Glu Leu Val Trp
Val Thr Arg Gly Ala Val Ser Ala Ala Pro Asp Asp Ala Val Glu Asp Leu Ala His Gly
Pro Leu Trp Gly Leu Ile Arg Thr Ala Arg Ser Glu His Pro Glu Arg Arg Leu Arg Leu
Ile Asp Val Gly Thr Glu Pro Val Asp Ala Gly Leu Leu Ala Arg Ala Leu Ala Thr Ala
Ala Glu Pro Glu Leu Ala Leu Arg Gly Gly Ala Val Leu Ala Ala Arg Leu Val Arg Val
Gln Ala Ala Ala Glu Glu Leu Thr Arg Ala Arg Gly Leu Asp Pro Ala Gly Thr Val Leu
Val Thr Gly Ala Val Gly Gly Leu Gly Gln Ala Val Thr Arg His Leu Val Arg Ala His
Gly Val Arg His Leu Val Leu Thr Ser Arg Arg Gly Leu Glu Ala Pro Gly Ala Arg Glu
Leu Val Gln Ser Leu Glu Glu Leu Gly Ala Glu Thr Val Ser Met Val Ala Cys Asp Val
Ser Lys Arg Glu Glu Ile Ala Arg Val Leu Ala Gly Ile Asp Ala Ala Arg Pro Leu Ser
Ala Val Leu His Leu Ala Gly Val Val His Asp Gly Val Ile Gln Thr Gln Thr Ala Glu
Arg Leu Ala Trp Val Leu Ala Pro Lys Val Asp Gly Ala Leu His Leu His Glu Leu Thr
Arg Glu Leu Asp Leu Ala Ala Phe Val Leu Phe Ser Ser Ala Ala Gly Thr Leu Gly Met
Ala Gly Gln Gly Asn Tyr Ala Ala Ala Asn Thr Phe Leu Asp Ala Phe Ala Ala His Arg
Arg Gly Arg Gly Leu Ala Ala Thr Ser Leu Ala Trp Gly Val Trp Thr Pro Ala Gly Gly
Gly Met Ala Ala Gln Leu Gly Ala Ala Glu Leu Ala Arg Phe Ser Arg Tyr Gly Val Val
Ser Met Ser Val Glu Glu Gly Leu Ser Leu Leu Asp Ala Ala Leu Ser Arg Pro Glu Ala
Ser Leu Val Pro Met His Leu Asp Leu Ala Gln Leu Gln Arg Gly Leu Glu Ala Asn Gly
Glu Leu Pro Ala Leu Phe Arg Ala Leu Leu Arg Pro Ser Leu Arg Lys Ala Ser Thr Ala
Thr Arg Arg Asp Ala Ser Ala Leu Arg Gly Arg Leu Ser Ala Leu Pro Glu Ala Glu Arg
Leu Asn Ala Leu Ile Glu Leu Val Arg Gly Val Ala Ala Val Leu Gly Leu Gln Arg
Ser Glu Ala Val Gly Ala Glu Gln Val Leu Lys Gly Leu Gly Leu Asp Ser Leu Met Ala
Val Glu Leu Arg Asn Arg Leu Ala Ala Arg Thr Glu Thr Ser Leu Pro Ala Thr Leu Val
Phe Asp Tyr Pro Thr Pro Arg Ala Ile Ala Glu Leu Leu Leu Lys Leu Ala Phe Ser Gly
Pro Gln Val Met Gly Ala Arg Arg Gly Val Arg Arg His Ala Gly Lys Asp Glu Ala Val
Ala Ile Val Ser Met Ala Cys Arg Leu Pro Gly Gly Val Glu Thr Pro Glu Asp Tyr Trp
Arg Leu Leu Ala Glu Gly Lys Asp Val Ile Glu Gly Leu Pro Ala Arg Trp Glu Thr Leu
Ser Val Tyr Asp Pro Asp Pro Glu Ala Val Gly Lys Ser Tyr Ala Arg Glu Gly Gly Phe
Leu Arg Asp Ile Asp Leu Phe Asp Ala Asp Phe Phe Gly Ile Ser Pro Arg Glu Ala Gln
Ala Met Asp Pro Gln Gln Arg Leu Val Leu Glu Thr Ala Trp Glu Ala Leu Glu Arg Ala
Gly Val Arg Pro Ser Ala Leu Ser Gly Ser Ala Thr Gly Val Tyr Leu Gly Ala Ala Gly
Ser Asp Tyr Gly Ala Tyr Gln Gly Gly Gly Leu Glu Met Leu Asp Gly Tyr Arg Gly Ile
Gly Ser Ala Ala Ser Val Leu Ser Gly Arg Val Ala Tyr Val Leu Gly Leu His Gly Pro
Ala Met Thr Val Asp Thr Ala Cys Ser Ser Ser Leu Val Ser Leu His Leu Ala Cys Thr
Ala Leu Arg Gln Gly Glu Cys Asp Leu Ala Leu Ala Gly Gly Val Thr Val Met Ser Thr
Pro Ala Leu Phe Val Glu Phe Ser Arg Leu Lys Gly Met Ala Arg Asp Gly Arg Cys Lys
Ser Phe Ser Gly Gln Ala Asp Gly Ala Gly Trp Ser Glu Gly Cys Gly Met Leu Val Leu
Lys Arg Leu Ser Asp Ala Arg Arg Asp Gly Asp Arg Val Leu Ala Val Val Arg Gly Ser
Ala Val Asn Gln Asp Gly Arg Ser Gln Gly Leu Thr Ala Pro Asn Gly Pro Ala Gln Gln
Arg Val Ile Gln Gln Ala Leu Ser Ser Cys Gly Leu Ser Pro Glu Asp Ile Asp Ala Val
Glu Ala His Gly Thr Gly Thr Ser Leu Gly Asp Pro Ile Glu Ala Gly Ala Leu Ala Glu
Val Phe Gly Pro Gly Arg Lys Ala Glu Arg Pro Leu Tyr Leu Gly Ser Ser Lys Ser Asn
Leu Gly His Ala Gln Ala Ala Ala Gly Val Ala Gly Val Leu Lys Met Val Leu Ser Met
Gln His Glu Val Leu Pro Lys Thr Leu His Ala Glu Gln Pro Ser Pro His Ile Gly Trp
Glu Gly Ser Gly Leu Ser Leu Leu Gln Glu Ala Arg Pro Trp Arg Arg Asn Gly Arg Ala
Arg Arg Ala Gly Val Ser Ser Phe Gly Ile Ser Gly Thr Asn Ala His Val Ile Leu Glu
Glu Ala Pro Val Glu Ala Ala Arg Glu Pro Val Glu Ala Val Arg Glu Pro Val Glu Ala
Glu Gly Val Ala Ile Pro Leu Leu Leu Ser Gly Arg Asp Glu Ala Ser Val Ala Ala Gln

FIG.3B

Contig1_orf1
Ala Gly Arg Trp Ala Lys Trp Leu Glu Glu His Gly Glu Val Gly Trp Ser Asp Val Val
Arg Thr Ala Ala Leu His Arg Thr His Phe Glu Ser Arg Ala Ser Val Leu Ala Ala Ser
Ala Ala Gly Ala Val Glu Gly Leu Arg Ala Leu Ser Ser Gly Arg Pro Asp Ala Ala Val
Val Ser Gly Thr Ala Lys Arg Gly Gly Lys Leu Ala Val Leu Phe Thr Gly Gln Gly Ser
Gln Arg Leu Gly Met Gly Lys Arg Leu Tyr Glu Val Tyr Pro Val Phe Arg Ala Ala Phe
Asp Glu Val Cys Glu Ala Leu Asp Ala His Leu Asp Arg Gly Leu Arg Glu Val Val Phe
Ala Ala Ala Gly Ser Glu Glu Gly Ala Leu Leu Glu Arg Thr Glu Tyr Thr Gln Pro Gly
Leu Phe Ala Leu Glu Val Ala Leu Tyr Arg Gln Trp Glu Ser Gly Leu Lys Pro Ala Ala
Leu Leu Gly His Ser Ile Gly Glu Leu Ser Ala Ala His Val Ala Gly Val Leu Ser Leu
Ala Asp Ala Ala Lys Leu Val Cys Ala Arg Gly Arg Leu Met Gln Gly Cys Glu Ala Gly
Gly Ala Met Val Ser Val Glu Ala Ser Glu Pro Asp Val Gln Arg Ala Leu Ser Glu Val
Gly Ala Gln Gly Arg Leu Ser Ile Ala Gly Leu Asn Ala Pro Met Gln Thr Val Leu Ser
Gly Asp Glu Ala Ala Val Leu Ala Val Ala Arg Arg Leu Glu Ala Gln Gly Arg Arg Thr
Arg Arg Leu Arg Val Ser His Ala Phe His Ser Ala His Met Asp Gly Met Leu Glu Glu
Phe Gly Lys Val Ala Arg Gly Cys Thr Tyr Ala Arg Pro Arg Leu Ala Val Val Ser Gly
Val Thr Gly Glu Leu Gly Gly Glu Ala Leu Met Ser Ala Glu Tyr Trp Val Arg Gln
Val Arg Glu Ala Val Arg Phe Leu Asp Gly Met Arg Thr Leu Ala Ala Ala Gly Val Ser
Thr Tyr Val Glu Cys Gly Pro Asp Gly Val Leu Cys Ala Leu Gly Ala Gly Cys Leu Pro
Glu Gly Ala Glu Ala Thr Phe Val Thr Ser Leu Arg Arg Glu Gln Glu Glu Glu Arg Ala
Leu Ala Thr Ala Val Ala Thr Val His Val Gln Gly His Glu Val Asp Trp Ala Gln Val
Leu Ser Gly Arg Gly Gly Arg Pro Val Glu Leu Pro Thr Tyr Ala Phe Gln Arg Gln Arg
Tyr Trp Leu Glu Ala Pro Lys Thr Thr Ala Ala Gln Ala Asn Val Ser Trp Pro Glu Arg
Ala Leu Trp Asp Ala Val Gln Lys Gly Glu Gly Val Ala Asp Leu Leu Glu Leu Pro Asp
Asp Val Arg Glu Ser Val Ala Pro Leu Leu Pro Tyr Leu Ala Ala Trp Arg Arg Arg Arg
Asp Ala Glu Ala Thr Val Ser Gly Trp Leu Tyr Glu Glu Ala Trp Gln Arg Glu Ala Ser
Ala Ala Arg Gly Lys Pro Asp Val Arg Gly Arg Trp Leu Leu Val Ser Ser Pro Arg Ala
Gly Gly Leu Thr Ala Ala Val Ser Asp Ala Leu Gly Ala Ala Gly Ala Glu Val Ile Ile
Glu Pro Ala Thr Glu Glu Arg Ala Gln Leu Ala Ala Arg Leu Arg Gly Leu Glu Gly Glu
Leu Arg Gly Val Val Ala Leu Ser Ala Pro Gly Glu Gln Gly Ala Leu Glu Glu Gly Arg
Gly Pro Arg Gly Val Tyr Glu Val Leu Ala Leu Ala Gln Ala Leu Gly Asp Ala Gly Leu
Asp Ala Arg Leu Trp Val Leu Thr Gln Gly Ala Val Ser Thr Glu Ala Ser Glu Gly Val
Ser Asp Pro Ala Gln Ala Leu Thr Trp Gly Leu Gly Arg Val Val Gly Leu Glu His Pro
Glu Arg Trp Gly Gly Leu Val Asp Leu Pro Ala Glu Val Asp Ala Glu Ala Val Gln Gln
Val Leu Arg Thr Leu Val Ala Glu Asp His Glu Asp Gln Val Ala Val Arg Arg Gly Gly
Arg Leu Val Arg Arg Ile Val Arg Val Ser Gly Glu Asp Gly Gly Ala Gly Trp Lys Pro
Arg Gly Thr Val Leu Ile Thr Gly Gly Val Gly Gly Leu Gly Ser His Leu Ala Arg Trp
Leu Ala Glu Arg Gly Ala Glu His Leu Val Leu Ala Ser Arg Arg Gly Ala Ala Ala Ala
Gly Ala Arg Glu Leu Arg Glu Glu Leu Glu Gly Arg Gly Ala Arg Val Thr Leu Ala Ala
Cys Asp Val Ser Glu Arg Ala Gln Val Glu Ala Leu Val Arg Glu Leu Glu Gln Asp Glu
Ala Pro Leu Ser Ala Val Ala His Leu Ala Gly Ile Val Arg Arg Val Pro Val Arg Glu
Leu Ala Pro Glu Met Leu Ala Gln Glu Leu Ala Ala Lys Val Asn Gly Ala Trp His Leu
Gln Glu Leu Leu Ala Glu Arg Glu Leu Asp Ala Phe Val Leu Tyr Gly Ser Ile Ala Gly
Leu Trp Gly Ser Gly Thr Gln Ala Gly Tyr Gly Ala Ala Asn Ala Gly Leu Asp Ala Leu
Ala Arg Tyr Arg Arg Ala Arg Gly Gln Thr Ala Thr Val Leu His Trp Gly Pro Trp Ser
Gly Gly Gly Met Val Ser Asp Glu Ala Glu Pro Gln Leu Arg Ser Arg Gly Leu Val Pro
Met Ser Pro Asp Lys Ala Leu Cys Gly Leu Glu Val Gly Leu Arg Arg Thr Ser Val Ala
Ile Ala Asp Val Asp Trp Ser Arg Phe Ala Pro Leu Phe Cys Ala Ala Arg Pro Arg Pro
Leu Leu Tyr Gly Ile Glu Gln Ala Arg His Ala Leu Glu Gly Arg Thr Pro Gln Gln Ala
Ala Gly Gly Ala Gly Asp Lys Ala Leu Arg Glu Met Leu Leu Gly Leu Pro Ala Val Glu
Arg Ser Glu Arg Leu Arg Glu Leu Val Ala Ser Glu Thr Ala Ala Val Leu Gly Val Lys
Asp Pro Ser Gly Leu Asp Pro Glu Arg Gly Phe Leu Asp Leu Gly Leu Asp Ser Leu Met
Ala Val Glu Leu Ser Lys Arg Leu Gln Gln Arg Thr Gly Val Ser Val Thr Arg Thr Leu
Ile Phe Asp Tyr Pro Thr Gln Gly Glu Val Thr Arg Trp Leu Leu Glu Gln Leu Met Pro
Pro Glu Arg Pro Ala Ala Asp Glu His Gly Val Ser Arg Gly Pro Glu Arg Ser Ala Pro

FIG.3C

Contig1_orf1

Ile Ala Ile Val Gly Val Gly Leu Arg Met Pro Gly Gly Ala Asn Asp Leu Glu Ser Phe
Trp Gln Val Leu Val Glu Gly Arg Asp Thr Leu Arg Pro Ile Pro Thr Asp Arg Phe Asp
Val Glu Ala Met Tyr Asp Pro Asn Pro Glu Ala Lys Gly Lys Thr Tyr Val Lys His Ala
Ser Leu Leu Asp Asp Val Ala Ser Phe Asp Ala Gly Phe Phe Gly Ile Ser Pro Arg Glu
Ala Glu Pro Met Asp Pro Gln His Arg Leu Leu Leu Glu Thr Ala Trp Ser Ala Leu Glu
Asp Ala Gly Val Arg Pro Asp Gln Leu Lys Gly Ser Asp Thr Gly Val Phe Val Gly Val
Ala Pro Ser Glu Tyr Ala Ser Tyr Arg Gly Lys Ser Ala Asn Glu Asp Ala Tyr Ala Leu
Thr Gly Thr Ala Leu Ser Phe Ala Ala Gly Arg Val Ala Tyr His Leu Gly Leu Gln Gly
Pro Ala Val Ser Val Asp Thr Ala Cys Ser Ser Ser Leu Val Ala Leu His Leu Ala Cys
Asp Ala Leu Arg Arg Gly Asp Cys Glu Val Ala Leu Ala Ala Gly Val Gln Val Leu Ala
Asn Pro Ala Gly Phe Val Leu Leu Ser Arg Thr Arg Ala Val Ser Pro Asp Gly Arg Cys
Lys Thr Phe Ser Gln Ala Ala Asp Gly Tyr Gly Arg Gly Glu Gly Val Gly Val Val Val
Leu Met Arg Leu Ser Asp Ala Gln Ala Gln Gly Met Arg Val Leu Gly Val Val Arg Gly
Thr Ala Val Asn Gln Asp Gly Ala Ser Ser Gly Ile Thr Ala Pro Asn Gly Thr Ala Gln
Gln Lys Val Val Arg Ala Ala Leu Arg Asn Ala Gly Leu Glu Ala Ser Ser Ile Asp Val
Val Glu Cys His Gly Thr Gly Thr Ser Leu Gly Asp Pro Ile Glu Val Gln Ala Leu Gly
Ala Val Tyr Gly Gln Gly Arg Glu Ala Thr Arg Pro Leu Arg Leu Gly Ala Val Lys Ser
Asn Ile Gly His Leu Glu Ser Ala Ala Gly Ile Ala Gly Val Cys Lys Ile Leu Ala Ala
Phe Arg His Glu Ala Leu Pro Ala Thr Leu His Ser Ser Pro Arg Asn Pro Gln Ile Ser
Trp Glu Ser Leu Pro Val Gln Val Val Asp Arg Leu Thr Gly Trp Pro Arg Arg Ala Asp
Gly Leu Pro Arg Phe Ala Gly Val Ser Ser Phe Gly Ile Ser Gly Thr Asn Ala His Val
Ile Leu Glu Glu Ala Pro Leu Glu Ala Val Arg Glu Pro Ala Ala Val Arg Glu Pro Leu
Ala Ala Glu Gly Val Ala Ile Pro Leu Leu Leu Ser Gly Arg Asp Glu Ala Ser Val Gly
Ala Gln Ala Glu Arg Trp Ala Lys Trp Leu Gly Glu His Ala Glu Val Arg Trp Pro Asp
Val Val Arg Thr Ala Ala Leu His Arg Thr His Phe Ala Trp Arg Ala Ser Val Gln Ala
Ala Ser Val Ser Glu Ala Val Glu Gly Leu Arg Ala Leu Ser Glu Gly Arg Ala Ala Ala
Gly Val Val Arg Gly Thr Gly Gly Arg Gly Gly Lys Leu Ala Val Leu Phe Thr Gly Gln
Gly Ser Gln Arg Leu Gly Met Gly Lys Arg Leu Tyr Glu Val Tyr Pro Val Phe Arg Ala
Ala Phe Asp Glu Val Cys Glu Ala Leu Asp Ala His Leu Asp Arg Gly Leu Arg Glu Val
Val Phe Ala Glu Ala Gly Ser Glu Gln Glu Ala Leu Leu Glu Arg Thr Glu Tyr Thr Gln
Pro Gly Leu Phe Ala Leu Glu Val Ala Leu Tyr Arg Gln Trp Glu Ala Trp Gly Val Arg
Pro Ala Ala Leu Leu Gly His Ser Ile Gly Glu Leu Ser Ala Ala His Val Ala Gly Val
Leu Ser Leu Ala Asp Ala Ala Lys Leu Val Cys Ala Arg Gly Arg Leu Met Gln Arg Cys
Gln Ala Gly Gly Ala Met Met Ser Val Glu Ala Ser Glu Pro Glu Val Gln Gly Ala Leu
Ser Ala Met Gly Leu Glu Gly Arg Leu Gly Ile Ala Gly Ile Asn Gly Pro Ser Gln Thr
Val Leu Ser Gly Asp Glu Ala Ala Val Leu Glu Val Gly Arg Arg Phe Glu Ala Gln Gly
Arg Arg Thr Arg Arg Leu Arg Val Ser His Ala Phe His Ser Ala His Met Asp Gly met
Leu Glu Glu Tyr Gly Arg Val Ala Arg Glu Cys Ala Tyr Gly Arg Pro Gln Val Pro Val
Val Ser Gly Val Thr Gly Glu Leu Gly Gly Glu Glu Ser Leu Met Ser Ala Glu Tyr Trp
Val Arg Gln Val Arg Glu Ala Val Arg Phe Leu Asp Gly Met Arg Thr Leu Ala Ala Ala
Gly Val Ser Thr Tyr Val Glu Cys Gly Pro Asp Gly Val Leu Cys Ala Leu Gly Ala Gly
Cys Leu Pro Glu Gly Ala Glu Ala Thr Phe Val Ala Ser Leu Arg Arg Glu Gln Glu Glu
Glu Arg Ala Leu Val Thr Ala Val Ala Thr Val His Val Gln Gly His Glu Val Asp Trp
Ala Gln Val Leu Ser Gly His Gly Gly Arg Pro Val Glu Leu Pro Thr Tyr Ala Phe Gln
Arg Gln Arg Tyr Trp Leu Glu Ala Pro Arg Ala Arg Gly Asp Val Gly Ser Ala Gly Leu
Lys Ala Ala Ala His Pro Leu Leu Gly Ala Ala Thr Lys Leu Ala Asp Gly Glu Gly His
Leu Phe Thr Gly Arg Leu Ser Leu Ala Glu His Ala Trp Leu Arg Asp His Gln Val Phe
Gly Lys Val Val Phe Pro Gly Thr Gly Met Leu Glu Leu Ala Leu Ala Ala Gly Arg Ala
Val Gly Ser Arg Thr Leu Ser Glu Leu Val Leu Ala Glu Pro Leu Val Leu Ala Glu Glu
Ala Ala Ala Arg Leu Gln Leu Ser Val Gly Ala Pro Asp Ala Ala Gly Arg Arg Glu Val
Gly Leu Tyr Ser Gln Ser Glu Gln Ala Pro Glu Asp Ala Pro Trp Val Gln His Ala Thr
Gly Val Leu Thr Asp Glu Ile Pro Gly Ala Pro Gly Glu Leu Asp Glu Leu Ser Thr Trp
Pro Val Pro Gly Ala Glu Glu Val Asp Leu Ser Gly Phe Tyr Glu Arg Leu Arg Glu Gly
Gly Leu Asp Tyr Gly Pro Val Phe Gln Gly Leu Val Glu Leu Trp Arg Arg Gly Ala Arg

FIG.3D

Contig1_orf1
Leu Tyr Gly Arg Val Val Leu Pro Gly Ser Ala Arg Gly Ser Ala Glu Ala Tyr Gly Val
His Pro Ala Leu Met Asp Ala Ala Leu His Thr Met Val Ala Ala Phe Ser Gln Met Ser
Gly Pro Asp Gly Val Leu Leu Pro Phe Ala Trp Ser Asp Val Ala Pro His Ala Thr Gly
Ala Ser Glu Leu Arg Ile Arg Val Glu Met Gln Glu Gln Ser Ala Gln Gln Pro Ala Ala
Ser Leu Tyr Val Ala Asp Cys Thr Gly Gln Val Val Ala Ser Ile Gly Ala Leu Arg Leu
Arg Arg Ala Thr Ala Glu Gln Leu Arg Thr Ala Val His Ala Gly Gly Gln His Met Tyr
Gln Val Ser Phe Gln Pro Val Asp Leu Ala Ala Pro Pro Leu Val Thr Gly Ser Leu Val
Val Ile Gly Ala Pro Lys Gly Gly Ala Arg Leu Ala Glu Ala Leu Gly Ala Glu Ala Ile
Ala Asp Leu Asp Ala Leu Val Val Arg Leu Glu His Gly Ala Ser Ala Pro Glu Arg Val
Val Val Asp Val Thr Ala Ala Ser Pro Ser Pro Leu Asp Val Ala Gly Ser Ser His Glu
Ala Thr Arg Gln Ala Leu Ser Leu Leu Gln Ala Trp Leu Ser Glu Pro Arg Leu Glu Ala
Thr Glu Leu Val Trp Ile Thr Arg Gly Ala Val Gly Ala Ala Pro Asp Asp Ala Val Glu
Asp Leu Ala Arg Ala Pro Leu Trp Gly Leu Val Arg Ala Ala Arg Ser Glu His Pro Glu
Arg Gly Leu Arg Leu Met Asp Val Gly Thr Glu Pro Val Asp Ala Gly Leu Leu Ala Arg
Ala Leu Ala Thr Ala Ala Glu Pro Glu Leu Ala Leu Arg Gly Gly Ala Ala Leu Ala Ala
Arg Leu Val Arg Ala Gln Ala Val Ala Glu Glu Leu Thr Arg Ala Arg Glu Leu Asp Pro
Ala Gly Thr Val Leu Val Thr Gly Gly Thr Gly Glu Leu Gly Gln Ala Val Ala Ala His
Leu Val Arg Ala His Gly Val Arg His Leu Val Leu Thr Ser Arg Arg Gly Leu Glu Ala
Pro Gly Ala Arg Glu Leu Val Glu Ser Leu Ala Glu Leu Gly Ala Glu Thr Val Thr Val
Ala Ala Cys Asp Val Ser Lys Arg Glu Glu Val Ala Arg Val Leu Ala Gly Ile Asp Ala
Ala Arg Pro Leu Ser Ala Val Leu His Leu Ala Gly Ala Leu Asp Asp Gly Val Leu Ala
Gly Gln Thr Ala Glu Arg Leu Ser Arg Val Leu Ala Pro Lys Val Asp Gly Ala Leu His
Leu His Glu Leu Thr Arg Glu Leu Asp Leu Val Ala Phe Val Leu Phe Ser Ser Val Ala
Gly Thr Phe Gly Thr Ala Gly Gln Ser Asn Tyr Ala Ala Ala Asn Thr Phe Leu Asp Ala
Leu Ala Ala His Arg Arg Gly Cys Gly Leu Ala Ala Thr Ser Leu Ala Trp Gly Leu Trp
Ala Gln Ala Gly Val Gly Met Thr Ala His Leu Gly Glu Ala Glu Leu Ser Arg Ile Arg
Arg Ala Gly Leu Val Pro Ile Ser Val Asp Glu Gly Leu Ala Leu Leu Asp Ala Ala Leu
Ser Arg Ser Glu Ala Ser Leu Val Pro Val His Leu Asp Leu Ala Gln Leu Gln Arg Gly
Leu Glu Ser Ser Gly Glu Leu Pro Ala Leu Leu Arg Ala Leu Val Arg Pro Gly Leu Arg
Lys Ala Ser Ser Ala Ala Arg Lys Glu Ala Ser Thr Leu Arg Glu Arg Leu Ser Ala Leu
Pro Glu Ala Glu Arg Leu Ser Ser Leu Ile Asp Leu Val Arg Ala Glu Val Ala Ala Val
Leu Gly Leu Gln Arg Gly Asp Ala Ile Pro Thr Ala Gln Pro Leu Arg Glu Leu Gly Met
Asp Ser Leu Met Ala Val Glu Val Arg Asn Arg Leu Ala Leu Leu Val Gly Ser Asn Leu
Pro Ala Thr Leu Leu Phe Asp His Pro Ser Ala Thr His Ile Ala Lys Phe Leu Leu Ser
Lys Phe Gly Asn Gly Glu Arg Arg Asn Leu Leu Arg Thr Ala Asp Ser Met Ser Asp Glu
Glu Ile Arg Ala Phe Met Leu Ser Leu Ser Val Ser Leu Val Arg Arg Ser Gly Leu Leu
Pro Lys Leu Leu Glu Leu Arg Gly Pro Ser Glu Thr Ser Val Glu Val Pro Val Pro Ile
Ser Asp Phe Glu Asp Leu Ala Asp Glu Gln Leu Ala Leu Gln Ala Leu Gln Met Ile Ser
Asn Ser Glu Asp Leu His Glu *

FIG.3E

Contig1_orf2

```
Met Asn Ser Ser Ala Ala Ser Pro Thr Leu Arg Glu Ala Leu Thr Arg Ala Leu Lys Glu
Leu Gln Arg Leu Gln Ala Ser His Ser Asp Leu Arg Ser Gly Pro Ile Ala Ile Val Ser
Met Ala Cys Arg Leu Pro Gly Gly Val Ala Thr Pro Glu Asp Tyr Trp Arg Leu Leu Glu
Glu Gly Arg Asp Ala Ile Glu Ala Phe Pro Ala Arg Trp Asp Ala Pro Ser Ile Tyr Asp
Pro Asp Pro Glu Ala Val Gly Lys Thr Tyr Val Arg Glu Gly Gly Phe Leu Arg Asp Ile
Asp Leu Phe Asp Ala Gly Phe Phe Gly Ile Ser Pro Arg Glu Ala Gln Ala Met Asp Pro
Gln Gln Arg Leu Val Leu Glu Thr Ala Trp Glu Ala Leu Glu Arg Ala Gly Val Arg Pro
Ser Ala Leu Ser Glu Ser Ser Thr Gly Val Tyr Leu Gly Ser Met Gly Ser Asp Tyr Gly
Ala Leu Tyr Gly Ser Asp Leu Ala Ala Leu Asp Gly Tyr Arg Gly Thr Gly Ser Ala Ala
Ser Val Leu Ser Gly Arg Val Ala Tyr Val Leu Gly Leu Gln Gly Pro Ala Ile Thr Val
Asp Thr Ala Cys Ser Ser Ser Leu Val Ser Leu His Leu Ala Cys Thr Ala Leu Arg Gln
Gly Glu Cys Asp Leu Ala Leu Thr Gly Gly Val Met Val Met Thr Thr Pro Ala Gly Phe
Val Glu Phe Ser Arg Leu Lys Ala Leu Ala Arg Asp Gly Arg Cys Lys Ser Phe Ser Ala
Arg Ala Asp Gly Val Ile Trp Ser Glu Gly Cys Gly Met Leu Val Leu Lys Arg Leu Ser
Asp Ala Arg Arg Asp Gly Asp Arg Val Leu Ala Val Ile Arg Gly Ser Ala Val Asn Gln
Asp Gly Arg Ser Gln Gly Leu Thr Ala Pro Asn Gly Pro Ala Gln Gln Arg Val Ile Gln
Gln Ala Leu Ser Ser Cys Arg Leu Ser Pro Glu Asp Ile Asp Ala Val Glu Ala His Gly
Thr Gly Thr Asn Leu Gly Asp Pro Ile Glu Ala Gly Ala Leu Val Glu Val Phe Gly Pro
Gly Arg Lys Ala Glu Arg Pro Leu Tyr Leu Gly Ser-Ser Lys Ser Asn Leu Gly His Ala
Gly Pro Ala Ala Gly Val Ala Gly Val Leu Lys Met Val Leu Ser Met Gln His Glu Val
Leu Pro Arg Thr Leu His Ala Glu Gln Pro Ser Pro His Ile Gly Trp Glu Gly Ser Gly
Leu Ser Leu Leu Gln Glu Ala Arg Pro Trp Arg Arg Asn Gly Arg Ala Arg Arg Ala Gly
Val Ser Ser Phe Gly Ile Ser Gly Thr Asn Ala His Val Ile Leu Glu Glu Ala Pro Val
Glu Ala Ala Arg Glu Pro Val Glu Ala Met Arg Glu Pro Leu Ala Thr Glu Gly Val Ala
Met Pro Leu Leu Leu Ser Gly Arg Asp Glu Ala Ser Val Gly Ala Gln Ala Glu Arg Trp
Ala Lys Trp Leu Gly Glu His Gly Glu Val Gln Trp Ser Asp Val Val Arg Thr Ala Ala
Leu His Arg Thr His Phe Ala Ser Arg Ala Ser Val Leu Ala Ala Ser Val Ser Glu Ala
Glu Glu Ala Leu Arg Ala Leu Ser Gln Gly Arg Gly His Arg Ala Val Ser Ala Gly Thr
Ala Arg Ala Arg Gly Lys Val Val Phe Val Phe Pro Gly Gln Gly Ser Gln Trp Pro Gly
Met Gly Arg Ala Leu Leu Glu Gln Ser Ala Ala Phe Ala Glu Ala Val Gln Ala Cys Asp
Glu Ala Leu Arg Pro Trp Thr Gly Trp Ser Val Leu Ser Val Leu Arg Gly Asp Gly Gly
Glu Glu Gln Pro Ser Leu Glu Arg Val Asp Val Val Gln Pro Ala Leu Phe Ala Met Cys
Val Gly Leu Ala Ala Ala Trp Arg Ser Leu Gly Leu Glu Pro Ala Ala Val Val Gly His
Ser Gln Gly Glu Val Ser Ala Ala Val Val Cys Gly Ala Leu Ser Leu Ala Glu Gly Ala
Arg Val Val Ala Leu Arg Ser Gln Ala Val Arg Gln Arg Ser Gly Met Gly Ala Met Met
Leu Val Glu Arg Pro Val Ser Glu Val Gln Glu Arg Ile Ala Pro Tyr Gly Glu Ala Leu
Ala Ile Ala Ala Val Asn Thr Ser Ser Ser Thr Val Val Ser Gly Asp Val Glu Ala Val
Asp Gly Leu Met Val Glu Leu Thr Ala Glu Gly Val Phe Cys Arg Lys Val Asn Val Asp
Tyr Ala Ser His Ser Ala His Met Asp Ala Leu Leu Pro Glu Leu Gly Ala Lys Leu Ser
Ser Leu Arg Pro Lys Ala Thr Gln Leu Pro Phe Tyr Ser Thr Val Thr Gly Glu Val Ser
Arg Gly Glu Ala Leu Asp Gly Glu Tyr Trp Cys Arg Asn Leu Arg Arg Thr Val Arg Leu
Asp Arg Ala Leu Ser Lys Leu Leu Glu Asp Gly His Gly Val Phe Val Glu Val Ser Ala
His Pro Val Leu Ala Met Pro Leu Thr Thr Ala Cys Gly Glu Ala Gln Gly Val Val Val
Gly Ser Leu Gln Arg Asp Glu Gly Gly Leu Ser Gln Leu Tyr Arg Thr Leu Gly Gln Leu
His Val Gln Gly His Glu Val Asp Trp Thr Arg Val Leu Ser Gly His Gly Arg Val
Val Glu Leu Pro Thr Tyr Ala Phe Gln Arg Gln Arg Tyr Trp Leu Asp Ile Ser Lys Ala
Arg Ser Asp Val Ser Ser Ala Gly Leu Lys Ala Ala Ala His Pro Leu Leu Gly Ala Ala
Thr Arg Leu Ala Asp Gly Glu Gly His Leu Phe Thr Gly Arg Leu Ser Leu Ala Glu His
Pro Trp Leu Arg Asp His Glu Val Phe Gly Gln Val Val Leu Pro Gly Thr Gly Thr Leu
Glu Leu Val Leu Ala Ala Gly Arg Ala Val Gly Ser Arg Ser Leu Ser Glu Leu Thr Leu
Ala Glu Pro Leu Val Leu Ala Glu Gly Ala Ala Arg Leu Gln Val Met Ile Gly Ala Pro
Asp Ala Ala Gly Arg Arg Glu Val Gly Leu Tyr Ser Gln Pro Glu Gln Ala Pro Glu Asp
Ala Pro Trp Val Gln His Ala Thr Gly Val Leu Thr Asp Glu Pro Pro Gly Ile Pro Val
Glu Leu Asp Glu Leu Ser Thr Trp Pro Val Pro Gly Ala Glu Glu Val Asp Leu Ser Gly
```

FIG.4A

```
Contig1_orf2
Leu Tyr Glu Arg Leu Arg Glu Arg Gly Leu His Tyr Gly Pro Ala Phe Gln Gly Leu Val
Glu Leu Ser Arg Gln Gly Thr Thr Tyr Phe Gly Arg Val Val Leu Pro Gly Thr Glu Lys
Asp Arg Ala Glu Ala Tyr Gly Val His Pro Ala Leu Met Asp Ala Ala Leu His Thr Met
Val Ala Ala Phe Ser Glu Ser Pro Gly Ala Asn Glu Val Leu Val Pro Phe Ala Trp Ser
Asp Val Ala Leu His Ala Thr Gly Ala Ser Glu Leu Arg Val Arg Val Glu Leu Gln Asp
Gly Gly Ala His Gln Asp Thr Ala Ser Leu Gln Val Ala Asp Ser Thr Gly Gln Ala Val
Ala Ser Ile Gly Ala Leu His Leu Arg Arg Ala Thr Ala Glu Gln Leu Arg Thr Ala Val
His Ala Gly Gly Gln His Met Tyr Gln Val Ser Phe Gln Pro Val Glu Leu Ala Ala Ala
Pro Leu Glu Ala Gly Ser Leu Val Val Val Gly Ala Ala Glu Gly Arg Gly Arg Leu Ala
Glu Ala Leu Arg Ala Glu Ala Ile Ala Asp Leu Glu Ala Leu Val Ala Arg Leu Glu Gln
Gly Ala Ser Ala Pro Ala Arg Val Ala Val Asp Thr Thr Ala Leu Gly Gln Ser Gln Ser
Gly Val Ala Ser Leu Ser His Glu Ala Thr Arg Gln Ala Leu Ser Leu Leu Gln Ala Trp
Leu Ser Glu Pro Arg Leu Asp Ala Val Glu Leu Val Trp Val Thr Arg Gly Ala Val Gly
Ala Ala Pro Asp Asp Ala Val Gln Asp Leu Ala Arg Ala Pro Leu Trp Gly Leu Val Arg
Ala Ala Arg Ser Glu His Pro Glu Arg Arg Leu Arg Leu Ile Asp Val Gly Thr Glu Pro
Val Asp Ala Gly Leu Leu Ala Arg Ala Leu Ala Thr Ala Ala Glu Pro Glu Leu Ala Leu
Arg Gly Gly Ala Ala Leu Ala Ala Arg Leu Val Arg Ala Gln Ala Ala Ala Glu Glu Leu
Thr Arg Gly Ala Arg Glu Leu Asp Pro Ala Gly Thr Val Leu Val Thr Gly Gly Thr Gly
Glu Leu Gly Gln Ala Ile Ala Ala His Leu Val Arg Ala His Gly Val Arg His Leu Val
Leu Thr Ser Arg Arg Gly Leu Glu Ala Pro Gly Ala Arg Glu Leu Val Gln Ser Leu Glu
Glu Leu Gly Ala Glu Thr Val Thr Val Ala Ala Cys Asp Val Ser Lys Arg Glu Glu Val
Ala Arg Val Leu Ala Gly Ile Asp Ala Ala Arg Pro Leu Ser Ala Val Leu His Leu Ala
Gly Val Leu Asp Asp Gly Val Leu Thr Ala Gln Thr Ala Glu Arg Leu Ser Arg Val Leu
Ala Pro Lys Val Asp Gly Ala Leu His Leu His Glu Leu Thr Arg Glu Leu Asp Leu Ala
Ala Phe Val Leu Phe Ser Ser Ala Ala Gly Thr Phe Gly Ala Ala Gly Gln Ser Asn Tyr
Ala Ala Ala Asn Thr Phe Leu Asp Ala Leu Ala Ala His Arg Arg Gly Gly Gly Leu Ala
Ala Thr Ser Leu Ala Trp Gly Phe Trp Thr Gln Ala Gly Val Gly Met Thr Ala His Leu
Gly Glu Ala Glu Leu Ser Arg Met Arg Arg Asn Gly Phe Val Pro Met Pro Val Glu Glu
Gly Leu Ala Leu Leu Asp Ala Ala Leu Ser Arg Pro Glu Ala Ser Leu Val Pro Val His
Leu Asp Leu Ala Gln Leu Gln Arg Gly Leu Glu Ser Ser Gly Glu Leu Pro Ala Leu Phe
Arg Ala Leu Leu Arg Pro Ser Leu Arg Lys Ala Ser Ser Ala Thr Arg Arg Asp Ala Ser
Ala Leu Arg Glu Arg Leu Ser Ala Leu Pro Glu Ala Glu Arg Leu Asn Ala Leu Val Glu
Leu Val Arg Gly Glu Val Ala Ala Val Ala Gly Leu Gln Arg Gly Glu Ala Val Ala Ala
Asp Gln Val Leu Lys Glu Leu Gly Leu Asp Ser Leu Met Ala Val Ala Leu Arg Asn Arg
Leu Thr Ser Arg Thr Glu Thr Ser Leu Pro Ala Thr Leu Val Phe Asp Tyr Pro Thr Pro
Arg Ala Ile Ala Glu Leu Leu Leu Lys Gln Ala Phe Ser Gly Leu Gln Val Lys Glu Ala
Arg Ala Arg Val Arg Arg Arg Ala Gly Lys Asp Glu Pro Ile Ala Ile Val Ser Met Ala
Cys Arg Leu Pro Gly Gly Val Ala Thr Pro Asp Asp Tyr Trp Arg Leu Leu Ala Glu Gly
Lys Asp Ala Ile Glu Gly Leu Pro Ala Arg Trp Asp Gly Phe Glu Val Tyr Asp Pro Asp
Pro Glu Ala Ala Gly Lys Ser Tyr Ala Arg Glu Gly Gly Phe Val Arg Asp Ile Asp Leu
Phe Asp Ala Asn Phe Phe Gly Ile Ser Pro Arg Glu Ala Gln Ser Met Asp Pro Gln His
Arg Leu Val Leu Glu Thr Ala Trp Glu Ala Leu Glu Arg Ala Gly Val Arg Pro Ser Ala
Leu Ser Gly Ser Ala Thr Gly Val Tyr Leu Gly Ser Met Gly Ser Asp Tyr Gly Ala Leu
His Thr Val Asp Leu Lys Glu Leu Asp Gly Tyr Arg Gly Ile Gly Ser Ala Ala Ser Ile
Leu Ser Gly Arg Val Ala Tyr Ala Leu Gly Leu Gln Gly Pro Ala Met Thr Val Asp Thr
Ala Cys Ser Ser Ser Leu Val Ser Leu His Leu Ala Cys Thr Ala Leu Arg Gln Gly Glu
Cys Asp Leu Ala Leu Ala Gly Gly Val Thr Val Met Ser Thr Pro Ala Leu Phe Val Glu
Phe Ser Arg Leu Lys Gly Met Ser Arg Asp Gly Arg Cys Lys Ser Phe Ser Val Gln Ala
Asp Gly Ala Gly Trp Ala Glu Gly Cys Gly Met Leu Leu Leu Lys Arg Leu Ser Asp Ala
Gln Arg Asp Gly Asp Arg Val Leu Gly Val Ile Arg Gly Ser Ala Val Asn Gln Asp Gly
Arg Ser Gln Gly Leu Thr Ala Pro Asn Gly Pro Ala Gln Gln Arg Val Ile Arg Gln Ala
Leu Ser Ser Cys Gly Leu Ser Pro Glu Asp Ile Asp Ala Val Glu Ala His Gly Thr Gly
Thr Ser Leu Gly Asp Pro Ile Glu Ala Gly Ala Leu Ala Glu Val Phe Gly Pro Glu Arg
Ser Pro Glu Arg Pro Leu Tyr Leu Gly Ser Ser Lys Ser Asn Leu Gly His Ala Gln Ala
```

FIG.4B

Contig1_orf2

Ala Ala Gly Val Ala Gly Val Ile Lys Met Val Leu Ser Met Gln His Glu Val Leu Pro
Lys Thr Leu His Ala Glu Gln Pro Ser Pro His Ile Gly Trp Glu Gly Ser Gly Leu Ser
Leu Leu Gln Glu Ala Arg Pro Trp Arg Arg Asn Gly Arg Val Arg Arg Ala Gly Val Ser
Ser Phe Gly Ile Ser Gly Thr Asn Ala His Ile Ile Leu Glu Glu Ala Pro Ala Glu Ala
Arg Arg Glu Pro Val Glu Ala Ala Ala Pro Ala Leu Leu Pro Leu Val Leu Ser Gly
Arg Asp Glu Ala Ala Val Asn Ala Gln Ala Gly Arg Trp Ala Lys Trp Leu Glu Glu His
Gly Glu Val Gly Trp Ser Asp Val Val Arg Thr Ala Ala Leu His Arg Thr His Phe Glu
Ser Arg Ala Ser Val Leu Ala Ala Ser Ala Ala Gly Ala Val Glu Gly Leu Arg Ala Leu
Ser Ser Gly Arg Pro Asp Ala Ala Val Val Ser Gly Thr Ala Lys Arg Gly Gly Lys Leu
Ala Val Leu Phe Thr Gly Gln Gly Ser Gln Arg Leu Gly Met Gly Lys Arg Leu Tyr Glu
Val Tyr Pro Val Phe Arg Ala Ala Phe Asp Glu Val Cys Glu Ala Leu Asp Ala Tyr Leu
Asp Arg Gly Leu Arg Glu Val Val Phe Ala Ala Ala Gly Ser Glu Gly Gly Ala Leu Leu
Glu Arg Thr Glu Tyr Thr Gln Pro Gly Leu Phe Ala Leu Glu Val Ala Leu Tyr Arg Gln
Trp Glu Ser Trp Gly Leu Lys Pro Ala Ala Leu Leu Gly His Ser Ile Gly Glu Leu Ser
Ala Ala His Val Ala Gly Val Leu Ser Leu Ala Asp Ala Ala Lys Leu Val Cys Ala Arg
Gly Arg Leu Met Gln Gly Cys Glu Ala Gly Gly Ala Met Val Ser Val Glu Ala Ser Glu
Pro Glu Val Gln Arg Ala Leu Ser Glu Val Gly Ala Gln Gly Arg Leu Ser Ile Ala Gly
Leu Asn Ala Pro Met Gln Thr Val Leu Ser Gly Asp Glu Ala Ala Val Leu Ala Val Ala
Arg Arg Leu Glu Ala Gln Gly Arg Arg Thr Arg Arg Leu Arg Val Ser His Ala Phe His
Ser Ala His Met Asp Gly Met Leu Glu Glu Phe Gly Lys Val Ala Arg Glu Cys Thr Tyr
Ala Arg Pro Arg Leu Ala Val Val Ser Gly Val Thr Gly Glu Leu Gly Gly Glu Glu Ala
Leu Met Ser Ala Glu Tyr Trp Val Arg Gln Val Arg Glu Ala Val Arg Phe Leu Asp Gly
Met Arg Thr Leu Ala Ala Ala Gly Val Ser Thr Tyr Val Glu Cys Gly Pro Asp Gly Val
Leu Cys Ala Leu Gly Ala Gly Cys Leu Pro Glu Gly Ala Glu Ala Thr Phe Val Thr Ser
Leu Arg Arg Glu Gln Glu Glu Glu Arg Ala Leu Ala Thr Ala Val Ala Thr Val His Val
Gln Gly His Glu Val Asp Trp Ala Arg Val Leu Ser Gly Arg Gly Gly Arg Pro Val Glu
Leu Pro Thr Tyr Ala Phe Gln Arg Gln Arg Tyr Trp Leu Glu Ala Pro Lys Ser Ala Ala
Thr Glu Val Asn Val Ser Ser Ala Glu Gln Ala Leu Trp Asn Ala Ala Leu Glu Gly Glu
Gly Asp Gly Val Ala Glu Leu Leu Glu Leu Pro Asp Asp Val Arg Ala Ser Val Gly Pro
Leu Leu Pro Tyr Leu Ala Ala Trp Arg Gln Arg Lys Gln Ala Glu Ala Ala Ala Ala Ser
Trp Leu Tyr Glu Glu Ala Trp Gln Asn Arg Pro Arg Arg Val Thr Gly Ser Pro Asp Val
Arg Gly Thr Trp Leu Val Val Ser Pro Pro Leu Ala Gly Glu Leu Ala Glu Val Val Arg
Gly Ala Leu Gly Ala Ala Gly Ala Glu Val Ile Val His Ile Ala Ala Val Glu Arg Ala
Gln Leu Ala Ala Trp Leu Arg Glu Gln Ala Arg Leu Arg Lys Glu Gly Gly Glu Leu Arg
Gly Val Ile Ala Leu Thr Ala Ser Gly Glu Glu Gly Ala Leu Glu Gln Gly Gln Ala Pro
Arg Ser Leu Tyr Gln Thr Leu Ala Val Val Gln Ala Leu Gly Asp Ala Gly Ile Gly Ala
Arg Leu Trp Leu Leu Thr Gln Gly Ala Val Ser Thr Glu Pro Ser Glu Ala Val Val His
Pro Leu Gln Ala Leu Thr Trp Gly Leu Gly Arg Ala Leu Gly Leu Glu His Pro Glu Arg
Trp Gly Gly Leu Leu Asp Val Pro Ala Glu Leu Asp Ala Gly Val Met Gln His Val Leu
Thr Thr Leu Val Ser Asp Asp Asn Glu Asp Gln Val Ala Val Arg Arg Gly Gly Arg Leu
Val Arg Arg Ile Val Arg Val Arg Gly Glu Gly Asp Gly Glu Gly Trp Lys Pro Arg Gly
Thr Val Leu Ile Thr Gly Gly Val Gly Gly Leu Gly Gly His Leu Ala Arg Trp Leu Ala
Gly Arg Gly Ala Glu His Leu Val Leu Ala Ser Arg Arg Gly Ala Ser Ala Pro Gly Ala
Ser Glu Leu Arg Asp Glu Leu Val Ala Arg Gly Ile Arg Val Thr Leu Ala Ala Cys Asp
Val Ser Glu Arg Ala Gln Leu Ala Ala Leu Leu Ala Glu Leu Glu Gln Asp Glu Ala Pro
Leu Arg Ala Val Ala His Leu Ala Gly Ile Gly Arg Arg Val Pro Leu Arg Glu Leu Glu
Pro Glu Gln Leu Glu Gln Glu Leu Ala Ala Lys Val Lys Gly Ala Trp His Leu His Gln
Leu Leu Gly Lys Arg Glu Leu Asp Ala Phe Val Leu Tyr Gly Ser Ile Ala Gly Leu Trp
Gly Ser Gly Ala Gln Ala Gly Tyr Gly Ala Ala Asn Ala Gly Leu Asp Ala Leu Ala Arg
Tyr Arg Arg Ala Arg Gly Gln Ala Ala Thr Val Leu His Trp Gly Pro Trp Ala Gly Glu
Gly Met Val Thr Ser Glu Leu Glu Ser Gln Leu Arg Ile Arg Gly Val Ala Val Met Ser
Pro Asp Lys Ala Leu Ala Gly Leu Glu Met Ala Leu Arg Leu Gly Arg Thr Ser Val Ala
Ile Ala Asp Val Asp Trp Ser Arg Phe Ala Pro Ser Phe Ser Ala Ala Arg Pro Arg Pro
Leu Leu Asp Gly Ile Glu Glu Ala Arg Arg Ala Gln Glu Ser Arg Gly Pro Gln Pro Ala

FIG.4C

Contig1_orf2

Ala Gly Gly Thr Ala Leu Arg Asp Thr Leu Leu Gly Leu Ser Glu Ala Glu Arg Arg Glu
Arg Val Arg Gln Leu Val Ala Ser Glu Thr Ala Ala Val Leu Gly Met Thr Asp Pro Ser
Arg Leu Asp Pro Asp Arg Gly Phe Leu Asp Leu Gly Leu Asp Ser Leu Met Ala Val Glu
Leu Ser Lys Arg Leu Gln Lys Arg Thr Gly Met Thr Val Pro Ser Thr Leu Ser Phe Asp
His Pro Thr Gln Ser Asp Val Ala Arg Trp Leu Leu Glu Gln Leu Thr Pro Gln Pro Arg
Pro Glu Pro Ala Val Arg Glu Val Ser Arg Glu Glu Gly Trp Ser Thr Pro Ile Ala Ile
Val Gly Val Gly Leu Arg Met Pro Gly Gly Ala Ser Asp Leu Glu Ser Phe Trp Gln Val
Leu Val Glu Glu Arg Asp Thr Leu Arg Pro Ile Pro Ala Gln Arg Phe Asp Val Glu Ala
Leu Tyr Asp Pro Asp Pro Asp Ala Lys Gly Lys Thr Tyr Val Arg Asn Ala Ser Leu Leu
Asp Asp Val Ala Ser Phe Asp Pro Gly Phe Phe Gly Ile Ser Pro Arg Glu Ala Glu Pro
Met Asp Pro Gln His Arg Leu Leu Leu Glu Thr Ala Trp Ser Ala Leu Glu Asp Ala Gly
Val Arg Pro Glu His Leu Lys Gly Ser Asp Thr Gly Val Phe Val Gly Val Ala Pro Ser
Glu Tyr Ala Ser Tyr Arg Gly Lys Ser Ala Asn Glu Asp Ala Tyr Ala Leu Thr Gly Thr
Ala Leu Ser Phe Ala Ala Gly Arg Val Ala Tyr His Leu Gly Leu Gln Gly Pro Ala Val
Ser Thr Asp Thr Ala Cys Ser Ser Ser Leu Val Ala Val His Leu Ala Cys Asp Ala Leu
Arg Arg Gly Asp 6ys Glu Val Ala Leu Ala Ala Gly Val Gln Val Leu Ala Asn Pro Ala
Gly Phe Val Leu Leu Ser Arg Thr Arg Ala Leu Ser Pro Asp Gly Arg Cys Lys Ala Phe
Ser Gln Ala Ala Asp Gly Tyr Gly Arg Gly Glu Gly Val Gly Val Leu Val Leu Met Arg
Leu Ser Glu Ala Gln Gln Gln Gly Lys Arg Val Leu Gly Val Val Arg Gly Thr Ala Val
Asn Gln Asp Gly Ala Ser Ser Gly Ile Thr Ala Pro Asn Gly Thr Ala Gln Gln Lys Val
Val Arg Ala Ala Leu Arg Asn Ala Gly Leu Glu Pro Ala Ser Ile Asp Val Val Glu Cys
His Gly Thr Gly Thr Ser Leu Gly Asp Pro Ile Glu Val Gln Ala Leu Gly Ala Val Tyr
Gly Gln Gly Arg Asp Met Ala Arg Pro Leu Gln Leu Gly Ala Val Lys Ser Asn Ile Gly
His Leu Glu Ser Ala Ala Gly Ile Ala Gly Val Cys Lys Ile Leu Ala Ala Phe Arg Tyr
Glu Ser Leu Pro Ala Thr Leu His Ser Ser Pro Arg Asn Pro Arg Ile Pro Trp Glu Asn
Leu Pro Val Gln Val Val Asp Arg Leu Thr Pro Trp Pro Arg Arg Ala Glu Gly Pro Pro
Arg Arg Ala Gly Val Ser Ser Phe Gly Ile Ser Gly Thr Asn Ala His Val Ile Leu Glu
Glu Ala Pro Ala Glu Ala Arg Arg Glu Pro Val Glu Ala Glu Ala Ala Pro Ala Leu Leu
Pro Leu Val Leu Ser Gly Arg Asp Glu Ala Ala Val Asn Ala Gln Ala Gly Arg Trp Ala
Lys Trp Leu Glu Glu His Gly Glu Val Gly Trp Ser Asp Val Val Arg Thr Ala Ala Leu
His Arg Thr His Phe Glu Ser Arg Ala Ser Val Leu Ala Ala Ser Ala Ala Gly Ala Val
Glu Gly Leu Arg Ala Leu Ser Ser Gly Arg Pro Asp Ala Ala Val Val Ser Gly Thr Ala
Lys Arg Gly Gly Lys Leu Ala Val Leu Phe Thr Gly Gln Gly Ser Gln Arg Leu Gly Met
Gly Lys Arg Leu Tyr Glu Val Tyr Pro Val Phe Arg Ala Ala Phe Asp Glu Val Cys Glu
Ala Leu Asp Ala His Leu Asp Arg Gly Leu Arg Glu Val Val Phe Ala Ala Ala Gly Ser
Glu Glu Gly Ala Gln Leu Glu Arg Thr Glu Tyr Thr Gln Pro Gly Leu Phe Ala Leu Glu
Val Ala Leu Tyr Arg Gln Trp Glu Ser Trp Gly Leu Lys Pro Ala Ala Leu Leu Gly His
Ser Ile Gly Glu Leu Ser Ala Ala His Val Ala Gly Val Leu Ser Leu Ala Asp Ala Ala
Lys Leu Val Cys Ala Arg Gly Arg Leu Met Gln Gly Cys Glu Ala Gly Gly Ala Met Val
Ser Val Glu Ala Ser Glu Pro Glu Val Gln Arg Ala Leu Ser Glu Val Gly Ala Gln Gly
Arg Leu Ser Ile Ala Gly Leu Asn Ala Pro Met Gln Thr Val Leu Ser Gly Asp Glu Ala
Ala Val Leu Ala Val Ala Arg Arg Leu Glu Ala Gln Gly Arg Arg Thr Arg Arg Leu Arg
Val Ser His Ala Phe His Ser Ala His Met Asp Gly Met Leu Glu Glu Phe Gly Lys Val
Ala Arg Glu Cys Thr Tyr Ala Arg Pro Gln Leu Ala Val Val Ser Gly Val Thr Gly Glu
Leu Gly Gly Glu Glu Ala Leu Met Ser Ala Glu Tyr Trp Val Arg Gln Val Arg Glu Ala
Val Arg Phe Leu Asp Gly Met Arg Thr Leu Ala Ala Ala Gly Val Ser Thr Tyr Val Glu
Cys Gly Pro Asp Gly Val Leu Cys Ala Leu Gly Ala Gly Cys Leu Pro Glu Gly Ala Glu
Ala Thr Phe Val Ala Ser Leu Arg Arg Glu Gln Glu Glu Glu Arg Ala Leu Ala Thr Ala
Val Ala Thr Val His Val Gln Gly His Glu Val Asp Trp Ala Gln Val Leu Ser Gly Arg
Gly Gly Arg Pro Val Glu Leu Pro Thr Tyr Ala Phe Gln Arg Gln Arg Tyr Trp Leu Glu
Ala Pro Lys Ala Arg Thr Asp Val Gly Ser Ala Gly Leu Arg Glu Ser Gly His Pro Leu
Leu Gly Ala Ala Thr Lys Leu Ala Asp Gly Asp Gly His Leu Phe Thr Gly Arg Leu Ser
Leu Gly Glu Gln Pro Trp Leu Arg Asp His Ala Val Phe Gly Glu Val Val Phe Pro Gly
Thr Gly Met Leu Asp Leu Ala Leu Ala Ala Gly Arg Thr Val Gly Ser Gly Ala Leu Ser

FIG.4D

Contig1_orf2

Glu Leu Thr Ile Ser Glu Pro Leu Met Leu Ala Glu Asp Val Ala Val Arg Leu Gln Leu
Ser Val Gly Ala Pro Asp Ala Ala Gly Arg Arg Ala Phe Gly Leu Tyr Ser Gln Pro Glu
Gln Gly Pro Gly Asp Ala Pro Trp Val Gln His Ala Thr Gly Val Leu Thr Asp Glu Thr
Leu Ala Thr Ser Gly Glu Leu Asp Glu Leu Thr Thr Trp Pro Val Pro Gly Ala Glu Ala
Val Asp Leu Ser Gly Phe Tyr Glu Arg Leu His Glu Arg Gly Leu Arg Tyr Gly Pro Ala
Phe Gln Gly Leu Val Glu Leu Ser Arg Arg Asp Ala Thr Phe Phe Gly Arg Val Val Leu
Pro Lys Asp Ala Thr Asp Ser Ala Glu Asp Tyr Gly Val His Pro Ala Leu Met Asp Ala
Ala Leu His Thr Met Val Ala Ala Phe Ala Glu Val Ser Ala Pro Asp Asp Val Leu Leu
Pro Phe Ser Trp Ser Asp Val Ala Leu His Ala Thr Gly Ala Ser Glu Leu Arg Val Arg
Leu Glu Leu Ala Gly Gly Arg Asp Ser Ala Gln Ala Ala Ala Ser Leu Arg Val Thr Asp
Ala Ala Gly Gln Pro Val Val Ser Val Gly Ala Leu His Leu Arg Arg Ala Thr Ala Glu
Gln Leu Arg Ala Ala Thr His Ala Glu Ala Gln His Leu Tyr Arg Val Asp Phe Gln Leu
Val Ser Leu Val Glu Ala Gly Ser Lys Val Asp Ser Leu Val Val Leu Arg Ala Pro Glu
Gly Arg Gly Arg Leu Gly Glu Ala Leu Gly Val Glu Ala Ile Ala Gly Leu Asp Ala Leu
Leu Ala Arg Ile Glu Gln Gly Thr Arg Leu Pro Glu Arg Val Leu Val Asp Met Thr Ala
Gly Ser Ser Gln Arg Ser Asp Met Val Ile Ser Ser His Glu Ala Thr Gly Gln Ala Leu
Ser Leu Leu Gln Ala Trp Leu Ser Glu Pro Arg Leu Glu Gly Val Glu Leu Val Trp Val
Thr Arg Asp Ala Val Ser Ala Ala Pro Gly Asp Gly Val Gln Asp Leu Ala His Ala Pro
Leu Trp Gly Leu Val Arg Thr Ala Arg Ser Glu His Pro Glu Arg Arg Leu Arg Leu Ile
Asp Val Gly Thr Glu Pro Leu Asp Gly Gly Leu Leu Ala Arg Ala Leu Ala Thr Ala Thr
Glu Pro Glu Leu Ala Leu Arg Gly Gly Ala Ala Met Ala Ala Arg Leu Val Arg Val Pro
Ala Ala Ala Glu Gly Leu Thr Pro Ala Arg Gly Leu Asp Pro Thr Gly Thr Val Leu Val
Thr Gly Gly Thr Gly Glu Leu Gly Gln Ala Val Ala Glu His Leu Val Arg Ala His Gly
Val Arg His Leu Val Leu Thr Ser Arg Arg Gly Leu Glu Ala Pro Gly Ala Pro Gly Phe
Val Gln Ala Leu Glu Lys Leu Gly Ala Glu Thr Val Thr Val Ala Ala Cys Asp Val Ser
Lys Arg Glu Glu Val Ala Arg Val Leu Ala Gly Ile Glu Ala Ala His Pro Leu Thr Ala
Val Leu His Leu Ala Gly Val Leu Asp Asp Gly Val Ile Thr Ala Gln Thr Pro Glu Arg
Leu Ser Arg Val Leu Ala Pro Lys Val Asn Gly Ala Leu His Leu His Glu Leu Thr Glu
Asp Leu Asp Leu Ser Ala Phe Val Leu Phe Ser Ser Met Ser Gly Thr Leu Gly Thr Ala
Gly Gln Ser Asn Tyr Ala Ala Asn Ser Phe Leu Asp Ala Phe Ala Ala His Arg Arg
Ser Arg Gly Leu Ala Ala Thr Ser Leu Ala Trp Gly Phe Trp Ala Gln Thr Gly Val Gly
Met Thr Ala His Leu Gly Glu Ala Glu Leu Ser Arg Ile Gln Arg Ala Gly Leu Val Pro
Ile Arg Val Glu Glu Gly Leu Ser Leu Leu Asp Ala Ala Leu Leu Arg Pro Glu Ala Ser
Leu Val Pro Ala His Leu Asp Leu Ala Gln Met Gln Arg Gly Leu Glu Ala Ser Gly Glu
Leu Pro Ala Leu Leu Arg Ala Leu Leu Arg Pro Gly.Leu Arg Lys Ala Ser Ser Ala Thr
Arg Lys Glu Ala Ser Ala Leu Arg Glu Arg Leu Ser Glu Leu Pro Glu Ala Glu Arg Leu
Ser Ser Leu Val Glu Leu Val Arg Ala Glu Val Ala Ala Val Leu Gly Leu Pro Arg Ser
Glu Ala Val Ala Val Asp Gln Val Leu Lys Asp Leu Gly Leu Asp Ser Leu Met Ala Val
Glu Leu Arg Ser Arg Leu Ser Ala Arg Ala Glu Ile Pro Leu Pro Ala Thr Leu Val Phe
Asp Tyr Pro Thr Pro Arg Ala Val Ala Glu Leu Leu Leu Arg Gln Ala Phe Ser Lys Gln
Gln Val Thr Ala Ala Arg Ala Arg Arg Arg Thr Lys Glu Asp Glu Ala Ile Ala Ile Val
Ser Met Ala Cys Arg Leu Pro Gly Gly Val Ala Thr Pro Glu Asp Tyr Trp Arg Leu Leu
Ala Glu Gly Lys Asp Ala Ile Glu Arg Phe Pro Ser Arg Tyr Asp Ala Phe Ser Val Tyr
Asp Pro Asp Pro Glu Ala Val Gly Lys Ser Tyr Val Arg Glu Gly Gly Phe Leu Arg Asp
Ile Asp Val Phe Asp Ala Gly Phe Phe Gly Ile Ser Pro Arg Glu Ala Gln Ala Met Asp
Pro Gln Gln Arg Leu Val Leu Glu Thr Ala Trp Glu Ala Leu Glu Arg Ala Gly Val Arg
Pro Ser Met Leu Ser Glu Ser Ala Thr Gly Val Tyr Leu Gly Trp Met Gly Ser Asp Tyr
Gly Ala Leu Leu Gly Asn Asp Leu Ala Ala Leu Asp Gly Tyr Gln Gly Thr Gly Ser Ala
Ala Ser Val Leu Ser Gly Arg Val Ala Tyr Val Leu Gly Leu Gln Gly Pro Ala Ile Thr
Val Asp Thr Ala Cys Ser Ser Ser Leu Val Ser Leu His Leu Ala Cys Thr Ala Leu Arg
Gln Gly Glu Cys Asp Leu Ala Leu Thr Gly Gly Val Met Val Met Thr Thr Pro Ala Gly
Phe Val Glu Phe Ser Arg Ala Arg Gly Leu Ala Arg Asp Gly Arg Cys Lys Ser Phe Ser
Ala Gln Ala Asp Gly Val Ile Trp Ser Glu Gly Cys Gly Met Leu Leu Leu Lys Arg Leu
Ser Asp Ala Arg Arg Asp Gly Asp Arg Val Leu Gly Val Ile Arg Gly Ser Ala Val Asn

FIG.4E

Contig1_orf2
Gln Asp Gly Arg Ser Gln Gly Leu Thr Ala Pro Asn Gly Pro Ala Gln Gln Arg Val Ile
Arg Gln Ala Leu Ser Ser Cys Gly Leu Ser Pro Glu Asp Ile Asp Ala Val Glu Ala His
Gly Thr Gly Thr Ser Leu Gly Asp Pro Ile Glu Ala Gly Ala Leu Ala Glu Val Phe Gly
Pro Glu Arg Ser Pro Glu Arg Pro Leu Tyr Leu Gly Ser Ser Lys Ser Asn Leu Gly His
Ala Gln Ala Ala Ala Gly Val Ala Gly Val Ile Lys Met Val Leu Ala Leu Gln His Glu
Val Leu Pro Lys Thr Leu His Ala Glu Gln Pro Ser Pro His Ile Ala Trp Glu Gly Ser
Gly Leu Ser Leu Leu Gln Glu Ala Arg Pro Trp Arg Arg Asn Gly Arg Val Arg Arg Ala
Gly Val Ser Ser Phe Gly Ile Ser Gly Thr Asn Ala His Ile Ile Leu Glu Glu Ala Pro
Ala Glu Ala Arg Arg Glu Pro Val Glu Ala Glu Ala Ala Pro Ala Leu Leu Pro Leu Val
Leu Ser Gly Arg Asp Glu Ala Ser Val Ala Ala Gln Ala Gly Arg Trp Ala Lys Trp Leu
Glu Glu His Gly Glu Val Gly Trp Ser Asp Val Val Arg Thr Ala Ala Leu His Arg Thr
His Phe Glu Ser Arg Ala Ser Met Leu Ala Ala Ser Val Ser Glu Val Val Glu Val Leu
Arg Ala Leu Ser Glu Gly Arg Gly His Arg Ala Val Ser Val Gly Thr Ala Arg Ala Arg
Gly Lys Val Val Phe Val Phe Pro Gly Gln Gly Ser Gln Trp Pro Gly Met Gly Arg Ala
Leu Leu Glu Gln Ser Ala Ala Phe Ala Glu Ala Val Gln Ala Cys Asp Glu Ala Leu Arg
Pro Trp Thr Gly Trp Ser Val Leu Ser Val Leu Arg Gly Asp Gly Gly Glu Glu Gln Pro
Ser Leu Glu Arg Val Asp Val Val Gln Pro Ala Leu Phe Ala Met Cys Val Gly Leu Ala
Ala Ala Trp Arg Ser Leu Gly Leu Glu Pro Ala Ala Val Val Gly His Ser Gln Gly Glu
Val Ser Ala Ala Val Val Cys Gly Ala Leu Ser Leu Ala Glu Gly Ala Arg Val Val Ala
Leu Arg Ser Gln Ala Val Arg Gln Gln Ser Gly Met Gly Ala Met Met Leu Val Glu Gln
Pro Val Ser Glu Val Gln Glu Arg Ile Ala Pro Tyr Gly Glu Ala Leu Ala Ile Ala Ala
Val Asn Thr Ser Asn Ser Thr Val Val Ser Gly Asp Val Glu Ala Val Asp Gly Leu Met
Val Glu Leu Thr Ala Glu Gly Val Phe Cys Arg Lys Val Asn Val Asp Tyr Ala Ser His
Ser Ala His Met Asp Ala Leu Leu Pro Glu Leu Gly Ala Lys Leu Ser Ser Leu Arg Pro
Lys Ala Thr Gln Leu Pro Phe Tyr Ser Thr Val Thr Gly Glu Val Ser Arg Gly Glu Ala
Leu Asp Gly Glu Tyr Trp Cys Arg Asn Leu Arg Gln Thr Val Arg Leu Asp Arg Ala Leu
Ser Lys Leu Leu Glu Asp Gly His Gly Val Phe Val Glu Val Ser Ala His Pro Val Leu
Ala Met Pro Leu Thr Thr Ala Cys Gly Glu Ala Gln Gly Val Val Val Gly Ser Leu Gln
Arg Asp Glu Gly Gly Leu Ser Gln Leu Tyr Arg Thr Leu Gly Gln Leu His Val Gln Gly
His Glu Val Asp Trp Ala Arg Val Leu Ser Gly His Gly Gly Arg Ala Val Glu Leu Pro
Thr Tyr Ala Phe Gln Arg Gln Arg Tyr Trp Leu Asp Ile Ser Lys Ala Arg Ser Asp Val
Ser Ser Ala Gly Leu Lys Ala Ala Ala His Pro Leu Leu Gly Ala Ala Thr Lys Leu Ala
Glu Gly Asp Gly His Leu Phe Thr Gly Arg Leu Ser Leu Gly Glu His Ala Trp Leu Arg
Asp His Glu Val Phe Gly Asn Leu Val Phe Pro Arg Ala Arg Gly Met Leu Glu Leu Ala
Leu Ala Ala Gly Pro His Gly Gly Gln Arg Gly Leu Phe Gly Lys >

FIG.4F pKOS035-453b2
Universal primer
GTGGGCGTTCGTTCCGCTGATCCCGAACGACGACACGCCCGCGCGCCGCGCCCGGCCGTTGCGCCGCCACGGACGCG
CCTCTTGCAGCAACGACAGCCCGCTCCCCTCCCACCCAATGTGCGGGCTCGGCTGCTCCGCGTGCAGCGTCCGCGGC
AGCACCTCGTGCTGCATCGACAGCACCATCTTGAGCACACCGGCGACGCCCGCCGCAGGCCCCGCCGTGTCCCAGGTT
CGACTTCGACGAGCCAAGGTACAGCGGCCGCTCGGCCTTGCGCCCAGGCCCGAACACCTCCACGAGCGCTC

FIG.5

PCR amplified KS fragment sequence pKOS035-454
Universal Primer
GACACGGCCTGTTCGTCGTCGCTGACCGCCCTGCACCTGGCGGTGCGGGCGCTGCGCAGCGGCGAGTGCACGATGGC
GCTCGCCGGTGGCGTGGCGATGATGGCGACCCCGCACATGTTCGTGGAGTTCAGCCGTCAGCGGGCGCTCGCCCCGG
ACGGCCGCAGCAAGGCCTTCTCGGCGGACGCCGACGGGTTCGGCGCCCGCGGAGGGCGTCGGCCTGCTGCTCGTGGAG
CGGCTCTCGGACGCGCGGCGCAACGGTCACCCGGTGCTCGCCGTGGTCCGCGGTACCGCCGTCAACCAGGACGGCGC
CAGCAACGGGCTGACCGCGCCCAACGGACCCTCGCAGCAGCGGGTGATCCGGCAGGCGCTCGCCGACGCCCGGCTGG
CACCCGGCGACATCGACGCCGTCGAGACGCACGGCACG

FIG.6

PCR amplified KS fragment sequence
pKOS035-4715
Reverse primer
ATGGGCGTTGGTGCCGCTGATCCCGAAGGAGGAGACGGCGGCCCCGGCGCAGCCCGCCGTCCTGCTTCTCCGGCCAGT
CGACGGCCTCGGTGAGGAGTTCCACGGCGCCAGCCGACCAGTCGATCTGGTCCGAGGGCTCGTCGACGTGCAGCGTC
TTCGGCAGCAGTCCGTGGCGCATCGCCTGGACCATCTTGATGACACCGGAGACGCCGGCCGCGGCCTGGGTGTGCCC
GATGTTGGACTTCAACGACCCGAGGCGCAGCGGCTGTTCGTCGTCACGGCCCTGGCCGTAGGTGGCGATCAGGGCCT
GCGCCTCGATCGGGTCGCCGAGTC

FIG.7

SORANGIUM POLYKETIDE SYNTHASES AND ENCODING DNA THEREFOR

The present application is a continuation-in-part of U.S. Ser. No. 09/010,809, filed Jan. 22, 1998, now U.S. Pat. No. 6,090,601, which is incorporated by reference herein, in its entirety, as if fully set forth.

REFERENCE TO GOVERNMENT FUNDING

This work herein described was supported at least in part by the U.S. government under SBIR grant 1R43 CA 79228-01. The U.S. government has certain rights in this invention.

FIELD OF THE INVENTION

The present invention relates to polyketides, and the polyketide synthase ("PKS") enzymes that are capable of producing such compounds. The invention also relates generally to genes encoding polyketide synthase enzymes, and to recombinant host cells in which expression of such genes leads to the production of polyketides.

Polyketides define a large and diverse group of biologically active molecules, many of which are antibiotic compounds. Tetracyclines, erythromycins, and epothilones are representative.

Given that it is difficult to produce polyketide compounds by traditional chemical approaches, and that expression from wild-type cells is generally at levels too low for practical commercial use, there has been considerable interest in finding alternate means to produce such compounds. Accordingly, the present invention is directed to the production of PKS enzymes in host cells in which they are advantageously expressed. Further enhancements in the biological activities of natural polyketides, through production of covalently modified forms thereof, is also made possible according to the practice of the invention.

A large variety of polyketides having a wide spectrum of useful biological activities are known, and further variations including those generated from combinatorial libraries are possible. As elaborated below, this nearly infinite design flexibility is made possible in part by the modular nature of polyketide synthases, which are actually highly ordered complexes of multiple catalytic domains organized into modules. Accordingly, further aspects of the present invention include, for example, (1) providing encoding DNA for a chimeric PKS that is substantially patterned on that which encodes a first PKS enzyme, but which incorporates one or more functional PKS domains, or fragments thereof, associated with production of a further PKS; and (2) the use of combinatorial or other technologies to further enhance the extent of PKS libraries and, therefore, polyketide libraries.

BACKGROUND OF THE INVENTION

Polyketides represent a large family of diverse compounds synthesized from 2-carbon units through a series of condensations and subsequent modifications. Polyketides occur in many types of organisms including fungi, and mycelial bacteria, in particular the actinomycetes. An appreciation for the wide variety of polyketide structures, and for their biological activities, may be gained upon review of the extensive art, for example, published International Patent Specifications WO 93/13663 and WO 95/08548; U.S. Pat. Nos. 5,098,837, 5,149,639, 4,874,748, 5,063,155; and the journal articles H. Fu et al., *Biochemistry*, 33, pp. 9321–9326, (1994); R. McDaniel et al., *Science*, 262, pp. 1546–1550, (1993); and J. Rohr, *Angew. Chem. Int. Ed. Engl.* 34(8), pp.881–888, (1995).

Polyketides are synthesized in nature on polyketide synthases ("PKS"). These enyzmes, which are actually complexes of multiple enzyme activities, are in some ways similar to, but in other ways different from, the synthases which catalyze condensation of 2-carbon units in the biosynthesis of fatty acids. Two major types of PKS are known which are very different in their construction and mode of synthesis. These are commonly referred to as Type I or "modular" and Type II "aromatic."

The PKS enzyme complexes that are the subject of the present invention are members of the group designated Type I or modular PKS. In this type of PKS, a set of separate catalytic active sites (each active site is termed a "domain", and a set thereof is termed a "module") exists for each cycle of carbon chain elongation and modification. Upon inspection of the structure of a polyketide it is generally possible to determine the number and nature of the PKS modules necessary to form the polyketide, although the number of polypeptides that provide the modules may remain unknown, as may the exact nature of the starter unit.

FIG. 9 of aforementioned WO95/08548 depicts a typical genetic model for a Type I PKS, in this case for 6-deoxyerythronolide B synthase ("DEBS") involved in the production of erythromycin. Six separate modules, each catalyzing a round of condensation and modification of a 2-carbon unit, are present. The number and type of catalytic domains that are present in each module varies (see the WO 95/08548 FIG. 9) based on the needed chemistry, and the total of 6 modules is provided on 3 separate polypeptides (designated DEBS-1, DEBS-2, and DEBS-3, with 2 modules per each). Each of the DEBS polypeptides is encoded from a separate open reading frame (gene), see Caffrey et al., *FEBS Letters*, 304, pp. 205, 1992.

The catalytic domains of the DEBS polypeptides provide a representative example of Type I PKS design. In this particular case, modules 1 and 2 reside on DEBS-1, modules 3 and 4 on DEBS-2, and modules 5 and 6 on DEBS-3, wherein module 1 is defined as the first module to act on the growing polyketide backbone, and module 6 the last.

A minimal PKS module may be typified by module 3 which contains a ketosynthase ("KS") domain, an acyltransferase ("AT") domain, and an acyl carrier protein ("ACP") domain. These three enzyme activities are sufficient to activate the 2-carbon extender unit and attach it to the growing polyketide molecule. Additional domains that may be included in a module relate to reactions other than the actual condensation, and include a ketoreductase activity ("KR") activity, a dehydratase activity ("DH"), and an enoylreductase activity ("ER"). With respect to DEBS-1, the first module thereof also contains repeats of the AT and ACP activities because it catalyzes initial condensation, i.e. it begins with a "loading domain" represented by AT and ACP, which determine the nature of the starter unit. The "finishing" of the 6-deoxyerythronolide molecule is regulated by a thioesterase activity ("TE") in module 6. This thioesterase appears to catalyze cyclization of the macrolide ring thereby increasing the yield of the particular polyketide product.

In PKS polypeptides, the regions that encode enzymatic activities (domains) are separated by linker or "scaffold"-encoding regions. These scaffold regions encode amino acid sequences that space the enzymatic activities (domains) at the appropriate distances and in the correct order. Thus, these linker regions collectively can be considered to encode a scaffold into which the various domains (and thus modules) are placed in a particular order and spatial arrangement. Generally, this organization permits PKS domains of different or identical substrate specificities to be substituted (usually at the level of encoding DNA) between PKS species by various available methodologies. Thus, there is considerable flexibility in the design of new PKS systems with the result that known polyketides can be produced more effectively, and novel polyketide pharmaceuticals can also be made.

As aforementioned, an additional level of structural complexity in the resultant polyketides may be introduced by subsequent glycosylation or other post-PKS chemical or enzymatic reactions.

DNA sequences that encode the novel PKS of the present invention may be included in a variety of host cells, there resulting novel recombinant host cells for the production of polyketides. Representative examples include those mentioned in U.S. patent application Ser. No. 09/114,083, filed Jul. 10, 1998, for example with reference to plant cells, and international patent publication WO 98/27203 where the examples of bacterial and yeast cells may be mentioned, the text of each application being incorporated by reference herein as if fully set forth. Additional suitable host cells include, for example, animal cells, and particular bacteria such as *E. coli*, Streptomyces, and Sorangium. According to the practice of the invention, particular host cells are selected on the basis of their capacity to facilitate expression of PKS enzymes, the capacity of such cells to produce (including secrete) polyketides, and the nature of the intracellular environment which may determine which substrates, including primers, are made available for reaction.

SUMMARY OF THE INVENTION

Sorangium bacteria are a valuable source of antibiotic compounds including antibacterial and antifungal compounds. In a first embodiment of the present invention, there are provided polynucleotides derived from *Sorangium cellulosum* that comprise encoding sequences for novel polyketide synthases, or domains or other fragments thereof. Representative examples include the PKS-encoding sequence found in cosmids pKOS28-26, pKOS034-43, pKOS034-46, pKOS034-53, and pKOS034-55.

In a further example, chimeric polynucleotides are provided that comprise PKS-encoding sequence corresponding to domains of more than one species of PKS, from one or more organisms. According to this example, at least one component of the chimera is PKS-encoding sequene from Sorangium, preferably corresponding to encoding sequence found on one of the above-identified cosmids. Expression of such encoding DNAs, typically in suitable host cells, leads to the production of useful quantities of polyketide synthases from which can be produced valuable polyketides. Also according to this aspect of the invention, individual domains in the resultant PKS may be encoded by nucleotide sequence from two or more different genes, or from different modules of a gene, and from PKS-encoding sequence dervied, for example, from two different organisms.

In such DNA molecules, the encoding sequences are operably linked to control sequences so that expression therefrom in host cells is effective. Modification of the structure of resultant polyketides, or of the amounts produced, may be controlled by selecting appropriate host cells. These and other aspects of the present invention, including use of combinatorial approaches, are described according to the Detailed Description of the Invention, which follows directly.

BRIEF DESCRIPTION OF THE DRAWINGS

FIG. 1 shows the DNA sequence in pKOS28-26 (SEQ ID NO:3), ATCC 209936.

FIG. 3 shows the amino acid sequence encoded by a first open reading frame (ORF 1, SEQ ID NO:1) in pKOS28-26.

FIG. 4 shows the amino acid sequence encoded by a second open reading frame (ORF2, SEQ ID NO:2) in pKOS28-26.

FIG. 5 shows a nucleotide sequence fragment of cosmid pKOS034-43 corresponding to a ketosynthase ("KS") domain of a *Sorangium cellulosum* SMP44 gene (SEQ ID NO:4).

FIG. 6 shows a nucleotide sequence fragment of cosmid pKOS034-46 corresponding to a ketosynthase ("KS") domain of a *Sorangium cellulosum* SMP44 gene (SEQ ID NO:5).

FIG. 7 shows a nucleotide sequence fragment of cosmid pKOS034-55 corresponding to a ketosynthase ("KS") domain of a *Sorangium cellulosum* SMP44 gene (SEQ ID NO:6).

DETAILED DESCRIPTION OF THE INVENTION

Figure 2:
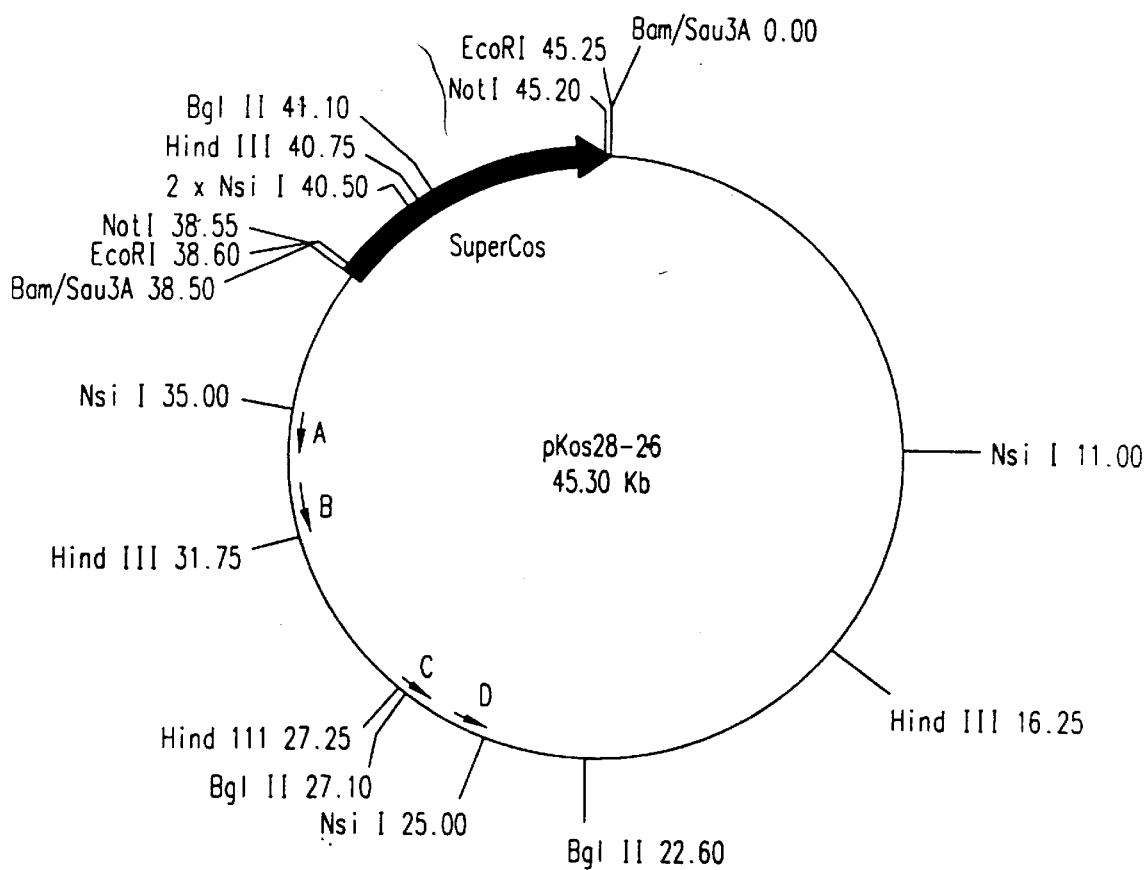
FIG. 2 shows a map the the 45.3 kb cosmid pKOS28-26.

Given the valuable pharmaceutical properties of polyketides, it is important to devise means by which pharmaceutically useful quantities thereof can be produced, and new and useful variants be discovered. As aforementioned, only limited quantities of polyketides are generally recovered from microbial cells that produce these substances, and resort to synthetic methods is impractical.

According to the practice of the invention, purified and isolated DNA molecules are provided that comprise one or more encoding sequences for one or more domains (or fragments of such domains) of Sorangium polyketide synthases. Examples of such encoded domains include KS, AT, DH, KR and ACP domains included with the amino acid sequences encoding by two open reading frames (OFR1, SEQ ID NO:1, and ORF2, SEQ ID NO:2) of the cosmid pKOS28-26, deposited with the American Type Culture Collection, Manassas, Va., USA as ATCC 209936. Nucleotide sequence from this cosmid is provided by SEQ ID NO:3.

Further aspects of the invention include:
(1) providing encoding DNA for a chimeric PKS that is substantially patterned on that of a non-Sorangium produced enzyme, but which incorporates one or more sequences corresponding to functional domains of Sorangium PKS, such domains being encoding regions of SEQ ID NO:3 and corresponding to domains or domain subsets of open reading frames 1 and 2 (SEQ ID NO:1, SEQ ID NO:2);
(2) providing encoding DNA for a chimeric PKS that is substantially patterned on a Sorangium produced enzyme, but which incorporates one or more sequences corresponding to functional domains of a PKS as defined by SEQ ID NO:3, and open reading frames 1 and 2 thereof;
(3) providing an encoding DNA for a chimeric PKS that is substantially patterned on a Sorangium enzyme as expressed, for example, from SEQ ID NO:3, but which includes one or more catalytic domains, or fragments thereof, associated with other PKS species, such as from Streptomyces;
(4) providing a complete expression plasmid/vector for a PKS system, such as based on SEQ ID NO:3, which is foreign to the host cell in which it is then placed, in order to use the properties of the new host cell to modify the polyketides that are produced, or the regulation of their production; and (5) the use of combinatorial or other technologies to further enhance the extent of PKS and polyketide libraries.

With respect to item (1) above, preferred examples include construction of chimeric PKS enzymes wherein the erythromycin PKS and rapamycin PKS function as accepting scaffolds or targets, and one or more of the above-identified Sorangium domains are inserted as replacements for domains of comparable function. Of course, construction of such enzymes is most effectively achieved by construction of appropriate encoding polynucleotides. In this regard, the examples of erythromycin PKS and rapamycin PKS are expected to be preferred given the low sequence homology between Sorangium and Streptomyces DNA, which is useful to avoid undesireable recombination events. In this example of the invention, it is not necessary to replace an entire domain of the target (scaffold) PKS with an entire domain of Sorangium PKS, rather peptide subsequences of a Sorangium PKS domain that correspond to a peptide subsequence in a target domain, or which otherwise provide useful function, may be used as replacements. Accordingly, appropriate encoding DNAs for construction of such chimeric PKS include those that encode at least 10, preferably 15, and most preferably 20 or more amino acids of a selected Sorangium domain. In an example thereof, the inserted amino acids comprise a domain active site (see Table 1).

In this example, use of the term "accepting scaffold" is intended to define the target PKS encoding DNA having one or more domains, or domain fragments, that are being replaced, for example by a corresponding Sorangium domain or domain fragment Such domains (and targets) have active catalytic roles. However, it is also within the practice of the present invention, in reference to strategies (1) to (5) above, to replace or exchange actual scaffold regions, that is, those regions of an open reading frame that provide proper spacing and orientation for catalytic domains.

Additional information concerning construction and expression of encoding DNAs for the novel PKS of the invention, and concerning combinatorial approaches, is as follows.

Broadly stated, the invention provides recombinant materials for the production of combinatorial libraries of polyketides wherein the polyketide members of the library are synthesized by PKS systems derived from naturally occurring PKS systems that are used as scaffolds. Generally, many members of these libraries may themselves be novel compounds, and the invention further includes novel polyketide members of these libraries. The invention methods may be directed to the preparation of an individual polyketide. The polyketide may or may not be novel, but the method of preparation permits a more convenient method of preparing it. The resulting polyketides may be further modified to convert them to antibiotics, typically, through glycosylation, or other covalent modifications.

In another aspect, the invention is directed to a multiplicity of cell colonies comprising a library of colonies wherein each colony of the library contains an expression vector for the production of a different modular PKS, but derived from a naturally occurring PKS. In a preferred embodiment, the different PKS are derived from the erythromycin PKS. In any case, the library of different modular PKS is obtained by modifying one or more of the regions of a naturally occurring gene or gene cluster encoding an enzymatic activity so as to alter that activity, leaving intact the scaffold portions of the naturally occurring gene. Preferably, the replacing activity is represented by a domain of Sorangium PKS or a subset thereof, as herein described. The invention is also directed to methods to produce libraries of PKS complexes and to produce libraries of polyketides by culturing these colonies, as well as to the libraries so produced. In addition, the invention is directed to methods to screen the resulting polyketide libraries and to novel polyketides contained therein.

Regardless of the naturally occurring PKS gene used as a scaffold, the invention provides libraries or individual modified forms, ultimately of polyketides, by generating modifications in the erythromycin PKS or other naturally occurring PKS gene cluster so that the protein complexes produced by the cluster have altered activities in one or more respects, and thus produce polyketides other than the natural product of the PKS. Novel polyketides may thus be prepared, or polyketides in general prepared more readily, using this method. By providing a large number of different genes or gene clusters derived from a naturally occurring PKS gene cluster, each of which has been modified in a different way from the native cluster, an effectively combinatorial library of polyketides can be produced as a result of the multiple variations in these activities. Again, use of Sorangium PKS domains is preferred.

In summary, a polyketide synthase "derived from" a naturally occurring PKS contains the scaffolding encoded by all the portion employed of the naturally occurring synthase gene, contains at least two modules that are finctional, and contains mutations, deletions, or replacements of one or more of the activities of these functional modules so that the nature of the resulting polyketide is altered. This definition applies both at the protein and genetic levels. Particular preferred embodiments include those wherein a KS, AT, KR, DH or ER has been deleted or replaced by a version of the activity from a different PKS or from another location within the same PKS. Also preferred are derivatives where at least one noncondensation cycle enzymatic activity (KR, DH or ER) has been deleted or wherein any of these activities has been mutated so as to change the ultimate polyketide synthesized. In the typical practice of the invention, when a domain or version of activity is replaced with that of a different PKS, a Sorangium PKS domain is replaced with that of a different PKS, such as from Streptomyces, or is inserted inot the PKS from such organism. Such methods are applicable also to fragments of domains, such as those representing the enzyme (domain) active site, see Table I.

Thus, there are five degrees of freedom for constructing a polyketide synthase in terms of the polyketide that will be produced. First, the polyketide chain length will be determined by the number of modules in the PKS. Second, the nature of the carbon skeleton of the PKS will be determined by the specificities of the acyl transferases which determine the nature of the extender units at each position—e.g., malonyl, methyl malonyl, or ethyl malonyl, etc. Third, the loading domain specificity will also have an effect on the resulting carbon skeleton of the polyketide. Thus, the loading domain may use a different starter unit, such as acetyl, propionyl, and the like. Fourth, the oxidation state at various positions of the polyketide will be determined by the dehydratase and reductase portions of the modules. This will determine the presence and location of ketone, alcohol, alkene or alkane substituents at particular locations in the polyketide. Finally, the stereochemistry of the resulting polyketide is a function of three aspects of the synthase. The first aspect is related to the AT/KS specificity associated with substituted malonyls as extender units, which affects stereochemistry only when the reductive cycle is missing or when it contains only a ketoreductase since the dehydratase would abolish chirality. Second, the specificity of the ketoreductase will determine the chirality of any β-OH. Finally, the enoyl reductase specificity for substituted malonyls as extender units will influence the result when there is a complete KR/DH/ER available.

Methods useful in support of construction of novel modular PKS are as follows.

A large number of modular PKS gene clusters have been mapped and/or sequenced, including for erythromycin and rapamycin, which have been completely mapped and sequenced, and for soraphen A, FK506 and oleandomycin which have been partially sequenced, and for candicidin, avermectin, and nemadectin which have been mapped and partially sequenced. Additional modular PKS gene clusters are expected to be available as time progresses. These genes can be manipulated using standard techniques to delete or inactivate activity encoding regions, insert regions of genes encoding corresponding activities from the same or different PKS systems, or be otherwise mutated using standard procedures for obtaining genetic alterations. Of course, portions of, or all of, the desired derivative coding sequences can be synthesized using standard solid phase synthesis methods such as those described by Jaye et al., *J Biol Chem* (1984) 259:6331 and which are available commercially from, for example, Applied Biosystems, Inc. Again, use of, or replacement of, Sorangium sequences is preferred.

In order to obtain nucleotide sequences encoding a variety of derivatives of the naturally occurring PKS, and thus a variety of polyketides for construction of a library, a desired number of constructs can be obtained by "mixing and matching" enzymatic activity-encoding portions, and mutations can be introduced into the native host PKS gene cluster or portions thereof. Use of encoding sequence for Sorangium domains is preferred.

Mutations can be made to the native sequences using conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene encoding a PKS subunit using restriction endonuclease digestion. (See, e.g., Kunkel, T. A. *Proc Natl Acad Sci USA* (1985) 82:448; Geisselsoder et al. *Bio Techniques* (1987) 5:786.) Alternatively, the mutations can be effected using a mismatched primer (generally 10–20 nucleotides in length) which hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. Zoller and Smith, *Methods in Enzymology* (1983) 100:468. Primer extension is effected using DNA polymerase. The product of the extension reaction is cloned, and those clones containing the mutated DNA are selected. Selection can be accomplished using the mutant primer as a hybridization probe. The technique is also applicable for generating multiple point mutations. See, e.g., Dalbie-McFarland et al. *Proc Natl Acad Sci USA* (1982) 79:6409. PCR mutagenesis will also find use for effecting the desired mutations.

Random mutagenesis of selected portions of the nucleotide sequences encoding enzymatic activities can be accomplished by several different techniques known in the art, e.g., by inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants or by damaging plasmid DNA in vitro with chemicals. Chemical mutagens include, for example, sodium bisulfite, nitrous acid, hydroxylamine, agents which damage or remove bases thereby preventing normal base-pairing such as hydrazine or formic acid, analogues of nucleotide precursors such as nitrosoguanidine, 5-bromouracil, 2-aminopurine, or acridine intercalating agents such as proflavine, acriflavine, quinacrine, and the like. Generally, plasmid DNA or DNA fragments are treated with chemicals, transformed into *E. coli* and propagated as a pool or library of mutant plasmids.

In addition to providing mutated forms of regions encoding enzymatic activity, regions encoding corresponding activities from different PKS synthases or from different locations in the same PKS synthase can be recovered, for example, using PCR techniques with appropriate primers. By "corresponding" activity encoding regions is meant those regions encoding the same general type of activity—e.g., a ketoreductase activity in one location of a gene cluster would "correspond" to a ketoreductase-encoding activity in another location in the gene cluster or in a different gene cluster; similarly, a complete reductase cycle could be considered corresponding—e.g., KR/DH/ER would correspond to KR alone.

If replacement of a particular target region in a host polyketide synthase is to be made, this replacement can be conducted in vitro using suitable restriction enzymes or can be effected in vivo using recombinant techniques involving homologous sequences framing the replacement gene in a donor plasmid and a receptor region in a recipient plasmid. Such systems, advantageously involving plasmids of differing temperature sensitivities are described, for example, in PCT Publication WO 96/40968.

The vectors used to perform the various operations to replace the enzymatic activity in the host PKS genes or to support mutations in these regions of the host PKS genes may be chosen to contain control sequences operably linked to the resulting coding sequences in a manner that expression of the coding sequences may be effected in a appropriate host. However, simple cloning vectors may be used as well.

If the cloning vectors employed to obtain PKS genes encoding derived PKS lack control sequences for expression operably linked to the encoding nucleotide sequences, the nucleotide sequences are inserted into appropriate expression vectors. This need not be done individually, but a pool of isolated encoding nucleotide sequences can be inserted into host vectors, the resulting vectors transformed or transfected into host cells and the resulting cells plated out into individual colonies.

Suitable control sequences include those which function in eucaryotic and procaryotic host cells. Preferred hosts include fungal systems such as yeast and procaryotic hosts, but single cell cultures of, for example, mammalian cells could also be used. There is no particular advantage, however, in using such systems. Particularly preferred are yeast and procaryotic hosts which use control sequences compatible with Streptomyces spp. and Sorangium spp. Suitable control sequences for single cell cultures of various types of organisms are well known in the art. Control systems for expression in yeast, including controls which effect secretion are widely available and are routinely used. Control elements include promoters, optionally containing operator sequences, and other elements depending on the nature of the host, such as ribosome binding sites. Particularly useful promoters for procaryotic hosts include those from PKS gene clusters which result in the production of polyketides as secondary metabolites, including those from aromatic (Type II) PKS gene clusters. Examples are act promoters, tcm promoters, spiramycin promoters, and the like. However, other bacterial promoters, such as those derived from sugar metabolizing enzymes, such as galactose, lactose (lac) and maltose, are also useful. Additional examples include promoters derived from genes for biosynthetic enzymes such as those for the biosynthesis of tryptophan (trp), the β-lactamase (bla) gene, and bacteriophage lambda PL, and T5. In addition, synthetic promoters, such as the tac promoter (U.S. Pat. No. 4,551,433), can be used.

Other regulatory sequences may also be desirable which allow for regulation of expression of the PKS replacement sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes which confer antibiotic resistance or sensitivity to the plasmid. Alternatively, several polyketides are naturally colored and this characteristic provides a built-in marker for screening cells successfully transformed by the present constructs.

The various PKS nucleotide sequences, or a cocktail of such sequences, can be cloned into one or more recombinant vectors as individual cassettes, with separate control elements, or under the control of, e.g., a single promoter. The PKS subunits or cocktail components can include flanking restriction sites to allow for the easy deletion and insertion of other PKS subunits or cocktail components so that hybrid PKSs can be generated. The design of such unique restriction sites is known to those of skill in the art and can be accomplished using the techniques described above, such as site-directed mutagenesis and PCR.

As described above, particularly useful control sequences are those which themselves, or using suitable regulatory systems, activate expression during transition from growth to stationary phase in the vegetative mycelium. The system contained in the plasmid identified as pCK7, i.e., the actI/actIII promoter pair and the actII-ORF4 (an activator gene), is particularly preferred. Particularly preferred hosts are those which lack their own means for producing polyketides so that a cleaner result is obtained. Illustrative host cells of this type include the modified *S. coelicolor* CH999 culture described in PCT Publication WO 96/40968 and similar strains of *S. lividans*.

The expression vectors containing nucleotide sequences encoding a variety of PKS systems for the production of different polyketides are then transformed into the appropriate host cells to construct the library. In one straightforward approach, a mixture of such vectors is transformed into the selected host cells and the resulting cells plated into individual colonies and selected for successful transformants. Each individual colony will then represent a colony with the ability to produce a particular PKS synthase and ultimately a particular polyketide. Typically, there will be duplications in some of the colonies; the subset of the transformed colonies that contains a different PKS in each member colony can be considered the library. Alternatively, the expression vectors can be used individually to transform hosts, which transformed hosts are then assembled into a library. A variety of strategies might be devised to obtain a multiplicity of colonies each containing a PKS gene cluster derived from the naturally occurring host gene cluster so that each colony in the library produces a different PKS and ultimately a different polyketide. The number of different polyketides that are produced by the library is typically at least four, more typically at least ten, and preferably at least 20, more preferably at least 50, reflecting similar numbers of different altered PKS gene clusters and PKS gene products. The number of members in the library is arbitrarily chosen; however, the degrees of freedom outlined above with respect to the variation of starter, extender units, stereochemistry, oxidation state, and chain length is quite large.

Methods for introducing the recombinant vectors of the present invention into suitable hosts are known to those of skill in the art and typically include the use of $CaCl_2$ or other agents, such as divalent cations, lipofection, DMSO, protoplast transformation and electroporation.

As disclosed in the co-pending application entitled "Production of Polyketides in Bacteria and Yeasts" U.S. Pat. No. 6,033,833, as filed on Dec. 11, 1997) incorporated herein by reference, a wide variety of hosts can be used, even though some hosts natively do not contain the appropriate post-translational mechanisms to activate the acyl carrier proteins of the synthases. These hosts can be modified with the appropriate recombinant enzymes to effect these modifications.

The polyketide producing colonies can be identified and isolated using known techniques and the produced polyketides further characterized. The polyketides produced by these colonies can be used collectively in a panel to represent a library or may be assessed individually for activity.

The libraries can thus be considered at four levels: (1) a multiplicity of colonies each with a different PKS encoding sequence encoding a different PKS cluster but all derived from a naturally occurring PKS cluster; (2) colonies which contain the proteins that are members of the PKS produced by the coding sequences; (3) the polyketides produced; and (4) antibiotics derived from the polyketides. Of course, combination libraries can also be constructed wherein members of a library derived, for example, from the erythromycin PKS can be considered as a part of the same library as those derived from, for example, the rapamycin PKS cluster. Construction strategies that insert Sorangium PKS components into other PKS, or vice versa, are preferred.

Colonies in the library are induced to produce the relevant synthases and thus to produce the relevant polyketides to obtain a library of candidate polyketides. The polyketides secreted into the media can be screened for binding to desired targets, such as receptors, signaling proteins, and the like. The supernatants per se can be used for screening, or partial or complete purification of the polyketides can first be effected. Typically, such screening methods involve detecting the binding of each member of the library to receptor or other target ligand. Binding can be detected either directly or through a competition assay. Means to screen such libraries for binding are well known in the art. Alternatively, individual polyketide members of the library can be tested against a desired target. In this event, screens wherein the biological response of the target is measured can more readily be included.

EXAMPLES

Example 1

Isolation and Structure of Cosmid pKOS28-26

A general ketosynthase domain probe was generated from *Sorangium cellulosum* SMP44 chromosomal DNA using degenerate primers designed by alignment of ketosynthase (KS) domains from a number of polyketide synthases. The degenerate primers used were as follows, wherein bases are designated using art-recognized single letter designations as also provided for in 37 CFR 1.822(b)(1):

primer 1: 5'-RTG SGC RTT VGT NCC RCT-3' (SEQ ID NO:7)

primer 2; 5'-GAC ACV GCN TGY TCB TCV-3' (SEQ ID NO:8)

wherein R=A and G; Y=C and T; S=G and C; B=G and T and C; N=A and G and C and T; and V=G and A and C.

The resultant PCR product was approximately 800 bp long, and was then non-radioactively labelled with DIG nucleotides (Boehringer Mannheim) for detection. A cosmid library of partial Sau3A digested chromosomal DNA fragments from *Sorangium cellulosum* SMP44 was generated in the Supercos system (Stratagene). The library was then screened by colony hybridization using the general KS domain probe. Cosmid pKOS28-26 was identified as a cosmid that hybridized with the KS domain probe. In general, encoding DNA for polyketide synthase modules ranges from about 3 to 5 kb (depending on the reductive cycle activities that are present).

The DNA sequence of pKOS28-26 is provided in SEQ ID NO:3 and the amino acid sequences corresponding to two open reading frames (SEQ ID NO:1, FIG. 3, and SEQ ID NO:2, FIG. 4) identified therein are also provided. Table 1 provides the domain types identified in the modules of the open reading frames (i.e. KS, AT, DH, KR, ACP). The amino acid positions that identify the domain boundaries are also identified. In numerous cases, the enzyme(domain) active sites are also indicated. The two identified orders for domain elements within the determined modules are:

KS-AT-DH-KR-ACP and
KS-AT-KR-ACP.

Example 2

Additional Sorangium Ketosynthase Domains

Four additional cosmids (pKOS034-43, pKOS034-46, pKOS034-53, and pKOS034-55) have been identified based on the identification of KS domains corresponding to Sorangium polyketide synthases.

Chromosomal DNA was prepared of *Sorangium cellulosum* SMP44, a strain known to produce PKS for epothilone. The DNA was cleaved partially with Sau3AI and ligated into the cosmid vector Supercos-1 (Stratagene) to construct a library. The above-identified cosmids were identified by screening with KS probes that had been PCR amplified from the erythromycin and rapamycin gene clusters.

The cosmids were then used as DNA templates for PCR reactions using degenerate KS oligos identified as YXS-1 and YXS-2 (compare underlining in FIGS. 5–7, SEQ ID NOS 4–6). Using the coding system recognized in 37 CFR 1.822, the oligos were as follows:

YXS-1 RTGSGCRTTVGTNCCRCT (SEQ ID NO:7)
YXS-2 GACACVGCNTGYTCBTCV (SEQ ID NO:8).

At least one sequence having KS domain homology was identified in each cosmid. Representative nucleotide sequences having homology to KS encoding sequence were placed in pZeo 2.1 plasmids (Invitrogen) and are identified as pKOS035-453b2 (FIG. 5), pKOS035-454 (FIG. 6), and pKOS035-4715 (FIG. 7), all of which are depicted 5' to 3'. In the Figures, the depicted nucleotide sequences are non-coding (FIGS. 5 and 7) and coding (FIG. 6).

In further support of the present disclosure, on Jun. 2, 1998, a deposit of biological material of confirmed viability was made with the American Type Culture Collection, Manassas, Va., USA under the Budapest Treaty. The material is identified as cosmid DNA pKOS28-26, and has been assigned ATCC number 209936. Upon the granting of a patent herein, all restrictions on the availability of this material to the public will be irrevocably removed.

TABLE 1

Sorangium 33.5 kbp Contig I Domains

| AA start | start seq | AA end | end seq | domain type | comments |
|---|---|---|---|---|---|
| | | | | orf1 | |
| <1 | | 339 | GTNAHVILEE | KS | active site = TACSSSL |
| 450 | VFVFPGQG | 780 | VDWARVLPG | AT | sequence → methylmalonyl specific RVDVVQPALFAMCVGLAAAW ... 11 ... GHSQG |
| 807 | GDVSSAGL | 985 | YGPTQGL | DH | consensus HGVFGQVVFP @ 851 consensus GLHYGPTFQ @ 975 |
| 1315 | PAGTVLVT | 1500 | WGVWTPAGG | KR | |
| 1592 | LSALPEAER | 1675 | PRAIAELLLK | ACP | active Site = LGLDSL |
| 1698 | EAVAIVSM | 2121 | GTNAHVILEE | KS | active site = TACSSSL |
| 2232 | AVLFTGQG | 2564 | VDWAQVLSG | AT | sequence → malonyl-specific RTEYTQPGLFALEVALYRQW ... 11 ... GHSIG |
| 2861 | PRGTVLIT | 3045 | WGPWSGGGM | KR | |
| 3134 | LLGLPAVER | 3218 | VTRWLLEQ | ACP | active site = LGLDSL |
| 3240 | APIAIVGV | 3665 | GTNAHVILEE | KS | active site = TACSSSL |
| 3775 | AVLFTGQG | 4107 | VDWAQVLSG | AT | sequence → malonyl-specific RTEYTQPGLFALEVALYRQW ... 11 ... GHSIG |
| 4134 | GDVGSAGL | 4312 | YGPVFQGL | DH | consensus HQVFGKVVFP @ 4178 consensus GLDYGPVFQ @ 4302 |
| 4641 | PAGTVLVT | 4825 | WGLWAQAGV | KR | |
| 4918 | LSALPEAER | 5001 | THIAKFLLS | ACP | active site = LGMDSL |
| | | | | orf2 | |
| 34 | GPIAIVSM | 457 | GTNAHVILEE | KS | active site = TACSSSL |
| 568 | VFVFPGQG | 895 | VDWTRVLSG | AT | sequence → methylmalonyl-specific RVDVVQPALFAMCVGLAAAW ... 11 ... GHSQG |

TABLE 1-continued

Sorangium 33.5 kbp Contig I Domains

| AA start | start seq | AA end | end seq | domain type | comments |
|---|---|---|---|---|---|
| 922 | SDVDSAGL | 1100 | YGPAFQGL | DH | consensus HEVFGQVVLP @ 966<br>consensus GLHYGPAFQ @ 1089 |
| 1429 | PAGTVLVT | 1614 | WGFWTQAGV | KR | |
| 1706 | LSALPEAER | 1789 | PRAIAELLLK | ACP | active site = LGLDSL |
| 1812 | EPIAIVSM | 2235 | GTNAHVILEE | KS | active site = TACSSSL |
| 2341 | AVLFTGQG | 2673 | VDWARVLSG | AT | sequence → malonyl-specific<br>RTEYTQPGLFALEVALYRQW . . . 11 . . . GHSIG |
| 2978 | PRGTVLIT | 3162 | WGPWAGEGM | KR | |
| 3250 | LLGLSEAER | 3333 | DVARWLLE | ACP | active site = LGLDSL |
| 3356 | TPIAIVGV | 3781 | GTNAHVILEE | KS | active site = TACSSSL |
| 3887 | AVLFTGQG | 4219 | VDWAQVLSG | AT | sequence → malonyl-specific<br>RTEYTQPGLFALEVALYRQW . . . 11 . . . GHSIG |
| 4246 | TDVGSAGL | 4424 | YGPAFQGL | DH | consensus HAVFGEVVFP @ 4290<br>consensus GLRYGPAFQ @ 4413 |
| 4754 | PTGTVLV | 4939 | WGFWAQTGV | KR | |
| 5031 | LSELPEAER | 5114 | PRAVAELLLR | ACP | active site = LGLDSL |
| 5134 | DEAIAIVSM | 5558 | GTNAHVILEE | KS | active site = TACSSSL |
| 5664 | VFVFPGQG | 5991 | VDWARVLSG | AT | sequence → methylmalonyl-specific<br>RVDVVQPALFAMCVGLAAAW . . . 11 . . . GHSQG |
| 6018 | SDVSSAG | >6095 | ? | DH | consensus HEVFGNLVFP @ 6062 |

What is claimed is:

1. A purified and isolated DNA molecule that comprises a polyketide synthase open reading frame, wherein said open reading frame encodes one or more modules, and wherein one or more domains thereof are selected from the groups consisting of
   (a) a ketosynthase domain of SEQ ID NO:1 (FIG. 3) identified, as amino acid positions, 1 to 339, 1698 to 2121, and 3240–3665 thereof;
   (b) a ketosynthase domain of SEQ ID NO:2 (FIG. 4) identified, as amino acid positions, 34 to 457, 1812 to 2235, 3356–3781, and 5134–5558 thereof;
   (c) an acyltransferase domain of SEQ ID NO:1 (FIG. 3) identified, as amino acid positions, 450 to 780, 2232–2564, and 3775–4107 thereof;
   (d) an acyltransferase domain of SEQ ID NO:2 (FIG. 4) identified, as amino acid positions, 568 to 895, 2341 to 2673, 3887–4219, and 5664–5991 thereof;
   (e) a dehydratase domain of SEQ ID NO:1 (FIG. 3) identified, as amino acid positions, 807 to 985, and 4134 to 4312 thereof;
   (f) a dehydratase domain of SEQ ID NO:2 (FIG. 4) identified, as amino acid positions, 922 to 1100, 4246 to 4424, and 6018 to 6095 thereof;
   (g) a ketoreductase domain of SEQ ID NO:1 (FIG. 3) identified, as amino acid positions, 1315 to 1500, 2861 to 3045, and 4641 to 4825 thereof;
   (h) a ketoreductase domain of SEQ ID NO:2 (FIG. 4) identified, as amino acid positions, 1429 it 1614, 2978 to 3162, and 4754 to 4939 thereof;
   (i) an acyl carrier protein domain of SEQ ID NO:1 (FIG. 3 ) identified, as amino acid positions, 1592 to 1675, 3134 to 3218, and 4918 to 5001 thereof; and
   (j) an acyl carrier protein domain of SEQ ID NO:2 (FIG. 4) identified, as amino acid positions, 1706 to 1789, 3250 to 3333, and 5031 to 5114 thereof.

2. A purified and isolated DNA molecule according to claim 1 wherein said open reading frame includes one of the domains that comprises at least about 15 consecutive amino acids selected from a domain (a) through (j).

3. A purified and isolated DNA molecule according to claim 2 wherein said open reading frame includes a domain that comprises at least about 20 consecutive amino acids selected from one of the domains (a) through (j).

4. A purified and isolated DNA molecule comprising a *Sorangium cellulosum* DNA sequence that consists of SEQ ID NO:3.

5. A purified and isolated DNA molecule that encodes at least one domain of a *Sorangium cellulosum* polyketide synthase selected from those polyketide synthase domains found on cosmid pKOS28-26.

6. A recombinant host cell that comprises a DNA molecule according to claim 1, in which a polyketide synthase is expressed and a polyketide produced.

7. A recombinant host cell that comprises a DNA molecule according to claim 5, in which a polyketide synthase is expressed and a polyketide produced.

8. A purified and isolated DNA molecule that comprises a polyketide synthase open reading frame, wherein said open reading frame encodes one or more modules, and wherein one or more domains of said one or more modules comprise ketosynthase ("KS") domains that are encoded by a nucleotide sequence selected from the group consisting of SEQ ID NO:4, SEQ ID NO:5, and SEQ ID NO:6.

* * * * *

SEQUENCE LISTING

<160> NUMBER OF SEQ ID NOS: 8

<210> SEQ ID NO 1
<211> LENGTH: 5087
<212> TYPE: PRT
<213> ORGANISM: Sorangium cellulosum

<400> SEQUENCE: 1

Asp Pro Gln Gln Arg Leu Val Leu Glu Thr Ala Trp Glu Ala Leu Glu
 1               5                  10                  15

Arg Ala Gly Val Arg Pro Ser Ala Leu Ser Gly Ser Ala Thr Gly Val
            20                  25                  30

Tyr Leu Gly Ser Met Gly Ser Asp Tyr Gly Ala Leu His Thr Gly Gly
        35                  40                  45

Leu Glu Ala Leu Asp Gly Tyr Arg Gly Thr Gly Ser Ala Ala Ser Val
    50                  55                  60

Leu Ser Gly Arg Val Ala Tyr Val Leu Gly Leu Gln Gly Pro Ala Ile
65                  70                  75                  80

Thr Val Asp Thr Ala Cys Ser Ser Leu Val Ser Leu His Leu Ala
                85                  90                  95

Cys Thr Ala Leu Arg Gln Gly Glu Cys Asp Leu Ala Leu Ala Gly Gly
                100                 105                 110

Val Thr Val Met Ser Thr Pro Ala Leu Phe Val Glu Phe Ser Arg Leu
            115                 120                 125

Lys Gly Met Ala Arg Asp Gly Arg Cys Lys Ser Phe Ser Ala Arg Ala
        130                 135                 140

Asp Gly Val Thr Trp Ser Glu Gly Cys Gly Met Leu Val Leu Lys Arg
145                 150                 155                 160

Leu Ser Asp Ala Arg Arg Asp Gly Asp Arg Val Leu Ala Val Val Arg
                165                 170                 175

Gly Ser Ala Val Asn Gln Asp Gly Arg Ser Gln Gly Leu Thr Ala Pro
            180                 185                 190

Asn Gly Pro Ala Gln Gln Arg Val Val Gln Arg Ala Leu Ser Ser Cys
        195                 200                 205

Gly Leu Ser Pro Glu Asp Ile Asp Ala Val Glu Ala His Gly Thr Gly
    210                 215                 220

Thr Ser Leu Gly Asp Pro Ile Glu Ala Gly Ala Leu Ala Glu Val Phe
225                 230                 235                 240

Gly Pro Gly Arg Lys Ala Glu Arg Pro Leu Tyr Leu Gly Ser Ser Lys
                245                 250                 255

Ser Asn Leu Gly His Thr Gly Pro Ala Ala Gly Val Val Gly Val Leu
            260                 265                 270

Lys Met Val Leu Ser Met Gln His Glu Val Leu Pro Arg Thr Leu His
        275                 280                 285

Ala Glu Gln Pro Ser Pro His Ile Gly Trp Glu Gly Ser Gly Leu Ser
    290                 295                 300

Leu Leu Gln Glu Ala Arg Pro Trp Arg Arg Asn Gly Arg Ala Arg Arg
305                 310                 315                 320

Ala Gly Val Ser Ser Phe Gly Ile Ser Gly Thr Asn Ala His Val Ile
                325                 330                 335

Leu Glu Glu Ala Pro Val Glu Ala Arg Glu Pro Val Glu Ala Val
            340                 345                 350

Arg Glu Pro Leu Ala Thr Glu Gly Val Ala Met Pro Leu Leu Leu Ser

-continued

```
             355                 360                 365
Gly Arg Asp Glu Ala Ser Val Ala Gln Ala Glu Arg Trp Ala Lys
    370                 375                 380
Trp Leu Glu Glu His Ala Glu Val Gly Trp Ser Asp Val Val Arg Thr
385                 390                 395                 400
Ala Ala Leu His Arg Thr His Phe Ala Ser Arg Ala Ser Val Leu Ala
                405                 410                 415
Ala Ser Val Ser Glu Ala Glu Ala Leu Arg Ala Leu Ser Gln Gly
            420                 425                 430
Arg Gly His Arg Ala Val Ser Ala Gly Thr Ala Arg Ala Arg Gly Lys
                435                 440                 445
Val Val Phe Val Phe Pro Gly Gln Gly Ser Gln Trp Pro Gly Met Gly
    450                 455                 460
Arg Ala Leu Leu Glu Gln Ser Ala Ala Phe Ala Glu Ala Val Gln Ala
465                 470                 475                 480
Cys Asp Glu Ala Leu Arg Pro Trp Thr Gly Trp Ser Val Leu Ser Val
                485                 490                 495
Leu Arg Gly Glu Ala Gly Glu Ala Gly Glu Glu Gln Pro Ser Leu Glu
            500                 505                 510
Arg Val Asp Val Val Gln Pro Ala Leu Phe Ala Met Cys Val Gly Leu
            515                 520                 525
Ala Ala Ala Trp Arg Ser Leu Gly Leu Glu Pro Ala Ala Val Val Gly
            530                 535                 540
His Ser Gln Gly Glu Val Ser Ala Ala Val Val Cys Gly Ala Leu Ser
545                 550                 555                 560
Leu Ala Glu Gly Ala Arg Val Val Ala Leu Arg Ser Gln Ala Val Arg
                565                 570                 575
Gln Arg Ser Gly Met Gly Ala Met Met Leu Val Glu Arg Pro Val Ser
            580                 585                 590
Glu Val Gln Glu Arg Ile Ala Pro Tyr Gly Glu Ala Leu Ala Ile Ala
            595                 600                 605
Ala Val Asn Thr Ser Ser Thr Val Val Ser Gly Asp Val Glu Ala
    610                 615                 620
Val Asp Gly Leu Met Gly Glu Leu Thr Ala Glu Gly Val Phe Cys Arg
625                 630                 635                 640
Lys Val Asn Val Asp Tyr Ala Ser His Ser Ala His Met Asp Ala Leu
                645                 650                 655
Leu Pro Glu Leu Gly Ala Lys Leu Ser Ser Leu Arg Pro Lys Ala Thr
            660                 665                 670
Gln Leu Pro Phe Tyr Ser Thr Val Ala Gly Glu Val Ser Arg Gly Glu
            675                 680                 685
Ala Leu Asp Gly Glu Tyr Trp Cys Arg Asn Leu Arg Gln Thr Val Arg
    690                 695                 700
Leu Asp Arg Ala Leu Ser Lys Leu Leu Glu Asp Gly His Gly Val Phe
705                 710                 715                 720
Val Glu Val Ser Ala His Pro Val Leu Ala Met Pro Leu Thr Thr Ala
                725                 730                 735
Cys Gly Glu Ala Gln Gly Val Val Gly Ser Leu Gln Arg Asp Glu
            740                 745                 750
Gly Gly Leu Ser Gln Leu Tyr Arg Thr Leu Gly Gln Leu His Val Gln
            755                 760                 765
Gly His Glu Val Asp Trp Ala Arg Val Leu Pro His Gly Gly Arg
    770                 775                 780
```

-continued

Ala Val Glu Leu Pro Thr Tyr Ala Phe Gln Arg Gln Arg Tyr Trp Leu
785                 790                 795                 800

Glu Ala Pro Arg Ala Arg Gly Asp Val Ser Ser Ala Gly Leu Lys Ala
            805                 810                 815

Ala Ala His Pro Leu Leu Gly Ala Ala Thr Lys Leu Ala Asp Gly Glu
            820                 825                 830

Gly His Leu Phe Thr Gly Arg Leu Ser Leu Ala Glu His Ala Trp Leu
            835                 840                 845

Arg Asp His Gly Val Phe Gly Gln Val Val Phe Pro Gly Thr Gly Met
850                 855                 860

Leu Glu Val Ala Leu Ala Ala Gly Arg Ala Val Gly Ser Arg Ser Leu
865                 870                 875                 880

Ser Glu Leu Thr Leu Ala Glu Pro Leu Val Leu Ala Glu Asp Gly Ala
            885                 890                 895

Ala Arg Leu Gln Val Met Ile Gly Ala Pro Asp Ala Ala Gly Arg Arg
            900                 905                 910

Glu Val Gly Leu Tyr Ser Gln Pro Glu His Ala Pro Glu Asp Ala Pro
            915                 920                 925

Trp Val Gln His Ala Thr Gly Val Leu Thr Asp Glu Leu Pro Gly Ile
930                 935                 940

Pro Asp Glu Leu Asp Glu Leu Ser Met Trp Pro Val Pro Gly Ala Glu
945                 950                 955                 960

Glu Val Asp Leu Ser Gly Phe Tyr Glu Arg Leu Arg Glu Arg Gly Leu
            965                 970                 975

His Tyr Gly Pro Thr Phe Gln Gly Leu Val Glu Leu Ser Arg Gln Gly
            980                 985                 990

Thr Arg Leu Tyr Gly Arg Val Val Leu Pro Gly Thr Glu Lys Asp Arg
            995                 1000                1005

Ala Glu Ala Tyr Gly Leu His Pro Val Leu Met Asp Ala Ala Leu Gln
    1010                1015                1020

Val Leu Gly Ala Ala Gly Glu Gly His Trp Glu Ala Asp Ala Leu Phe
1025                1030                1035                1040

Met Pro Phe Ser Trp Ala Asp Ala Ala Thr His Ala Thr Gly Pro Ser
                1045                1050                1055

Glu Leu Arg Val Arg Val Glu Leu Glu Glu Thr Asp Gly Ser Thr Gln
                1060                1065                1070

Ala Thr Ala Ser Leu Cys Ala Ala Asp Ala Ala Gly Gln Pro Val Ala
            1075                1080                1085

Ser Val Gly Ala Leu Arg Leu Arg Arg Val Thr Ala Glu Gln Leu Arg
    1090                1095                1100

Ala Val Thr Arg Thr Asp Glu Gln His Leu Tyr Arg Val Ser Phe Gln
1105                1110                1115                1120

Pro Val Ser Leu Ala Gln Ala Pro Leu Glu Ala Gly Ser Leu Val Val
                1125                1130                1135

Leu Gly Ala Ala Glu Gly Arg Gly Gln Leu Ala Asp Thr Leu Gly Ala
            1140                1145                1150

Glu Ala Ile Ala Asp Leu Asp Ala Leu Arg Ala Trp Ile Glu Arg Gly
            1155                1160                1165

Ala Pro Thr Pro Val Arg Val Val Ile Asp Thr Asn Ala Ala Ser Ser
    1170                1175                1180

Pro Arg Ser Asp Val Ala Gly Ser Ser His Glu Ala Thr Arg Gln Ala
1185                1190                1195                1200

-continued

```
Leu Ser Leu Leu Gln Ala Trp Leu Ser Glu Pro Arg Leu Asp Ala Val
        1205                1210                1215

Glu Leu Val Trp Val Thr Arg Gly Ala Val Ser Ala Ala Pro Asp Asp
        1220                1225                1230

Ala Val Glu Asp Leu Ala His Gly Pro Leu Trp Gly Leu Ile Arg Thr
        1235                1240                1245

Ala Arg Ser Glu His Pro Glu Arg Arg Leu Arg Leu Ile Asp Val Gly
        1250                1255                1260

Thr Glu Pro Val Asp Ala Gly Leu Leu Ala Arg Ala Leu Ala Thr Ala
1265                1270                1275                1280

Ala Glu Pro Glu Leu Ala Leu Arg Gly Gly Ala Val Leu Ala Ala Arg
        1285                1290                1295

Leu Val Arg Val Gln Ala Ala Ala Glu Glu Leu Thr Arg Ala Arg Gly
        1300                1305                1310

Leu Asp Pro Ala Gly Thr Val Leu Val Thr Gly Ala Val Gly Gly Leu
        1315                1320                1325

Gly Gln Ala Val Thr Arg His Leu Val Arg Ala His Gly Val Arg His
        1330                1335                1340

Leu Val Leu Thr Ser Arg Arg Gly Leu Glu Ala Pro Gly Ala Arg Glu
1345                1350                1355                1360

Leu Val Gln Ser Leu Glu Glu Leu Gly Ala Glu Thr Val Ser Met Val
        1365                1370                1375

Ala Cys Asp Val Ser Lys Arg Glu Glu Ile Ala Arg Val Leu Ala Gly
        1380                1385                1390

Ile Asp Ala Ala Arg Pro Leu Ser Ala Val Leu His Leu Ala Gly Val
        1395                1400                1405

Val His Asp Gly Val Ile Gln Thr Gln Thr Ala Glu Arg Leu Ala Trp
        1410                1415                1420

Val Leu Ala Pro Lys Val Asp Gly Ala Leu His Leu His Glu Leu Thr
1425                1430                1435                1440

Arg Glu Leu Asp Leu Ala Ala Phe Val Leu Phe Ser Ser Ala Ala Gly
        1445                1450                1455

Thr Leu Gly Met Ala Gly Gln Gly Asn Tyr Ala Ala Ala Asn Thr Phe
        1460                1465                1470

Leu Asp Ala Phe Ala Ala His Arg Arg Gly Arg Gly Leu Ala Ala Thr
        1475                1480                1485

Ser Leu Ala Trp Gly Val Trp Thr Pro Ala Gly Gly Gly Met Ala Ala
        1490                1495                1500

Gln Leu Gly Ala Ala Glu Leu Ala Arg Phe Ser Arg Tyr Gly Val Val
1505                1510                1515                1520

Ser Met Ser Val Glu Glu Gly Leu Ser Leu Leu Asp Ala Ala Leu Ser
        1525                1530                1535

Arg Pro Glu Ala Ser Leu Val Pro Met His Leu Asp Leu Ala Gln Leu
        1540                1545                1550

Gln Arg Gly Leu Glu Ala Asn Gly Glu Leu Pro Ala Leu Phe Arg Ala
        1555                1560                1565

Leu Leu Arg Pro Ser Leu Arg Lys Ala Ser Thr Ala Thr Arg Arg Asp
        1570                1575                1580

Ala Ser Ala Leu Arg Gly Arg Leu Ser Ala Leu Pro Glu Ala Glu Arg
1585                1590                1595                1600

Leu Asn Ala Leu Ile Glu Leu Val Arg Gly Glu Val Ala Ala Val Leu
        1605                1610                1615

Gly Leu Gln Arg Ser Glu Ala Val Gly Ala Glu Gln Val Leu Lys Gly
```

-continued

```
              1620                1625                1630
Leu Gly Leu Asp Ser Leu Met Ala Val Glu Leu Arg Asn Arg Leu Ala
        1635                1640                1645

Ala Arg Thr Glu Thr Ser Leu Pro Ala Thr Leu Val Phe Asp Tyr Pro
    1650                1655                1660

Thr Pro Arg Ala Ile Ala Glu Leu Leu Leu Lys Leu Ala Phe Ser Gly
1665                1670                1675                1680

Pro Gln Val Met Gly Ala Arg Arg Gly Val Arg Arg His Ala Gly Lys
            1685                1690                1695

Asp Glu Ala Val Ala Ile Val Ser Met Ala Cys Arg Leu Pro Gly Gly
        1700                1705                1710

Val Glu Thr Pro Glu Asp Tyr Trp Arg Leu Leu Ala Glu Gly Lys Asp
        1715                1720                1725

Val Ile Glu Gly Leu Pro Ala Arg Trp Glu Thr Leu Ser Val Tyr Asp
    1730                1735                1740

Pro Asp Pro Glu Ala Val Gly Lys Ser Tyr Ala Arg Glu Gly Gly Phe
1745                1750                1755                1760

Leu Arg Asp Ile Asp Leu Phe Asp Ala Asp Phe Phe Gly Ile Ser Pro
        1765                1770                1775

Arg Glu Ala Gln Ala Met Asp Pro Gln Gln Arg Leu Val Leu Glu Thr
    1780                1785                1790

Ala Trp Glu Ala Leu Glu Arg Ala Gly Val Arg Pro Ser Ala Leu Ser
        1795                1800                1805

Gly Ser Ala Thr Gly Val Tyr Leu Gly Ala Ala Gly Ser Asp Tyr Gly
    1810                1815                1820

Ala Tyr Gln Gly Gly Gly Leu Glu Met Leu Asp Gly Tyr Arg Gly Ile
1825                1830                1835                1840

Gly Ser Ala Ala Ser Val Leu Ser Gly Arg Val Ala Tyr Val Leu Gly
        1845                1850                1855

Leu His Gly Pro Ala Met Thr Val Asp Thr Ala Cys Ser Ser Ser Leu
            1860                1865                1870

Val Ser Leu His Leu Ala Cys Thr Ala Leu Arg Gln Gly Glu Cys Asp
        1875                1880                1885

Leu Ala Leu Ala Gly Gly Val Thr Val Met Ser Thr Pro Ala Leu Phe
    1890                1895                1900

Val Glu Phe Ser Arg Leu Lys Gly Met Ala Arg Asp Gly Arg Cys Lys
1905                1910                1915                1920

Ser Phe Ser Gly Gln Ala Asp Gly Ala Gly Trp Ser Glu Gly Cys Gly
            1925                1930                1935

Met Leu Val Leu Lys Arg Leu Ser Asp Ala Arg Arg Asp Gly Asp Arg
        1940                1945                1950

Val Leu Ala Val Val Arg Gly Ser Ala Val Asn Gln Asp Gly Arg Ser
    1955                1960                1965

Gln Gly Leu Thr Ala Pro Asn Gly Pro Ala Gln Gln Arg Val Ile Gln
    1970                1975                1980

Gln Ala Leu Ser Ser Cys Gly Leu Ser Pro Glu Asp Ile Asp Ala Val
1985                1990                1995                2000

Glu Ala His Gly Thr Gly Thr Ser Leu Gly Asp Pro Ile Glu Ala Gly
            2005                2010                2015

Ala Leu Ala Glu Val Phe Gly Pro Gly Arg Lys Ala Glu Arg Pro Leu
            2020                2025                2030

Tyr Leu Gly Ser Ser Lys Ser Asn Leu Gly His Ala Gln Ala Ala Ala
            2035                2040                2045
```

-continued

```
Gly Val Ala Gly Val Leu Lys Met Val Leu Ser Met Gln His Glu Val
    2050                2055                2060
Leu Pro Lys Thr Leu His Ala Glu Gln Pro Ser Pro His Ile Gly Trp
2065            2070                2075                2080
Glu Gly Ser Gly Leu Ser Leu Leu Gln Glu Ala Arg Pro Trp Arg Arg
        2085                2090                2095
Asn Gly Arg Ala Arg Arg Ala Gly Val Ser Ser Phe Gly Ile Ser Gly
        2100                2105                2110
Thr Asn Ala His Val Ile Leu Glu Glu Ala Pro Val Glu Ala Ala Arg
        2115                2120                2125
Glu Pro Val Glu Ala Val Arg Glu Pro Val Glu Ala Glu Gly Val Ala
    2130                2135                2140
Ile Pro Leu Leu Leu Ser Gly Arg Asp Glu Ala Ser Val Ala Ala Gln
2145            2150                2155                2160
Ala Gly Arg Trp Ala Lys Trp Leu Glu Glu His Gly Glu Val Gly Trp
        2165                2170                2175
Ser Asp Val Val Arg Thr Ala Ala Leu His Arg Thr His Phe Glu Ser
        2180                2185                2190
Arg Ala Ser Val Leu Ala Ala Ser Ala Ala Gly Ala Val Glu Gly Leu
        2195                2200                2205
Arg Ala Leu Ser Ser Gly Arg Pro Asp Ala Ala Val Val Ser Gly Thr
    2210                2215                2220
Ala Lys Arg Gly Gly Lys Leu Ala Val Leu Phe Thr Gly Gln Gly Ser
2225            2230                2235                2240
Gln Arg Leu Gly Met Gly Lys Arg Leu Tyr Glu Val Tyr Pro Val Phe
        2245                2250                2255
Arg Ala Ala Phe Asp Glu Val Cys Glu Ala Leu Asp Ala His Leu Asp
        2260                2265                2270
Arg Gly Leu Arg Glu Val Val Phe Ala Ala Ala Gly Ser Glu Glu Gly
        2275                2280                2285
Ala Leu Leu Glu Arg Thr Glu Tyr Thr Gln Pro Gly Leu Phe Ala Leu
    2290                2295                2300
Glu Val Ala Leu Tyr Arg Gln Trp Glu Ser Gly Leu Lys Pro Ala Ala
2305            2310                2315                2320
Leu Leu Gly His Ser Ile Gly Glu Leu Ser Ala Ala His Val Ala Gly
        2325                2330                2335
Val Leu Ser Leu Ala Asp Ala Ala Lys Leu Val Cys Ala Arg Gly Arg
        2340                2345                2350
Leu Met Gln Gly Cys Glu Ala Gly Gly Ala Met Val Ser Val Glu Ala
    2355                2360                2365
Ser Glu Pro Asp Val Gln Arg Ala Leu Ser Glu Val Gly Ala Gln Gly
    2370                2375                2380
Arg Leu Ser Ile Ala Gly Leu Asn Ala Pro Met Gln Thr Val Leu Ser
2385            2390                2395                2400
Gly Asp Glu Ala Ala Val Leu Ala Val Ala Arg Arg Leu Glu Ala Gln
            2405                2410                2415
Gly Arg Arg Thr Arg Arg Leu Arg Val Ser His Ala Phe His Ser Ala
        2420                2425                2430
His Met Asp Gly Met Leu Glu Glu Phe Gly Lys Val Ala Arg Gly Cys
        2435                2440                2445
Thr Tyr Ala Arg Pro Arg Leu Ala Val Val Ser Gly Val Thr Gly Glu
    2450                2455                2460
```

-continued

```
Leu Gly Gly Glu Glu Ala Leu Met Ser Ala Glu Tyr Trp Val Arg Gln
2465                2470                2475                2480

Val Arg Glu Ala Val Arg Phe Leu Asp Gly Met Arg Thr Leu Ala Ala
            2485                2490                2495

Ala Gly Val Ser Thr Tyr Val Glu Cys Gly Pro Asp Gly Val Leu Cys
        2500                2505                2510

Ala Leu Gly Ala Gly Cys Leu Pro Glu Gly Ala Glu Ala Thr Phe Val
    2515                2520                2525

Thr Ser Leu Arg Arg Glu Gln Glu Glu Glu Arg Ala Leu Ala Thr Ala
    2530                2535                2540

Val Ala Thr Val His Val Gln Gly His Glu Val Asp Trp Ala Gln Val
2545                2550                2555                2560

Leu Ser Gly Arg Gly Gly Arg Pro Val Glu Leu Pro Thr Tyr Ala Phe
            2565                2570                2575

Gln Arg Gln Arg Tyr Trp Leu Glu Ala Pro Lys Thr Thr Ala Ala Gln
            2580                2585                2590

Ala Asn Val Ser Trp Pro Glu Arg Ala Leu Trp Asp Ala Val Gln Lys
        2595                2600                2605

Gly Glu Gly Val Ala Asp Leu Leu Glu Leu Pro Asp Asp Val Arg Glu
    2610                2615                2620

Ser Val Ala Pro Leu Leu Pro Tyr Leu Ala Ala Trp Arg Arg Arg Arg
2625                2630                2635                2640

Asp Ala Glu Ala Thr Val Ser Gly Trp Leu Tyr Glu Glu Ala Trp Gln
            2645                2650                2655

Arg Glu Ala Ser Ala Ala Arg Gly Lys Pro Asp Val Arg Gly Arg Trp
            2660                2665                2670

Leu Leu Val Ser Ser Pro Arg Ala Gly Gly Leu Thr Ala Ala Val Ser
        2675                2680                2685

Asp Ala Leu Gly Ala Ala Gly Ala Glu Val Ile Ile Glu Pro Ala Thr
    2690                2695                2700

Glu Glu Arg Ala Gln Leu Ala Ala Arg Leu Arg Gly Leu Glu Gly Glu
2705                2710                2715                2720

Leu Arg Gly Val Val Ala Leu Ser Ala Pro Gly Glu Gln Gly Ala Leu
            2725                2730                2735

Glu Glu Gly Arg Gly Pro Arg Gly Val Tyr Glu Val Leu Ala Leu Ala
            2740                2745                2750

Gln Ala Leu Gly Asp Ala Gly Leu Asp Ala Arg Leu Trp Val Leu Thr
        2755                2760                2765

Gln Gly Ala Val Ser Thr Glu Ala Ser Glu Gly Val Ser Asp Pro Ala
    2770                2775                2780

Gln Ala Leu Thr Trp Gly Leu Gly Arg Val Val Gly Leu Glu His Pro
2785                2790                2795                2800

Glu Arg Trp Gly Gly Leu Val Asp Leu Pro Ala Glu Val Asp Ala Glu
            2805                2810                2815

Ala Val Gln Gln Val Leu Arg Thr Leu Val Ala Glu Asp His Glu Asp
            2820                2825                2830

Gln Val Ala Val Arg Arg Gly Gly Arg Leu Val Arg Arg Ile Val Arg
        2835                2840                2845

Val Ser Gly Glu Asp Gly Gly Ala Gly Trp Lys Pro Arg Gly Thr Val
    2850                2855                2860

Leu Ile Thr Gly Gly Val Gly Gly Leu Gly Ser His Leu Ala Arg Trp
2865                2870                2875                2880

Leu Ala Glu Arg Gly Ala Glu His Leu Val Leu Ala Ser Arg Arg Gly
```

```
                       2885                   2890                   2895
Ala Ala Ala Ala Gly Ala Arg Glu Leu Arg Glu Glu Leu Glu Gly Arg
                   2900                   2905                   2910
Gly Ala Arg Val Thr Leu Ala Ala Cys Asp Val Ser Glu Arg Ala Gln
                   2915                   2920                   2925
Val Glu Ala Leu Val Arg Glu Leu Glu Gln Asp Glu Ala Pro Leu Ser
                   2930                   2935                   2940
Ala Val Ala His Leu Ala Gly Ile Val Arg Arg Val Pro Val Arg Glu
2945                   2950                   2955                   2960
Leu Ala Pro Glu Met Leu Ala Gln Glu Leu Ala Ala Lys Val Asn Gly
                   2965                   2970                   2975
Ala Trp His Leu Gln Glu Leu Leu Ala Glu Arg Glu Leu Asp Ala Phe
                   2980                   2985                   2990
Val Leu Tyr Gly Ser Ile Ala Gly Leu Trp Gly Ser Gly Thr Gln Ala
                   2995                   3000                   3005
Gly Tyr Gly Ala Ala Asn Ala Gly Leu Asp Ala Leu Ala Arg Tyr Arg
                   3010                   3015                   3020
Arg Ala Arg Gly Gln Thr Ala Thr Val Leu His Trp Gly Pro Trp Ser
3025                   3030                   3035                   3040
Gly Gly Gly Met Val Ser Asp Glu Ala Glu Pro Gln Leu Arg Ser Arg
                   3045                   3050                   3055
Gly Leu Val Pro Met Ser Pro Asp Lys Ala Leu Cys Gly Leu Glu Val
                   3060                   3065                   3070
Gly Leu Arg Arg Thr Ser Val Ala Ile Ala Asp Val Asp Trp Ser Arg
                   3075                   3080                   3085
Phe Ala Pro Leu Phe Cys Ala Ala Arg Pro Arg Pro Leu Leu Tyr Gly
                   3090                   3095                   3100
Ile Glu Gln Ala Arg His Ala Leu Glu Gly Arg Thr Pro Gln Gln Ala
3105                   3110                   3115                   3120
Ala Gly Gly Ala Gly Asp Lys Ala Leu Arg Glu Met Leu Leu Gly Leu
                   3125                   3130                   3135
Pro Ala Val Glu Arg Ser Glu Arg Leu Arg Glu Leu Val Ala Ser Glu
                   3140                   3145                   3150
Thr Ala Ala Val Leu Gly Val Lys Asp Pro Ser Gly Leu Asp Pro Glu
                   3155                   3160                   3165
Arg Gly Phe Leu Asp Leu Gly Leu Asp Ser Leu Met Ala Val Glu Leu
                   3170                   3175                   3180
Ser Lys Arg Leu Gln Gln Arg Thr Gly Val Ser Val Thr Arg Thr Leu
3185                   3190                   3195                   3200
Ile Phe Asp Tyr Pro Thr Gln Gly Glu Val Thr Arg Trp Leu Leu Glu
                   3205                   3210                   3215
Gln Leu Met Pro Pro Glu Arg Pro Ala Ala Asp Glu His Gly Val Ser
                   3220                   3225                   3230
Arg Gly Pro Glu Arg Ser Ala Pro Ile Ala Ile Val Gly Val Gly Leu
                   3235                   3240                   3245
Arg Met Pro Gly Gly Ala Asn Asp Leu Glu Ser Phe Trp Gln Val Leu
                   3250                   3255                   3260
Val Glu Gly Arg Asp Thr Leu Arg Pro Ile Pro Thr Asp Arg Phe Asp
3265                   3270                   3275                   3280
Val Glu Ala Met Tyr Asp Pro Asn Pro Glu Ala Lys Gly Lys Thr Tyr
                   3285                   3290                   3295
Val Lys His Ala Ser Leu Leu Asp Asp Val Ala Ser Phe Asp Ala Gly
                   3300                   3305                   3310
```

```
Phe Phe Gly Ile Ser Pro Arg Glu Ala Glu Pro Met Asp Pro Gln His
    3315                3320                3325
Arg Leu Leu Leu Glu Thr Ala Trp Ser Ala Leu Glu Asp Ala Gly Val
    3330                3335                3340
Arg Pro Asp Gln Leu Lys Gly Ser Asp Thr Gly Val Phe Val Gly Val
3345                3350                3355                3360
Ala Pro Ser Glu Tyr Ala Ser Tyr Arg Gly Lys Ser Ala Asn Glu Asp
                3365                3370                3375
Ala Tyr Ala Leu Thr Gly Thr Ala Leu Ser Phe Ala Ala Gly Arg Val
                3380                3385                3390
Ala Tyr His Leu Gly Leu Gln Gly Pro Ala Val Ser Val Asp Thr Ala
            3395                3400                3405
Cys Ser Ser Ser Leu Val Ala Leu His Leu Ala Cys Asp Ala Leu Arg
    3410                3415                3420
Arg Gly Asp Cys Glu Val Ala Leu Ala Ala Gly Val Gln Val Leu Ala
3425                3430                3435                3440
Asn Pro Ala Gly Phe Val Leu Leu Ser Arg Thr Arg Ala Val Ser Pro
            3445                3450                3455
Asp Gly Arg Cys Lys Thr Phe Ser Gln Ala Ala Asp Gly Tyr Gly Arg
            3460                3465                3470
Gly Glu Gly Val Gly Val Val Leu Met Arg Leu Ser Asp Ala Gln
    3475                3480                3485
Ala Gln Gly Met Arg Val Leu Gly Val Val Arg Gly Thr Ala Val Asn
    3490                3495                3500
Gln Asp Gly Ala Ser Ser Gly Ile Thr Ala Pro Asn Gly Thr Ala Gln
3505                3510                3515                3520
Gln Lys Val Val Arg Ala Ala Leu Arg Asn Ala Gly Leu Glu Ala Ser
                3525                3530                3535
Ser Ile Asp Val Val Glu Cys His Gly Thr Gly Thr Ser Leu Gly Asp
            3540                3545                3550
Pro Ile Glu Val Gln Ala Leu Gly Ala Val Tyr Gly Gln Gly Arg Glu
    3555                3560                3565
Ala Thr Arg Pro Leu Arg Leu Gly Ala Val Lys Ser Asn Ile Gly His
    3570                3575                3580
Leu Glu Ser Ala Ala Gly Ile Ala Gly Val Cys Lys Ile Leu Ala Ala
3585                3590                3595                3600
Phe Arg His Glu Ala Leu Pro Ala Thr Leu His Ser Ser Pro Arg Asn
            3605                3610                3615
Pro Gln Ile Ser Trp Glu Ser Leu Pro Val Gln Val Asp Arg Leu
    3620                3625                3630
Thr Gly Trp Pro Arg Arg Ala Asp Gly Leu Pro Arg Phe Ala Gly Val
            3635                3640                3645
Ser Ser Phe Gly Ile Ser Gly Thr Asn Ala His Val Ile Leu Glu Glu
    3650                3655                3660
Ala Pro Leu Glu Ala Val Arg Glu Pro Ala Ala Val Arg Glu Pro Leu
3665                3670                3675                3680
Ala Ala Glu Gly Val Ala Ile Pro Leu Leu Leu Ser Gly Arg Asp Glu
            3685                3690                3695
Ala Ser Val Gly Ala Gln Ala Glu Arg Trp Ala Lys Trp Leu Gly Glu
            3700                3705                3710
His Ala Glu Val Arg Trp Pro Asp Val Val Arg Thr Ala Ala Leu His
    3715                3720                3725
```

-continued

```
Arg Thr His Phe Ala Trp Arg Ala Ser Val Gln Ala Ala Ser Val Ser
    3730                3735                3740
Glu Ala Val Glu Gly Leu Arg Ala Leu Ser Glu Gly Arg Ala Ala Ala
3745                3750                3755                3760
Gly Val Val Arg Gly Thr Gly Arg Gly Gly Lys Leu Ala Val Leu
            3765                3770                3775
Phe Thr Gly Gln Gly Ser Gln Arg Leu Gly Met Gly Lys Arg Leu Tyr
            3780                3785                3790
Glu Val Tyr Pro Val Phe Arg Ala Ala Phe Asp Glu Val Cys Glu Ala
        3795                3800                3805
Leu Asp Ala His Leu Asp Arg Gly Leu Arg Glu Val Val Phe Ala Glu
        3810                3815                3820
Ala Gly Ser Glu Gln Glu Ala Leu Leu Glu Arg Thr Glu Tyr Thr Gln
3825                3830                3835                3840
Pro Gly Leu Phe Ala Leu Glu Val Ala Leu Tyr Arg Gln Trp Glu Ala
            3845                3850                3855
Trp Gly Val Arg Pro Ala Ala Leu Leu Gly His Ser Ile Gly Glu Leu
        3860                3865                3870
Ser Ala Ala His Val Ala Gly Val Leu Ser Leu Ala Asp Ala Ala Lys
        3875                3880                3885
Leu Val Cys Ala Arg Gly Arg Leu Met Gln Arg Cys Gln Ala Gly Gly
    3890                3895                3900
Ala Met Met Ser Val Glu Ala Ser Glu Pro Glu Val Gln Gly Ala Leu
3905                3910                3915                3920
Ser Ala Met Gly Leu Glu Gly Arg Leu Gly Ile Ala Gly Ile Asn Gly
            3925                3930                3935
Pro Ser Gln Thr Val Leu Ser Gly Asp Glu Ala Ala Val Leu Glu Val
        3940                3945                3950
Gly Arg Arg Phe Glu Ala Gln Gly Arg Arg Thr Arg Arg Leu Arg Val
            3955                3960                3965
Ser His Ala Phe His Ser Ala His Met Asp Gly Met Leu Glu Glu Tyr
    3970                3975                3980
Gly Arg Val Ala Arg Glu Cys Ala Tyr Gly Arg Pro Gln Val Pro Val
3985                3990                3995                4000
Val Ser Gly Val Thr Gly Glu Leu Gly Gly Glu Glu Ser Leu Met Ser
            4005                4010                4015
Ala Glu Tyr Trp Val Arg Gln Val Arg Glu Ala Val Arg Phe Leu Asp
            4020                4025                4030
Gly Met Arg Thr Leu Ala Ala Ala Gly Val Ser Thr Tyr Val Glu Cys
        4035                4040                4045
Gly Pro Asp Gly Val Leu Cys Ala Leu Gly Ala Gly Cys Leu Pro Glu
    4050                4055                4060
Gly Ala Glu Ala Thr Phe Val Ala Ser Leu Arg Arg Glu Gln Glu Glu
4065                4070                4075                4080
Glu Arg Ala Leu Val Thr Ala Val Ala Thr Val His Val Gln Gly His
            4085                4090                4095
Glu Val Asp Trp Ala Gln Val Leu Ser Gly His Gly Gly Arg Pro Val
        4100                4105                4110
Glu Leu Pro Thr Tyr Ala Phe Gln Arg Gln Arg Tyr Trp Leu Glu Ala
        4115                4120                4125
Pro Arg Ala Arg Gly Asp Val Gly Ser Ala Gly Leu Lys Ala Ala Ala
    4130                4135                4140
His Pro Leu Leu Gly Ala Ala Thr Lys Leu Ala Asp Gly Glu Gly His
```

-continued

```
           4145                4150                4155                4160
Leu Phe Thr Gly Arg Leu Ser Leu Ala Glu His Ala Trp Leu Arg Asp
                    4165                4170                4175
His Gln Val Phe Gly Lys Val Val Phe Pro Gly Thr Gly Met Leu Glu
                    4180                4185                4190
Leu Ala Leu Ala Ala Gly Arg Ala Val Gly Ser Arg Thr Leu Ser Glu
           4195                4200                4205
Leu Val Leu Ala Glu Pro Leu Val Leu Ala Glu Glu Ala Ala Ala Arg
      4210                4215                4220
Leu Gln Leu Ser Val Gly Ala Pro Asp Ala Ala Gly Arg Arg Glu Val
4225                4230                4235                4240
Gly Leu Tyr Ser Gln Ser Glu Gln Ala Pro Glu Asp Ala Pro Trp Val
                    4245                4250                4255
Gln His Ala Thr Gly Val Leu Thr Asp Glu Ile Pro Gly Ala Pro Gly
                    4260                4265                4270
Glu Leu Asp Glu Leu Ser Thr Trp Pro Val Pro Gly Ala Glu Glu Val
           4275                4280                4285
Asp Leu Ser Gly Phe Tyr Glu Arg Leu Arg Glu Gly Gly Leu Asp Tyr
      4290                4295                4300
Gly Pro Val Phe Gln Gly Leu Val Glu Leu Trp Arg Arg Gly Ala Arg
4305                4310                4315                4320
Leu Tyr Gly Arg Val Val Leu Pro Gly Ser Ala Arg Gly Ser Ala Glu
                    4325                4330                4335
Ala Tyr Gly Val His Pro Ala Leu Met Asp Ala Ala Leu His Thr Met
                    4340                4345                4350
Val Ala Ala Phe Ser Gln Met Ser Gly Pro Asp Gly Val Leu Leu Pro
           4355                4360                4365
Phe Ala Trp Ser Asp Val Ala Pro His Ala Thr Gly Ala Ser Glu Leu
      4370                4375                4380
Arg Ile Arg Val Glu Met Gln Glu Gln Ser Ala Gln Gln Pro Ala Ala
4385                4390                4395                4400
Ser Leu Tyr Val Ala Asp Cys Thr Gly Gln Val Val Ala Ser Ile Gly
                    4405                4410                4415
Ala Leu Arg Leu Arg Arg Ala Thr Ala Glu Gln Leu Arg Thr Ala Val
                    4420                4425                4430
His Ala Gly Gly Gln His Met Tyr Gln Val Ser Phe Gln Pro Val Asp
           4435                4440                4445
Leu Ala Ala Pro Pro Leu Val Thr Gly Ser Leu Val Val Ile Gly Ala
      4450                4455                4460
Pro Lys Gly Gly Ala Arg Leu Ala Glu Ala Leu Gly Ala Glu Ala Ile
4465                4470                4475                4480
Ala Asp Leu Asp Ala Leu Val Val Arg Leu Glu His Gly Ala Ser Ala
                    4485                4490                4495
Pro Glu Arg Val Val Val Asp Val Thr Ala Ala Ser Pro Ser Pro Leu
                    4500                4505                4510
Asp Val Ala Gly Ser Ser His Glu Ala Thr Arg Gln Ala Leu Ser Leu
           4515                4520                4525
Leu Gln Ala Trp Leu Ser Glu Pro Arg Leu Glu Ala Thr Glu Leu Val
      4530                4535                4540
Trp Ile Thr Arg Gly Ala Val Gly Ala Ala Pro Asp Asp Ala Val Glu
4545                4550                4555                4560
Asp Leu Ala Arg Ala Pro Leu Trp Gly Leu Val Arg Ala Ala Arg Ser
                    4565                4570                4575
```

```
Glu His Pro Glu Arg Gly Leu Arg Leu Met Asp Val Gly Thr Glu Pro
            4580                4585                4590

Val Asp Ala Gly Leu Leu Ala Arg Ala Leu Ala Thr Ala Ala Glu Pro
        4595                4600                4605

Glu Leu Ala Leu Arg Gly Gly Ala Ala Leu Ala Ala Arg Leu Val Arg
    4610                4615                4620

Ala Gln Ala Val Ala Glu Glu Leu Thr Arg Ala Arg Glu Leu Asp Pro
4625                4630                4635                4640

Ala Gly Thr Val Leu Val Thr Gly Gly Thr Gly Glu Leu Gly Gln Ala
        4645                4650                4655

Val Ala Ala His Leu Val Arg Ala His Gly Val Arg His Leu Val Leu
            4660                4665                4670

Thr Ser Arg Arg Gly Leu Glu Ala Pro Gly Ala Arg Glu Leu Val Glu
    4675                4680                4685

Ser Leu Ala Glu Leu Gly Ala Glu Thr Val Thr Val Ala Ala Cys Asp
    4690                4695                4700

Val Ser Lys Arg Glu Glu Val Ala Arg Val Leu Ala Gly Ile Asp Ala
4705                4710                4715                4720

Ala Arg Pro Leu Ser Ala Val Leu His Leu Ala Gly Ala Leu Asp Asp
        4725                4730                4735

Gly Val Leu Ala Gly Gln Thr Ala Glu Arg Leu Ser Arg Val Leu Ala
        4740                4745                4750

Pro Lys Val Asp Gly Ala Leu His Leu His Glu Leu Thr Arg Glu Leu
    4755                4760                4765

Asp Leu Val Ala Phe Val Leu Phe Ser Ser Val Ala Gly Thr Phe Gly
    4770                4775                4780

Thr Ala Gly Gln Ser Asn Tyr Ala Ala Ala Asn Thr Phe Leu Asp Ala
4785                4790                4795                4800

Leu Ala Ala His Arg Arg Gly Cys Gly Leu Ala Ala Thr Ser Leu Ala
            4805                4810                4815

Trp Gly Leu Trp Ala Gln Ala Gly Val Gly Met Thr Ala His Leu Gly
        4820                4825                4830

Glu Ala Glu Leu Ser Arg Ile Arg Arg Ala Gly Leu Val Pro Ile Ser
        4835                4840                4845

Val Asp Glu Gly Leu Ala Leu Leu Asp Ala Ala Leu Ser Arg Ser Glu
    4850                4855                4860

Ala Ser Leu Val Pro Val His Leu Asp Leu Ala Gln Leu Gln Arg Gly
4865                4870                4875                4880

Leu Glu Ser Ser Gly Glu Leu Pro Ala Leu Leu Arg Ala Leu Val Arg
        4885                4890                4895

Pro Gly Leu Arg Lys Ala Ser Ser Ala Ala Arg Lys Glu Ala Ser Thr
            4900                4905                4910

Leu Arg Glu Arg Leu Ser Ala Leu Pro Glu Ala Glu Arg Leu Ser Ser
        4915                4920                4925

Leu Ile Asp Leu Val Arg Ala Glu Val Ala Ala Val Leu Gly Leu Gln
    4930                4935                4940

Arg Gly Asp Ala Ile Pro Thr Ala Gln Pro Leu Arg Glu Leu Gly Met
4945                4950                4955                4960

Asp Ser Leu Met Ala Val Glu Val Arg Asn Arg Leu Ala Leu Leu Val
            4965                4970                4975

Gly Ser Asn Leu Pro Ala Thr Leu Leu Phe Asp His Pro Ser Ala Thr
        4980                4985                4990
```

-continued

```
His Ile Ala Lys Phe Leu Leu Ser Lys Phe Gly Asn Gly Glu Arg Arg
       4995                5000                5005

Asn Leu Leu Arg Thr Ala Asp Ser Met Ser Asp Glu Glu Ile Arg Ala
   5010                5015                5020

Phe Met Leu Ser Leu Ser Val Ser Leu Val Arg Arg Ser Gly Leu Leu
5025               5030                5035                5040

Pro Lys Leu Leu Glu Leu Arg Gly Pro Ser Glu Thr Ser Val Glu Val
               5045                5050                5055

Pro Val Pro Ile Ser Asp Phe Glu Asp Leu Ala Asp Glu Gln Leu Ala
           5060                5065                5070

Leu Gln Ala Leu Gln Met Ile Ser Asn Ser Glu Asp Leu His Glu
       5075                5080                5085

<210> SEQ ID NO 2
<211> LENGTH: 6095
<212> TYPE: PRT
<213> ORGANISM: Sorangium cellulosum

<400> SEQUENCE: 2

Met Asn Ser Ser Ala Ala Ser Pro Thr Leu Arg Glu Ala Leu Thr Arg
  1               5                  10                  15

Ala Leu Lys Glu Leu Gln Arg Leu Gln Ala Ser His Ser Asp Leu Arg
             20                  25                  30

Ser Gly Pro Ile Ala Ile Val Ser Met Ala Cys Arg Leu Pro Gly Gly
        35                  40                  45

Val Ala Thr Pro Glu Asp Tyr Trp Arg Leu Leu Glu Glu Gly Arg Asp
     50                  55                  60

Ala Ile Glu Ala Phe Pro Ala Arg Trp Asp Ala Pro Ser Ile Tyr Asp
 65                  70                  75                  80

Pro Asp Pro Glu Ala Val Gly Lys Thr Tyr Val Arg Glu Gly Gly Phe
                 85                  90                  95

Leu Arg Asp Ile Asp Leu Phe Asp Ala Gly Phe Phe Gly Ile Ser Pro
            100                 105                 110

Arg Glu Ala Gln Ala Met Asp Pro Gln Gln Arg Leu Val Leu Glu Thr
        115                 120                 125

Ala Trp Glu Ala Leu Glu Arg Ala Gly Val Arg Pro Ser Ala Leu Ser
    130                 135                 140

Glu Ser Ser Thr Gly Val Tyr Leu Gly Ser Met Gly Ser Asp Tyr Gly
145                 150                 155                 160

Ala Leu Tyr Gly Ser Asp Leu Ala Ala Leu Asp Gly Tyr Arg Gly Thr
                165                 170                 175

Gly Ser Ala Ala Ser Val Leu Ser Gly Arg Val Ala Tyr Val Leu Gly
            180                 185                 190

Leu Gln Gly Pro Ala Ile Thr Val Asp Thr Ala Cys Ser Ser Ser Leu
        195                 200                 205

Val Ser Leu His Leu Ala Cys Thr Ala Leu Arg Gln Gly Glu Cys Asp
    210                 215                 220

Leu Ala Leu Thr Gly Gly Val Met Val Met Thr Thr Pro Ala Gly Phe
225                 230                 235                 240

Val Glu Phe Ser Arg Leu Lys Ala Leu Ala Arg Asp Gly Arg Cys Lys
                245                 250                 255

Ser Phe Ser Ala Arg Ala Asp Gly Val Ile Trp Ser Glu Gly Cys Gly
            260                 265                 270

Met Leu Val Leu Lys Arg Leu Ser Asp Ala Arg Arg Asp Gly Asp Arg
        275                 280                 285

```
Val Leu Ala Val Ile Arg Gly Ser Ala Val Asn Gln Asp Gly Arg Ser
290                 295                 300
Gln Gly Leu Thr Ala Pro Asn Gly Pro Ala Gln Gln Arg Val Ile Gln
305                 310                 315                 320
Gln Ala Leu Ser Ser Cys Arg Leu Ser Pro Glu Asp Ile Asp Ala Val
                325                 330                 335
Glu Ala His Gly Thr Gly Thr Asn Leu Gly Asp Pro Ile Glu Ala Gly
            340                 345                 350
Ala Leu Val Glu Val Phe Gly Pro Gly Arg Lys Ala Glu Arg Pro Leu
        355                 360                 365
Tyr Leu Gly Ser Ser Lys Ser Asn Leu Gly His Ala Gly Pro Ala Ala
370                 375                 380
Gly Val Ala Gly Val Leu Lys Met Val Leu Ser Met Gln His Glu Val
385                 390                 395                 400
Leu Pro Arg Thr Leu His Ala Glu Gln Pro Ser Pro His Ile Gly Trp
                405                 410                 415
Glu Gly Ser Gly Leu Ser Leu Leu Gln Glu Ala Arg Pro Trp Arg Arg
            420                 425                 430
Asn Gly Arg Ala Arg Arg Ala Gly Val Ser Ser Phe Gly Ile Ser Gly
        435                 440                 445
Thr Asn Ala His Val Ile Leu Glu Glu Ala Pro Val Glu Ala Ala Arg
    450                 455                 460
Glu Pro Val Glu Ala Met Arg Glu Pro Leu Ala Thr Glu Gly Val Ala
465                 470                 475                 480
Met Pro Leu Leu Leu Ser Gly Arg Asp Glu Ala Ser Val Gly Ala Gln
                485                 490                 495
Ala Glu Arg Trp Ala Lys Trp Leu Gly Glu His Gly Glu Val Gln Trp
            500                 505                 510
Ser Asp Val Val Arg Thr Ala Ala Leu His Arg Thr His Phe Ala Ser
        515                 520                 525
Arg Ala Ser Val Leu Ala Ala Ser Val Ser Glu Ala Glu Glu Ala Leu
    530                 535                 540
Arg Ala Leu Ser Gln Gly Arg Gly His Arg Ala Val Ser Ala Gly Thr
545                 550                 555                 560
Ala Arg Ala Arg Gly Lys Val Phe Val Phe Pro Gly Gln Gly Ser
                565                 570                 575
Gln Trp Pro Gly Met Gly Arg Ala Leu Leu Glu Gln Ser Ala Ala Phe
            580                 585                 590
Ala Glu Ala Val Gln Ala Cys Asp Glu Ala Leu Arg Pro Trp Thr Gly
        595                 600                 605
Trp Ser Val Leu Ser Val Leu Arg Gly Asp Gly Glu Glu Gln Pro
    610                 615                 620
Ser Leu Glu Arg Val Asp Val Val Gln Pro Ala Leu Phe Ala Met Cys
625                 630                 635                 640
Val Gly Leu Ala Ala Ala Trp Arg Ser Leu Gly Leu Glu Pro Ala Ala
                645                 650                 655
Val Val Gly His Ser Gln Gly Glu Val Ser Ala Ala Val Val Cys Gly
            660                 665                 670
Ala Leu Ser Leu Ala Glu Gly Ala Arg Val Val Ala Leu Arg Ser Gln
        675                 680                 685
Ala Val Arg Gln Arg Ser Gly Met Gly Ala Met Met Leu Val Glu Arg
    690                 695                 700
```

-continued

```
Pro Val Ser Glu Val Gln Glu Arg Ile Ala Pro Tyr Gly Glu Ala Leu
705                 710                 715                 720

Ala Ile Ala Ala Val Asn Thr Ser Ser Thr Val Ser Gly Asp
                725                 730                 735

Val Glu Ala Val Asp Gly Leu Met Val Glu Leu Thr Ala Glu Gly Val
                740                 745                 750

Phe Cys Arg Lys Val Asn Val Asp Tyr Ala Ser His Ser Ala His Met
                755                 760                 765

Asp Ala Leu Leu Pro Glu Leu Gly Ala Lys Leu Ser Ser Leu Arg Pro
770                 775                 780

Lys Ala Thr Gln Leu Pro Phe Tyr Ser Thr Val Thr Gly Glu Val Ser
785                 790                 795                 800

Arg Gly Glu Ala Leu Asp Gly Glu Tyr Trp Cys Arg Asn Leu Arg Arg
                805                 810                 815

Thr Val Arg Leu Asp Arg Ala Leu Ser Lys Leu Leu Glu Asp Gly His
                820                 825                 830

Gly Val Phe Val Glu Val Ser Ala His Pro Val Leu Ala Met Pro Leu
                835                 840                 845

Thr Thr Ala Cys Gly Glu Ala Gln Gly Val Val Gly Ser Leu Gln
850                 855                 860

Arg Asp Glu Gly Gly Leu Ser Gln Leu Tyr Arg Thr Leu Gly Gln Leu
865                 870                 875                 880

His Val Gln Gly His Glu Val Asp Trp Thr Arg Val Leu Ser Gly His
                885                 890                 895

Gly Gly Arg Val Val Glu Leu Pro Thr Tyr Ala Phe Gln Arg Gln Arg
                900                 905                 910

Tyr Trp Leu Asp Ile Ser Lys Ala Arg Ser Asp Val Ser Ser Ala Gly
                915                 920                 925

Leu Lys Ala Ala His Pro Leu Leu Gly Ala Ala Thr Arg Leu Ala
930                 935                 940

Asp Gly Glu Gly His Leu Phe Thr Gly Arg Leu Ser Leu Ala Glu His
945                 950                 955                 960

Pro Trp Leu Arg Asp His Glu Val Phe Gly Gln Val Val Leu Pro Gly
                965                 970                 975

Thr Gly Thr Leu Glu Leu Val Leu Ala Ala Gly Arg Ala Val Gly Ser
                980                 985                 990

Arg Ser Leu Ser Glu Leu Thr Leu Ala Glu Pro Leu Val Leu Ala Glu
                995                 1000                1005

Gly Ala Ala Arg Leu Gln Val Met Ile Gly Ala Pro Asp Ala Ala Gly
        1010                1015                1020

Arg Arg Glu Val Gly Leu Tyr Ser Gln Pro Glu Gln Ala Pro Glu Asp
1025                1030                1035                1040

Ala Pro Trp Val Gln His Ala Thr Gly Val Leu Thr Asp Glu Pro Pro
                1045                1050                1055

Gly Ile Pro Val Glu Leu Asp Glu Leu Ser Thr Trp Pro Val Pro Gly
        1060                1065                1070

Ala Glu Glu Val Asp Leu Ser Gly Leu Tyr Glu Arg Leu Arg Glu Arg
        1075                1080                1085

Gly Leu His Tyr Gly Pro Ala Phe Gln Gly Leu Val Glu Leu Ser Arg
        1090                1095                1100

Gln Gly Thr Thr Tyr Phe Gly Arg Val Val Leu Pro Gly Thr Glu Lys
1105                1110                1115                1120

Asp Arg Ala Glu Ala Tyr Gly Val His Pro Ala Leu Met Asp Ala Ala
```

-continued

```
                1125                1130                1135
Leu His Thr Met Val Ala Ala Phe Ser Glu Ser Pro Gly Ala Asn Glu
            1140                1145                1150
Val Leu Val Pro Phe Ala Trp Ser Asp Val Ala Leu His Ala Thr Gly
        1155                1160                1165
Ala Ser Glu Leu Arg Val Arg Val Glu Leu Gln Asp Gly Gly Ala His
    1170                1175                1180
Gln Asp Thr Ala Ser Leu Gln Val Ala Asp Ser Thr Gly Gln Ala Val
1185                1190                1195                1200
Ala Ser Ile Gly Ala Leu His Leu Arg Arg Ala Thr Ala Glu Gln Leu
            1205                1210                1215
Arg Thr Ala Val His Ala Gly Gly Gln His Met Tyr Gln Val Ser Phe
            1220                1225                1230
Gln Pro Val Glu Leu Ala Ala Ala Pro Leu Glu Ala Gly Ser Leu Val
        1235                1240                1245
Val Val Gly Ala Ala Glu Gly Arg Gly Arg Leu Ala Glu Ala Leu Arg
        1250                1255                1260
Ala Glu Ala Ile Ala Asp Leu Glu Ala Leu Val Ala Arg Leu Glu Gln
1265                1270                1275                1280
Gly Ala Ser Ala Pro Ala Arg Val Ala Val Asp Thr Thr Ala Leu Gly
            1285                1290                1295
Gln Ser Gln Ser Gly Val Ala Ser Leu Ser His Glu Ala Thr Arg Gln
        1300                1305                1310
Ala Leu Ser Leu Leu Gln Ala Trp Leu Ser Glu Pro Arg Leu Asp Ala
        1315                1320                1325
Val Glu Leu Val Trp Val Thr Arg Gly Ala Val Gly Ala Ala Pro Asp
    1330                1335                1340
Asp Ala Val Gln Asp Leu Ala Arg Ala Pro Leu Trp Gly Leu Val Arg
1345                1350                1355                1360
Ala Ala Arg Ser Glu His Pro Glu Arg Arg Leu Arg Leu Ile Asp Val
            1365                1370                1375
Gly Thr Glu Pro Val Asp Ala Gly Leu Leu Ala Arg Ala Leu Ala Thr
        1380                1385                1390
Ala Ala Glu Pro Glu Leu Ala Leu Arg Gly Gly Ala Ala Leu Ala Ala
    1395                1400                1405
Arg Leu Val Arg Ala Gln Ala Ala Ala Glu Glu Leu Thr Arg Gly Ala
    1410                1415                1420
Arg Glu Leu Asp Pro Ala Gly Thr Val Leu Val Thr Gly Gly Thr Gly
1425                1430                1435                1440
Glu Leu Gly Gln Ala Ile Ala Ala His Leu Val Arg Ala His Gly Val
            1445                1450                1455
Arg His Leu Val Leu Thr Ser Arg Arg Gly Leu Glu Ala Pro Gly Ala
        1460                1465                1470
Arg Glu Leu Val Gln Ser Leu Glu Glu Leu Gly Ala Glu Thr Val Thr
        1475                1480                1485
Val Ala Ala Cys Asp Val Ser Lys Arg Glu Glu Val Ala Arg Val Leu
    1490                1495                1500
Ala Gly Ile Asp Ala Ala Arg Pro Leu Ser Ala Val Leu His Leu Ala
1505                1510                1515                1520
Gly Val Leu Asp Asp Gly Val Leu Thr Ala Gln Thr Ala Glu Arg Leu
            1525                1530                1535
Ser Arg Val Leu Ala Pro Lys Val Asp Gly Ala Leu His Leu His Glu
            1540                1545                1550
```

-continued

```
Leu Thr Arg Glu Leu Asp Leu Ala Ala Phe Val Leu Phe Ser Ser Ala
        1555                1560                1565
Ala Gly Thr Phe Gly Ala Ala Gly Gln Ser Asn Tyr Ala Ala Ala Asn
    1570                1575                1580
Thr Phe Leu Asp Ala Leu Ala Ala His Arg Arg Gly Gly Gly Leu Ala
1585                1590                1595                1600
Ala Thr Ser Leu Ala Trp Gly Phe Trp Thr Gln Ala Gly Val Gly Met
            1605                1610                1615
Thr Ala His Leu Gly Glu Ala Glu Leu Ser Arg Met Arg Arg Asn Gly
        1620                1625                1630
Phe Val Pro Met Pro Val Glu Glu Gly Leu Ala Leu Leu Asp Ala Ala
    1635                1640                1645
Leu Ser Arg Pro Glu Ala Ser Leu Val Pro Val His Leu Asp Leu Ala
    1650                1655                1660
Gln Leu Gln Arg Gly Leu Glu Ser Ser Gly Glu Leu Pro Ala Leu Phe
1665                1670                1675                1680
Arg Ala Leu Leu Arg Pro Ser Leu Arg Lys Ala Ser Ser Ala Thr Arg
            1685                1690                1695
Arg Asp Ala Ser Ala Leu Arg Glu Arg Leu Ser Ala Leu Pro Glu Ala
        1700                1705                1710
Glu Arg Leu Asn Ala Leu Val Glu Leu Val Arg Gly Glu Val Ala Ala
    1715                1720                1725
Val Ala Gly Leu Gln Arg Gly Glu Ala Val Ala Ala Asp Gln Val Leu
    1730                1735                1740
Lys Glu Leu Gly Leu Asp Ser Leu Met Ala Val Ala Leu Arg Asn Arg
1745                1750                1755                1760
Leu Thr Ser Arg Thr Glu Thr Ser Leu Pro Ala Thr Leu Val Phe Asp
            1765                1770                1775
Tyr Pro Thr Pro Arg Ala Ile Ala Glu Leu Leu Leu Lys Gln Ala Phe
        1780                1785                1790
Ser Gly Leu Gln Val Lys Glu Ala Arg Ala Arg Val Arg Arg Arg Ala
    1795                1800                1805
Gly Lys Asp Glu Pro Ile Ala Ile Val Ser Met Ala Cys Arg Leu Pro
    1810                1815                1820
Gly Gly Val Ala Thr Pro Asp Asp Tyr Trp Arg Leu Leu Ala Glu Gly
1825                1830                1835                1840
Lys Asp Ala Ile Glu Gly Leu Pro Ala Arg Trp Asp Gly Phe Glu Val
            1845                1850                1855
Tyr Asp Pro Asp Pro Glu Ala Ala Gly Lys Ser Tyr Ala Arg Glu Gly
        1860                1865                1870
Gly Phe Val Arg Asp Ile Asp Leu Phe Asp Ala Asn Phe Phe Gly Ile
    1875                1880                1885
Ser Pro Arg Glu Ala Gln Ser Met Asp Pro Gln His Arg Leu Val Leu
    1890                1895                1900
Glu Thr Ala Trp Glu Ala Leu Gly Arg Ala Gly Val Arg Pro Ser Ala
1905                1910                1915                1920
Leu Ser Gly Ser Ala Thr Gly Val Tyr Leu Gly Ser Met Gly Ser Asp
            1925                1930                1935
Tyr Gly Ala Leu His Thr Val Asp Leu Lys Glu Leu Asp Gly Tyr Arg
        1940                1945                1950
Gly Ile Gly Ser Ala Ala Ser Ile Leu Ser Gly Arg Val Ala Tyr Ala
    1955                1960                1965
```

-continued

```
Leu Gly Leu Gln Gly Pro Ala Met Thr Val Asp Thr Ala Cys Ser Ser
    1970                1975                1980

Ser Leu Val Ser Leu His Leu Ala Cys Thr Ala Leu Arg Gln Gly Glu
1985                1990                1995                2000

Cys Asp Leu Ala Leu Ala Gly Gly Val Thr Val Met Ser Thr Pro Ala
                2005                2010                2015

Leu Phe Val Glu Phe Ser Arg Leu Lys Gly Met Ser Arg Asp Gly Arg
            2020                2025                2030

Cys Lys Ser Phe Ser Val Gln Ala Asp Gly Ala Gly Trp Ala Glu Gly
        2035                2040                2045

Cys Gly Met Leu Leu Leu Lys Arg Leu Ser Asp Ala Gln Arg Asp Gly
    2050                2055                2060

Asp Arg Val Leu Gly Val Ile Arg Gly Ser Ala Val Asn Gln Asp Gly
2065                2070                2075                2080

Arg Ser Gln Gly Leu Thr Ala Pro Asn Gly Pro Ala Gln Gln Arg Val
                2085                2090                2095

Ile Arg Gln Ala Leu Ser Ser Cys Gly Leu Ser Pro Glu Asp Ile Asp
            2100                2105                2110

Ala Val Glu Ala His Gly Thr Gly Thr Ser Leu Gly Asp Pro Ile Glu
        2115                2120                2125

Ala Gly Ala Leu Ala Glu Val Phe Gly Pro Glu Arg Ser Pro Glu Arg
    2130                2135                2140

Pro Leu Tyr Leu Gly Ser Ser Lys Ser Asn Leu Gly His Ala Gln Ala
2145                2150                2155                2160

Ala Ala Gly Val Ala Gly Val Ile Lys Met Val Leu Ser Met Gln His
                2165                2170                2175

Glu Val Leu Pro Lys Thr Leu His Ala Glu Gln Pro Ser Pro His Ile
            2180                2185                2190

Gly Trp Glu Gly Ser Gly Leu Ser Leu Leu Gln Glu Ala Arg Pro Trp
        2195                2200                2205

Arg Arg Asn Gly Arg Val Arg Arg Ala Gly Val Ser Ser Phe Gly Ile
    2210                2215                2220

Ser Gly Thr Asn Ala His Ile Ile Leu Glu Glu Ala Pro Ala Glu Ala
2225                2230                2235                2240

Arg Arg Glu Pro Val Glu Ala Glu Ala Ala Pro Ala Leu Leu Pro Leu
                2245                2250                2255

Val Leu Ser Gly Arg Asp Glu Ala Ala Val Asn Ala Gln Ala Gly Arg
            2260                2265                2270

Trp Ala Lys Trp Leu Glu Glu His Gly Glu Val Gly Trp Ser Asp Val
        2275                2280                2285

Val Arg Thr Ala Ala Leu His Arg Thr His Phe Glu Ser Arg Ala Ser
    2290                2295                2300

Val Leu Ala Ala Ser Ala Ala Gly Ala Val Glu Gly Leu Arg Ala Leu
2305                2310                2315                2320

Ser Ser Gly Arg Pro Asp Ala Ala Val Val Ser Gly Thr Ala Lys Arg
                2325                2330                2335

Gly Gly Lys Leu Ala Val Leu Phe Thr Gly Gln Gly Ser Gln Arg Leu
            2340                2345                2350

Gly Met Gly Lys Arg Leu Tyr Glu Val Tyr Pro Val Phe Arg Ala Ala
        2355                2360                2365

Phe Asp Glu Val Cys Glu Ala Leu Asp Ala Tyr Leu Asp Arg Gly Leu
    2370                2375                2380

Arg Glu Val Val Phe Ala Ala Ala Gly Ser Glu Glu Gly Ala Leu Leu
```

```
                  2385                2390                2395                2400

Glu Arg Thr Glu Tyr Thr Gln Pro Gly Leu Phe Ala Leu Glu Val Ala
                   2405                2410                2415

Leu Tyr Arg Gln Trp Glu Ser Trp Gly Leu Lys Pro Ala Ala Leu Leu
                   2420                2425                2430

Gly His Ser Ile Gly Glu Leu Ser Ala Ala His Val Ala Gly Val Leu
                   2435                2440                2445

Ser Leu Ala Asp Ala Ala Lys Leu Val Cys Ala Arg Gly Arg Leu Met
       2450                2455                2460

Gln Gly Cys Glu Ala Gly Gly Ala Met Val Ser Val Glu Ala Ser Glu
   2465                2470                2475                2480

Pro Glu Val Gln Arg Ala Leu Ser Glu Val Gly Ala Gln Gly Arg Leu
                   2485                2490                2495

Ser Ile Ala Gly Leu Asn Ala Pro Met Gln Thr Val Leu Ser Gly Asp
                   2500                2505                2510

Glu Ala Ala Val Leu Ala Val Ala Arg Arg Leu Glu Ala Gln Gly Arg
                   2515                2520                2525

Arg Thr Arg Arg Leu Arg Val Ser His Ala Phe His Ser Ala His Met
       2530                2535                2540

Asp Gly Met Leu Glu Glu Phe Gly Lys Val Ala Arg Glu Cys Thr Tyr
   2545                2550                2555                2560

Ala Arg Pro Arg Leu Ala Val Val Ser Gly Val Thr Gly Glu Leu Gly
                   2565                2570                2575

Gly Glu Glu Ala Leu Met Ser Ala Glu Tyr Trp Val Arg Gln Val Arg
                   2580                2585                2590

Glu Ala Val Arg Phe Leu Asp Gly Met Arg Thr Leu Ala Ala Ala Gly
                   2595                2600                2605

Val Ser Thr Tyr Val Glu Cys Gly Pro Asp Gly Val Leu Cys Ala Leu
       2610                2615                2620

Gly Ala Gly Cys Leu Pro Glu Gly Ala Glu Ala Thr Phe Val Thr Ser
   2625                2630                2635                2640

Leu Arg Arg Glu Gln Glu Glu Glu Arg Ala Leu Ala Thr Ala Val Ala
                   2645                2650                2655

Thr Val His Val Gln Gly His Glu Val Asp Trp Ala Arg Val Leu Ser
                   2660                2665                2670

Gly Arg Gly Gly Arg Pro Val Glu Leu Pro Thr Tyr Ala Phe Gln Arg
       2675                2680                2685

Gln Arg Tyr Trp Leu Glu Ala Pro Lys Ser Ala Ala Thr Glu Val Asn
   2690                2695                2700

Val Ser Ser Ala Glu Gln Ala Leu Trp Asn Ala Ala Leu Glu Gly Glu
   2705                2710                2715                2720

Gly Asp Gly Val Ala Glu Leu Leu Glu Leu Pro Asp Asp Val Arg Ala
                   2725                2730                2735

Ser Val Gly Pro Leu Leu Pro Tyr Leu Ala Ala Trp Arg Gln Arg Lys
                   2740                2745                2750

Gln Ala Glu Ala Ala Ala Ala Ser Trp Leu Tyr Glu Glu Ala Trp Gln
                   2755                2760                2765

Asn Arg Pro Arg Arg Val Thr Gly Ser Pro Asp Val Arg Gly Thr Trp
       2770                2775                2780

Leu Val Val Ser Pro Pro Leu Ala Gly Glu Leu Ala Glu Val Val Arg
   2785                2790                2795                2800

Gly Ala Leu Gly Ala Ala Gly Ala Glu Val Ile Val His Ile Ala Ala
                   2805                2810                2815
```

-continued

```
Val Glu Arg Ala Gln Leu Ala Ala Trp Leu Arg Glu Gln Ala Arg Leu
        2820                2825                2830
Arg Lys Glu Glu Gly Glu Leu Arg Gly Val Ile Ala Leu Thr Ala Ser
    2835                2840                2845
Gly Glu Glu Gly Ala Leu Glu Gln Gly Gln Ala Pro Arg Ser Leu Tyr
2850                2855                2860
Gln Thr Leu Ala Val Val Gln Ala Leu Gly Asp Ala Gly Ile Gly Ala
2865                2870                2875                2880
Arg Leu Trp Leu Leu Thr Gln Gly Ala Val Ser Thr Glu Pro Ser Glu
        2885                2890                2895
Ala Val Val His Pro Leu Gln Ala Leu Thr Trp Gly Leu Gly Arg Ala
        2900                2905                2910
Leu Gly Leu Glu His Pro Glu Arg Trp Gly Gly Leu Leu Asp Val Pro
        2915                2920                2925
Ala Glu Leu Asp Ala Gly Val Met Gln His Val Leu Thr Thr Leu Val
        2930                2935                2940
Ser Asp Asp Asn Glu Asp Gln Val Ala Val Arg Arg Gly Gly Arg Leu
2945                2950                2955                2960
Val Arg Arg Ile Val Arg Val Arg Gly Glu Gly Asp Gly Glu Gly Trp
        2965                2970                2975
Lys Pro Arg Gly Thr Val Leu Ile Thr Gly Gly Val Gly Gly Leu Gly
        2980                2985                2990
Gly His Leu Ala Arg Trp Leu Ala Gly Arg Gly Ala Glu His Leu Val
        2995                3000                3005
Leu Ala Ser Arg Arg Gly Ala Ser Ala Pro Gly Ala Ser Glu Leu Arg
        3010                3015                3020
Asp Glu Leu Val Ala Arg Gly Ile Arg Val Thr Leu Ala Ala Cys Asp
3025                3030                3035                3040
Val Ser Glu Arg Ala Gln Leu Ala Ala Leu Leu Ala Glu Leu Glu Gln
        3045                3050                3055
Asp Glu Ala Pro Leu Arg Ala Val Ala His Leu Ala Gly Ile Gly Arg
        3060                3065                3070
Arg Val Pro Leu Arg Glu Leu Glu Pro Glu Gln Leu Glu Gln Glu Leu
        3075                3080                3085
Ala Ala Lys Val Lys Gly Ala Trp His Leu His Gln Leu Leu Gly Lys
        3090                3095                3100
Arg Glu Leu Asp Ala Phe Val Leu Tyr Gly Ser Ile Ala Gly Leu Trp
3105                3110                3115                3120
Gly Ser Gly Ala Gln Ala Gly Tyr Gly Ala Ala Asn Ala Gly Leu Asp
        3125                3130                3135
Ala Leu Ala Arg Tyr Arg Arg Ala Arg Gly Gln Ala Ala Thr Val Leu
        3140                3145                3150
His Trp Gly Pro Trp Ala Gly Glu Gly Met Val Thr Ser Glu Leu Glu
        3155                3160                3165
Ser Gln Leu Arg Ile Arg Gly Val Ala Val Met Ser Pro Asp Lys Ala
        3170                3175                3180
Leu Ala Gly Leu Glu Met Ala Leu Arg Leu Gly Arg Thr Ser Val Ala
3185                3190                3195                3200
Ile Ala Asp Val Asp Trp Ser Arg Phe Ala Pro Ser Phe Ser Ala Ala
        3205                3210                3215
Arg Pro Arg Pro Leu Leu Asp Gly Ile Glu Glu Ala Arg Arg Ala Gln
        3220                3225                3230
```

-continued

Glu Ser Arg Gly Pro Gln Pro Ala Ala Gly Gly Thr Ala Leu Arg Asp
    3235                3240                3245

Thr Leu Leu Gly Leu Ser Glu Ala Glu Arg Glu Arg Val Arg Gln
    3250                3255                3260

Leu Val Ala Ser Glu Thr Ala Ala Val Leu Gly Met Thr Asp Pro Ser
3265                3270                3275                3280

Arg Leu Asp Pro Asp Arg Gly Phe Leu Asp Leu Gly Leu Asp Ser Leu
        3285                3290                3295

Met Ala Val Glu Leu Ser Lys Arg Leu Gln Lys Arg Thr Gly Met Thr
        3300                3305                3310

Val Pro Ser Thr Leu Ser Phe Asp His Pro Thr Gln Ser Asp Val Ala
        3315                3320                3325

Arg Trp Leu Leu Glu Gln Leu Thr Pro Gln Pro Arg Pro Glu Pro Ala
    3330                3335                3340

Val Arg Glu Val Ser Arg Glu Glu Gly Trp Ser Thr Pro Ile Ala Ile
3345                3350                3355                3360

Val Gly Val Gly Leu Arg Met Pro Gly Gly Ala Ser Asp Leu Glu Ser
            3365                3370                3375

Phe Trp Gln Val Leu Val Glu Glu Arg Asp Thr Leu Arg Pro Ile Pro
        3380                3385                3390

Ala Gln Arg Phe Asp Val Glu Ala Leu Tyr Asp Pro Asp Pro Asp Ala
    3395                3400                3405

Lys Gly Lys Thr Tyr Val Arg Asn Ala Ser Leu Leu Asp Asp Val Ala
    3410                3415                3420

Ser Phe Asp Pro Gly Phe Phe Gly Ile Ser Pro Arg Glu Ala Glu Pro
3425                3430                3435                3440

Met Asp Pro Gln His Arg Leu Leu Leu Glu Thr Ala Trp Ser Ala Leu
            3445                3450                3455

Glu Asp Ala Gly Val Arg Pro Glu His Leu Lys Gly Ser Asp Thr Gly
        3460                3465                3470

Val Phe Val Gly Val Ala Pro Ser Glu Tyr Ala Ser Tyr Arg Gly Lys
        3475                3480                3485

Ser Ala Asn Glu Asp Ala Tyr Ala Leu Thr Gly Thr Ala Leu Ser Phe
    3490                3495                3500

Ala Ala Gly Arg Val Ala Tyr His Leu Gly Leu Gln Gly Pro Ala Val
3505                3510                3515                3520

Ser Thr Asp Thr Ala Cys Ser Ser Ser Leu Val Ala Val His Leu Ala
        3525                3530                3535

Cys Asp Ala Leu Arg Arg Gly Asp Cys Glu Val Ala Leu Ala Ala Gly
            3540                3545                3550

Val Gln Val Leu Ala Asn Pro Ala Gly Phe Val Leu Leu Ser Arg Thr
    3555                3560                3565

Arg Ala Leu Ser Pro Asp Gly Arg Cys Lys Ala Phe Ser Gln Ala Ala
    3570                3575                3580

Asp Gly Tyr Gly Arg Gly Glu Gly Val Gly Val Leu Val Leu Met Arg
3585                3590                3595                3600

Leu Ser Glu Ala Gln Gln Gln Gly Lys Arg Val Leu Gly Val Val Arg
            3605                3610                3615

Gly Thr Ala Val Asn Gln Asp Gly Ala Ser Ser Gly Ile Thr Ala Pro
            3620                3625                3630

Asn Gly Thr Ala Gln Gln Lys Val Val Arg Ala Ala Leu Arg Asn Ala
        3635                3640                3645

Gly Leu Glu Pro Ala Ser Ile Asp Val Val Glu Cys His Gly Thr Gly

-continued

```
              3650              3655              3660
Thr Ser Leu Gly Asp Pro Ile Glu Val Gln Ala Leu Gly Ala Val Tyr
3665              3670              3675              3680
Gly Gln Gly Arg Asp Met Ala Arg Pro Leu Gln Leu Gly Ala Val Lys
              3685              3690              3695
Ser Asn Ile Gly His Leu Glu Ser Ala Ala Gly Ile Ala Gly Val Cys
              3700              3705              3710
Lys Ile Leu Ala Ala Phe Arg Tyr Glu Ser Leu Pro Ala Thr Leu His
              3715              3720              3725
Ser Ser Pro Arg Asn Pro Arg Ile Pro Trp Glu Asn Leu Pro Val Gln
              3730              3735              3740
Val Val Asp Arg Leu Thr Pro Trp Pro Arg Arg Ala Glu Gly Pro Pro
3745              3750              3755              3760
Arg Arg Ala Gly Val Ser Ser Phe Gly Ile Ser Gly Thr Asn Ala His
              3765              3770              3775
Val Ile Leu Glu Glu Ala Pro Ala Glu Ala Arg Arg Glu Pro Val Glu
              3780              3785              3790
Ala Glu Ala Ala Pro Ala Leu Leu Pro Leu Val Leu Ser Gly Arg Asp
              3795              3800              3805
Glu Ala Ala Val Asn Ala Gln Ala Gly Arg Trp Ala Lys Trp Leu Glu
              3810              3815              3820
Glu His Gly Glu Val Gly Trp Ser Asp Val Val Arg Thr Ala Ala Leu
3825              3830              3835              3840
His Arg Thr His Phe Glu Ser Arg Ala Ser Val Leu Ala Ala Ser Ala
              3845              3850              3855
Ala Gly Ala Val Glu Gly Leu Arg Ala Leu Ser Ser Gly Arg Pro Asp
              3860              3865              3870
Ala Ala Val Val Ser Gly Thr Ala Lys Arg Gly Gly Lys Leu Ala Val
              3875              3880              3885
Leu Phe Thr Gly Gln Gly Ser Gln Arg Leu Gly Met Gly Lys Arg Leu
              3890              3895              3900
Tyr Glu Val Tyr Pro Val Phe Arg Ala Ala Phe Asp Glu Val Cys Glu
3905              3910              3915              3920
Ala Leu Asp Ala His Leu Asp Arg Gly Leu Arg Glu Val Val Phe Ala
              3925              3930              3935
Ala Ala Gly Ser Glu Glu Gly Ala Gln Leu Glu Arg Thr Glu Tyr Thr
              3940              3945              3950
Gln Pro Gly Leu Phe Ala Leu Glu Val Ala Leu Tyr Arg Gln Trp Glu
              3955              3960              3965
Ser Trp Gly Leu Lys Pro Ala Ala Leu Leu Gly His Ser Ile Gly Glu
              3970              3975              3980
Leu Ser Ala Ala His Val Ala Gly Val Leu Ser Leu Ala Asp Ala Ala
3985              3990              3995              4000
Lys Leu Val Cys Ala Arg Gly Arg Leu Met Gln Gly Cys Glu Ala Gly
              4005              4010              4015
Gly Ala Met Val Ser Val Glu Ala Ser Glu Pro Glu Val Gln Arg Ala
              4020              4025              4030
Leu Ser Glu Val Gly Ala Gln Gly Arg Leu Ser Ile Ala Gly Leu Asn
              4035              4040              4045
Ala Pro Met Gln Thr Val Leu Ser Gly Asp Glu Ala Ala Val Leu Ala
              4050              4055              4060
Val Ala Arg Arg Leu Glu Ala Gln Gly Arg Arg Thr Arg Arg Leu Arg
4065              4070              4075              4080
```

-continued

Val Ser His Ala Phe His Ser Ala His Met Asp Gly Met Leu Glu Glu
                4085                4090                4095

Phe Gly Lys Val Ala Arg Glu Cys Thr Tyr Ala Arg Pro Gln Leu Ala
                4100                4105                4110

Val Val Ser Gly Val Thr Gly Glu Leu Gly Gly Glu Glu Ala Leu Met
            4115                4120                4125

Ser Ala Glu Tyr Trp Val Arg Gln Val Arg Glu Ala Val Arg Phe Leu
            4130                4135                4140

Asp Gly Met Arg Thr Leu Ala Ala Ala Gly Val Ser Thr Tyr Val Glu
4145                4150                4155                4160

Cys Gly Pro Asp Gly Val Leu Cys Ala Leu Gly Ala Gly Cys Leu Pro
                4165                4170                4175

Glu Gly Ala Glu Ala Thr Phe Val Ala Ser Leu Arg Arg Glu Gln Glu
                4180                4185                4190

Glu Glu Arg Ala Leu Ala Thr Ala Val Ala Thr Val His Val Gln Gly
                4195                4200                4205

His Glu Val Asp Trp Ala Gln Val Leu Ser Gly Arg Gly Gly Arg Pro
            4210                4215                4220

Val Glu Leu Pro Thr Tyr Ala Phe Gln Arg Gln Arg Tyr Trp Leu Glu
4225                4230                4235                4240

Ala Pro Lys Ala Arg Thr Asp Val Gly Ser Ala Gly Leu Arg Glu Ser
                4245                4250                4255

Gly His Pro Leu Leu Gly Ala Ala Thr Lys Leu Ala Asp Gly Asp Gly
                4260                4265                4270

His Leu Phe Thr Gly Arg Leu Ser Leu Gly Glu Gln Pro Trp Leu Arg
            4275                4280                4285

Asp His Ala Val Phe Gly Glu Val Val Phe Pro Gly Thr Gly Met Leu
            4290                4295                4300

Asp Leu Ala Leu Ala Ala Gly Arg Thr Val Gly Ser Gly Ala Leu Ser
4305                4310                4315                4320

Glu Leu Thr Ile Ser Glu Pro Leu Met Leu Ala Glu Asp Val Ala Val
                4325                4330                4335

Arg Leu Gln Leu Ser Val Gly Ala Pro Asp Ala Ala Gly Arg Arg Ala
                4340                4345                4350

Phe Gly Leu Tyr Ser Gln Pro Glu Gln Gly Pro Gly Asp Ala Pro Trp
            4355                4360                4365

Val Gln His Ala Thr Gly Val Leu Thr Asp Glu Thr Leu Ala Thr Ser
            4370                4375                4380

Gly Glu Leu Asp Glu Leu Thr Thr Trp Pro Val Pro Gly Ala Glu Ala
4385                4390                4395                4400

Val Asp Leu Ser Gly Phe Tyr Glu Arg Leu His Glu Arg Gly Leu Arg
                4405                4410                4415

Tyr Gly Pro Ala Phe Gln Gly Leu Val Glu Leu Ser Arg Arg Asp Ala
                4420                4425                4430

Thr Phe Phe Gly Arg Val Val Leu Pro Lys Asp Ala Thr Asp Ser Ala
            4435                4440                4445

Glu Asp Tyr Gly Val His Pro Ala Leu Met Asp Ala Ala Leu His Thr
            4450                4455                4460

Met Val Ala Ala Phe Ala Glu Val Ser Ala Pro Asp Asp Val Leu Leu
4465                4470                4475                4480

Pro Phe Ser Trp Ser Asp Val Ala Leu His Ala Thr Gly Ala Ser Glu
                4485                4490                4495

-continued

```
Leu Arg Val Arg Leu Glu Leu Ala Gly Gly Arg Asp Ser Ala Gln Ala
        4500                4505                4510
Ala Ala Ser Leu Arg Val Thr Asp Ala Ala Gly Gln Pro Val Val Ser
        4515                4520                4525
Val Gly Ala Leu His Leu Arg Arg Ala Thr Ala Glu Gln Leu Arg Ala
        4530                4535                4540
Ala Thr His Ala Glu Ala Gln His Leu Tyr Arg Val Asp Phe Gln Leu
4545                4550                4555                4560
Val Ser Leu Val Glu Ala Gly Ser Lys Val Asp Ser Leu Val Val Leu
        4565                4570                4575
Arg Ala Pro Glu Gly Arg Gly Arg Leu Gly Glu Ala Leu Gly Val Glu
        4580                4585                4590
Ala Ile Ala Gly Leu Asp Ala Leu Leu Ala Arg Ile Glu Gln Gly Thr
        4595                4600                4605
Arg Leu Pro Glu Arg Val Leu Val Asp Met Thr Ala Gly Ser Ser Gln
        4610                4615                4620
Arg Ser Asp Met Val Ile Ser Ser His Glu Ala Thr Gly Gln Ala Leu
4625                4630                4635                4640
Ser Leu Leu Gln Ala Trp Leu Ser Glu Pro Arg Leu Glu Gly Val Glu
        4645                4650                4655
Leu Val Trp Val Thr Arg Asp Ala Val Ser Ala Ala Pro Gly Asp Gly
        4660                4665                4670
Val Gln Asp Leu Ala His Ala Pro Leu Trp Gly Leu Val Arg Thr Ala
        4675                4680                4685
Arg Ser Glu His Pro Glu Arg Arg Leu Arg Leu Ile Asp Val Gly Thr
        4690                4695                4700
Glu Pro Leu Asp Gly Gly Leu Leu Ala Arg Ala Leu Ala Thr Ala Thr
4705                4710                4715                4720
Glu Pro Glu Leu Ala Leu Arg Gly Gly Ala Ala Met Ala Ala Arg Leu
        4725                4730                4735
Val Arg Val Pro Ala Ala Ala Glu Gly Leu Thr Pro Ala Arg Gly Leu
        4740                4745                4750
Asp Pro Thr Gly Thr Val Leu Val Thr Gly Gly Thr Gly Glu Leu Gly
        4755                4760                4765
Gln Ala Val Ala Glu His Leu Val Arg Ala His Gly Val Arg His Leu
        4770                4775                4780
Val Leu Thr Ser Arg Arg Gly Leu Glu Ala Pro Gly Ala Pro Gly Phe
4785                4790                4795                4800
Val Gln Ala Leu Glu Lys Leu Gly Ala Glu Thr Val Thr Val Ala Ala
        4805                4810                4815
Cys Asp Val Ser Lys Arg Glu Glu Val Ala Arg Val Leu Ala Gly Ile
        4820                4825                4830
Glu Ala Ala His Pro Leu Thr Ala Val Leu His Leu Ala Gly Val Leu
        4835                4840                4845
Asp Asp Gly Val Ile Thr Ala Gln Thr Pro Glu Arg Leu Ser Arg Val
        4850                4855                4860
Leu Ala Pro Lys Val Asn Gly Ala Leu His Leu His Glu Leu Thr Glu
4865                4870                4875                4880
Asp Leu Asp Leu Ser Ala Phe Val Leu Phe Ser Ser Met Ser Gly Thr
        4885                4890                4895
Leu Gly Thr Ala Gly Gln Ser Asn Tyr Ala Ala Ala Asn Ser Phe Leu
        4900                4905                4910
Asp Ala Phe Ala Ala His Arg Arg Ser Arg Gly Leu Ala Ala Thr Ser
```

```
            4915                4920                4925
Leu Ala Trp Gly Phe Trp Ala Gln Thr Gly Val Gly Met Thr Ala His
    4930                4935                4940

Leu Gly Glu Ala Glu Leu Ser Arg Ile Gln Arg Ala Gly Leu Val Pro
4945                4950                4955                4960

Ile Arg Val Glu Glu Gly Leu Ser Leu Leu Asp Ala Ala Leu Leu Arg
            4965                4970                4975

Pro Glu Ala Ser Leu Val Pro Ala His Leu Asp Leu Ala Gln Met Gln
        4980                4985                4990

Arg Gly Leu Glu Ala Ser Gly Glu Leu Pro Ala Leu Leu Arg Ala Leu
    4995                5000                5005

Leu Arg Pro Gly Leu Arg Lys Ala Ser Ser Ala Thr Arg Lys Glu Ala
    5010                5015                5020

Ser Ala Leu Arg Glu Arg Leu Ser Glu Leu Pro Glu Ala Glu Arg Leu
5025                5030                5035                5040

Ser Ser Leu Val Glu Leu Val Arg Ala Glu Val Ala Ala Val Leu Gly
            5045                5050                5055

Leu Pro Arg Ser Glu Ala Val Ala Val Asp Gln Val Leu Lys Asp Leu
        5060                5065                5070

Gly Leu Asp Ser Leu Met Ala Val Glu Leu Arg Ser Arg Leu Ser Ala
    5075                5080                5085

Arg Ala Glu Ile Pro Leu Pro Ala Thr Leu Val Phe Asp Tyr Pro Thr
    5090                5095                5100

Pro Arg Ala Val Ala Glu Leu Leu Leu Arg Gln Ala Phe Ser Lys Gln
5105                5110                5115                5120

Gln Val Thr Ala Ala Arg Ala Arg Arg Thr Lys Glu Asp Glu Ala
            5125                5130                5135

Ile Ala Ile Val Ser Met Ala Cys Arg Leu Pro Gly Gly Val Ala Thr
        5140                5145                5150

Pro Glu Asp Tyr Trp Arg Leu Leu Ala Glu Gly Lys Asp Ala Ile Glu
    5155                5160                5165

Arg Phe Pro Ser Arg Tyr Asp Ala Phe Ser Val Tyr Asp Pro Asp Pro
    5170                5175                5180

Glu Ala Val Gly Lys Ser Tyr Val Arg Glu Gly Gly Phe Leu Arg Asp
5185                5190                5195                5200

Ile Asp Val Phe Asp Ala Gly Phe Phe Gly Ile Ser Pro Arg Glu Ala
            5205                5210                5215

Gln Ala Met Asp Pro Gln Gln Arg Leu Val Leu Glu Thr Ala Trp Glu
        5220                5225                5230

Ala Leu Glu Arg Ala Gly Val Arg Pro Ser Met Leu Ser Glu Ser Ala
    5235                5240                5245

Thr Gly Val Tyr Leu Gly Trp Met Gly Ser Asp Tyr Gly Ala Leu Leu
    5250                5255                5260

Gly Asn Asp Leu Ala Ala Leu Asp Gly Tyr Gln Gly Thr Gly Ser Ala
5265                5270                5275                5280

Ala Ser Val Leu Ser Gly Arg Val Ala Tyr Val Leu Gly Leu Gln Gly
            5285                5290                5295

Pro Ala Ile Thr Val Asp Thr Ala Cys Ser Ser Ser Leu Val Ser Leu
        5300                5305                5310

His Leu Ala Cys Thr Ala Leu Arg Gln Gly Glu Cys Asp Leu Ala Leu
    5315                5320                5325

Thr Gly Gly Val Met Val Met Thr Thr Pro Ala Gly Phe Val Glu Phe
    5330                5335                5340
```

```
Ser Arg Ala Arg Gly Leu Ala Arg Asp Gly Arg Cys Lys Ser Phe Ser
5345                5350                5355                5360

Ala Gln Ala Asp Gly Val Ile Trp Ser Glu Gly Cys Gly Met Leu Leu
            5365                5370                5375

Leu Lys Arg Leu Ser Asp Ala Arg Arg Asp Gly Asp Arg Val Leu Gly
        5380                5385                5390

Val Ile Arg Gly Ser Ala Val Asn Gln Asp Gly Arg Ser Gln Gly Leu
    5395                5400                5405

Thr Ala Pro Asn Gly Pro Ala Gln Gln Arg Val Ile Arg Gln Ala Leu
5410                5415                5420

Ser Ser Cys Gly Leu Ser Pro Glu Asp Ile Asp Ala Val Glu Ala His
5425                5430                5435                5440

Gly Thr Gly Thr Ser Leu Gly Asp Pro Ile Glu Ala Gly Ala Leu Ala
            5445                5450                5455

Glu Val Phe Gly Pro Glu Arg Ser Pro Glu Arg Pro Leu Tyr Leu Gly
        5460                5465                5470

Ser Ser Lys Ser Asn Leu Gly His Ala Gln Ala Ala Gly Val Ala
    5475                5480                5485

Gly Val Ile Lys Met Val Leu Ala Leu Gln His Glu Val Leu Pro Lys
    5490                5495                5500

Thr Leu His Ala Glu Gln Pro Ser Pro His Ile Ala Trp Glu Gly Ser
5505                5510                5515                5520

Gly Leu Ser Leu Leu Gln Glu Ala Arg Pro Trp Arg Arg Asn Gly Arg
            5525                5530                5535

Val Arg Arg Ala Gly Val Ser Ser Phe Gly Ile Ser Gly Thr Asn Ala
        5540                5545                5550

His Ile Ile Leu Glu Glu Ala Pro Ala Glu Ala Arg Arg Glu Pro Val
    5555                5560                5565

Glu Ala Glu Ala Ala Pro Ala Leu Leu Pro Leu Val Leu Ser Gly Arg
    5570                5575                5580

Asp Glu Ala Ser Val Ala Ala Gln Ala Gly Arg Trp Ala Lys Trp Leu
5585                5590                5595                5600

Glu Glu His Gly Glu Val Gly Trp Ser Asp Val Val Arg Thr Ala Ala
            5605                5610                5615

Leu His Arg Thr His Phe Glu Ser Arg Ala Ser Met Leu Ala Ala Ser
        5620                5625                5630

Val Ser Glu Val Val Glu Val Leu Arg Ala Leu Ser Glu Gly Arg Gly
    5635                5640                5645

His Arg Ala Val Ser Val Gly Thr Ala Arg Ala Arg Gly Lys Val Val
    5650                5655                5660

Phe Val Phe Pro Gly Gln Gly Ser Gln Trp Pro Gly Met Gly Arg Ala
5665                5670                5675                5680

Leu Leu Glu Gln Ser Ala Ala Phe Ala Glu Ala Val Gln Ala Cys Asp
            5685                5690                5695

Glu Ala Leu Arg Pro Trp Thr Gly Trp Ser Val Leu Ser Val Leu Arg
        5700                5705                5710

Gly Asp Gly Gly Glu Glu Gln Pro Ser Leu Glu Arg Val Asp Val Val
    5715                5720                5725

Gln Pro Ala Leu Phe Ala Met Cys Val Gly Leu Ala Ala Ala Trp Arg
    5730                5735                5740

Ser Leu Gly Leu Glu Pro Ala Ala Val Val Gly His Ser Gln Gly Glu
5745                5750                5755                5760
```

Val Ser Ala Ala Val Val Cys Gly Ala Leu Ser Leu Ala Glu Gly Ala
        5765                5770                5775

Arg Val Val Ala Leu Arg Ser Gln Ala Val Arg Gln Gln Ser Gly Met
        5780                5785                5790

Gly Ala Met Met Leu Val Glu Gln Pro Val Ser Glu Val Gln Glu Arg
        5795                5800                5805

Ile Ala Pro Tyr Gly Glu Ala Leu Ala Ile Ala Ala Val Asn Thr Ser
        5810                5815                5820

Asn Ser Thr Val Val Ser Gly Asp Val Glu Ala Val Asp Gly Leu Met
5825                5830                5835                5840

Val Glu Leu Thr Ala Glu Gly Val Phe Cys Arg Lys Val Asn Val Asp
        5845                5850                5855

Tyr Ala Ser His Ser Ala His Met Asp Ala Leu Leu Pro Glu Leu Gly
        5860                5865                5870

Ala Lys Leu Ser Ser Leu Arg Pro Lys Ala Thr Gln Leu Pro Phe Tyr
        5875                5880                5885

Ser Thr Val Thr Gly Glu Val Ser Arg Gly Glu Ala Leu Asp Gly Glu
        5890                5895                5900

Tyr Trp Cys Arg Asn Leu Arg Gln Thr Val Arg Leu Asp Arg Ala Leu
5905                5910                5915                5920

Ser Lys Leu Leu Glu Asp Gly His Gly Val Phe Val Glu Val Ser Ala
        5925                5930                5935

His Pro Val Leu Ala Met Pro Leu Thr Thr Ala Cys Gly Glu Ala Gln
        5940                5945                5950

Gly Val Val Val Gly Ser Leu Gln Arg Asp Glu Gly Gly Leu Ser Gln
        5955                5960                5965

Leu Tyr Arg Thr Leu Gly Gln Leu His Val Gln Gly His Glu Val Asp
5970                5975                5980

Trp Ala Arg Val Leu Ser Gly His Gly Gly Arg Ala Val Glu Leu Pro
5985                5990                5995                6000

Thr Tyr Ala Phe Gln Arg Gln Arg Tyr Trp Leu Asp Ile Ser Lys Ala
        6005                6010                6015

Arg Ser Asp Val Ser Ser Ala Gly Leu Lys Ala Ala Ala His Pro Leu
        6020                6025                6030

Leu Gly Ala Ala Thr Lys Leu Ala Glu Gly Asp Gly His Leu Phe Thr
        6035                6040                6045

Gly Arg Leu Ser Leu Gly Glu His Ala Trp Leu Arg Asp His Glu Val
        6050                6055                6060

Phe Gly Asn Leu Val Phe Pro Arg Ala Arg Gly Met Leu Glu Leu Ala
6065                6070                6075                6080

Leu Ala Ala Gly Pro His Gly Gly Gln Arg Gly Leu Phe Gly Lys
        6085                6090                6095

<210> SEQ ID NO 3
<211> LENGTH: 33529
<212> TYPE: DNA
<213> ORGANISM: Sorangium cellulosum

<400> SEQUENCE: 3
gatccccagc agcggctggt gctggagacg gcgtgggagg cattggagcg tgccggcgtg      60
cgcccgtcgg cgctgagcgg gagcgccacc ggagtgtatc tcgggtcgat gggctcggac     120
tacggtgctc ttcataccgg cgggctggaa gcgctggacg gtaccggggg caccggggagc     180 gcggcgagcg tgctctcagg ccgtgtggcc tacgtgctcg ggttgcaggg cccagcgatc     240

-continued

| | |
|---|---|
| acggtggaca cggcgtgctc gtcgtcgctg gtgtcgctgc acctcgcgtg cacggcgttg | 300 |
| cgtcagggtg aatgcgacct ggcgctggcc ggcggggtga cggtgatgag caccccgcg | 360 |
| ttgttcgtgg agttcagccg gctcaagggg atggcccgcg acggccgctg caagagcttc | 420 |
| tctgcgcgag ctgacggcgt cacctggtcc gagggtgcg ggatgctggt gctgaagcgg | 480 |
| ctgtcggacg cgcggcgcga cggtgaccgt gtgcttgcgg tggtccgcgg gtcagcggtg | 540 |
| aaccaggacg gtcgcagcca gggcctgacg cgccgaacg gtcccgcgca gcagcgggtg | 600 |
| gtccagcggg cgctctcgtc gtgcgggctg tcgcccgagg acatcgacgc ggtggaggcg | 660 |
| cacgggacag gcacgagcct cggagatccg atcgaggcgg gagcgctcgc ggaggtgttc | 720 |
| gggcctgggc gcaaggccga gcgaccgctg tacctgggct cgtcgaagtc caacctgggg | 780 |
| catacggggc ctgcggcggg tgtagtcggt gtgctcaaga tggtgctgtc gatgcagcac | 840 |
| gaggtgctgc cgcggacgct gcacgcggag cagccgagcc cgcacattgg gtgggagggg | 900 |
| agcgggctgt cgttgctgca agaggcgcgt ccgtggcggc gcaacggccg ggcgcggcgc | 960 |
| gcggcgtgt cgtcgttcgg gatcagcggg acgaacgcgc atgtcatcct cgaagaggcg | 1020 |
| ccggtggagg cggcgcgcga gccggtggag gcggtgcgcg agccgttggc gacggagggt | 1080 |
| gttgcgatgc cgctgttgct gtcggggcga gacgaggcct cggtggcggc gcaggcggag | 1140 |
| cgctgggcga agtggctgga agagcacgcg gaggtggggg ggtcggacgt ggtgaggaca | 1200 |
| gcggcgctgc accggacgca cttcgcctca cgcgcatcgg tgcttgcggc gagcgtgtcg | 1260 |
| gaggcggagg aggcgctgcg ggcgctgtcg cagggtcgcg gccaccgggc ggtgtcggcg | 1320 |
| ggcacgcgc gtgcgcgagg caaggtggtg ttcgtgttcc ccggccaagg gagccagtgg | 1380 |
| ccggggatgg gccgggcgct gctggagcag agcgcggcgt tcgcggaggc ggtgcaggcg | 1440 |
| tgcgatgagg cgctgcggcc gtggacgggc tggtctgtgc tgtcggtgct gcgcggcgag | 1500 |
| gcgggtgagg caggtgagga gcagccgtcg ctggagcggg tggacgtggt gcagcccgcg | 1560 |
| ctgttcgcga tgtgcgtggg tctggccgcg gcgtggaggt cgctggggct ggagcctgcg | 1620 |
| gcggtggtgg gccacagcca gggcgaggtg tcggcggcgg tggtgtgcgg ggcgctgtcg | 1680 |
| cttgcggagg gagcgcgggt agtggcgctg cgcagccagg cggtgcggca cggtcgggg | 1740 |
| atggggcga tgatgctggt cgagcggccg gtgtcggagg tgcaggagcg catcgcgccg | 1800 |
| tacggggagg cgcttgcgat agcggcggtg aacacgtcga gctcgacggt ggtgtcgggt | 1860 |
| gacgtggagg cggtggacgg gctgatgggg gagctgacgg cagaaggtgt gttctgccgg | 1920 |
| aaggtgaacg tcgactacgc gtcgcacagc gcgcacatgg atgcgctgct gcccgagcta | 1980 |
| ggagcgaagc tgtcgtcgct caggccgaag gcgacgcagc tgccgtttta ctcgacggtg | 2040 |
| gcaggagagt gtcgcgaggc gaggcgctgg acggcgagta ctggtgccgc aaccttcggc | 2100 |
| agacggtgcg cctggaccga gcgctgtcga agctgctgga ggacgggcac ggtgtgttcg | 2160 |
| tggaggtgag cgcgcacccg gtgctggcga tgccgctgac gacggcgtgc ggggaggcgc | 2220 |
| aggggtggt ggtggggagc ctgcagcgcg acgaaggtgg gttgtcgcag ctgtacagga | 2280 |
| cgctggggca gctgcacgtg caggcgcacg aggtggactg ggcacgggtg ctgccgggcc | 2340 |
| atggcggtcg tgccgtggag ctgccgacgt acgcattcca gcggcagcgc tactggctgg | 2400 |
| aggcgccgag ggcgcgcggt gacgtgagct cggcggggct gaaggcggcc gcccatccgc | 2460 |
| tgctcggcgc cgcgacgaag ctcgccgacg gcgaggggca cctgttcaca gggaggctgt | 2520 |
| cgctggcgga gcatgcgtgg cttcgggatc atggtgtgtt tggccaggtg gtgtttccgg | 2580 |
| gcacgggcat gctggaggtt gcgctggcgg ctgggcgcgc ggtgggcagc cggtcgctgt | 2640 |

```
cggagctcac gctcgccgag ccgctggtgc tggccgagga cggcgcggcg cggctgcagg    2700
tgatgatcgg agcgccagat gcggcgggcc ggcgcgaggt ggggctgtac agccagcctg    2760
agcatgcccc ggaggacgcg ccgtgggtgc agcacgcgac gggagtgttg acggacgagc    2820
tccccggcat ccctgacgag ctcgacgagc tgtcgatgtg gcctgtgccg ggcgcggagg    2880
aggtggacct gtccgggttt tacgagcggc tgcgtgagcg cgggctccac tacggtccga    2940
cgttccaggg cctcgtggag ctgtcgcgcc aaggcaccag gctttatggc cgggtggtgc    3000
tgccaggaac cgagaaggac agggcggagg cgtatggctt gcatcccgtc ctgatggatg    3060
cagcactgca ggtgcttggc gcagccggcg aggggcattg ggaggcggat gcgttgttta    3120
tgcccttctc ctgggcagac gccgcaacgc atgccacggg tccgagcgag cttcgggtgc    3180
gcgtggagct cgaagagaca gacggctcca cgcaggcaac ggcatctctg tgcgctgcag    3240
atgccgcagg ccagccggtg gcgagcgtcg gtgctttgcg tttgcgccgt gtgacggccg    3300
agcaattgag ggcggtcacc cgcaccgatg agcagcacct gtaccgggtg agcttccagc    3360
ccgtgagcct cgcgcaagcc ccctggaggc gggctcgct ggtggtcctc ggtgcagcgg    3420
agggacgagg gcagctggcc gacaccctgg gggcggaggc gattgccgat ctcgatgcat    3480
tgcgcgcttg gatcgagcgg ggcgcgccaa cgcctgtgcg ggtggtgatc gacacgaacg    3540
ctgccagctc accgcgctcg gacgtggcgg ggtcgtcgca cgaggcgacg aggcaggcgc    3600
tgtcgctgct gcaagcgtgg ttgtcggagc gcgggctcga cgctgtcgag ctggtgtggg    3660
tgacgcgggg cgcggtcagc gcagctccgg acgacgccgt cgaggacctg gcgcacgggc    3720
cgctgtgggg gcttattcgc acggcgcgca gcgagcaccc cgagcgccgg ctgcgcttga    3780
tcgatgtggg gaccgagccc gtggacgctg ggctgctggc gcgggcgctg gcgacggcgg    3840
cggagccgga gcttgcgctg cgcgggggcg cggtgctggc cgcgcggctg gtgcgcgtac    3900
aggcggcagc ggaagagctc acccgagccc gcgggctgga ccctgcgggc accgtgctgg    3960
tgaccggagc cgtgggcggt ctggggcagg cggtgacacg ccatctggtg cgcgcgcacg    4020
gggtgaggca ccttgtgctg acgtcgcgcc ggggctgga ggcgcccggg gcccgcgagc    4080
ttgtgcaatc gctcgagagc tcggcgccga ccgtgtcg atggtggcgt gcacgtgtc    4140 gaagcgggag gagatcgcgc gcgtgctggc cggcatcgac gcggcgcgcc cgctgagcgc    4200
ggtgctgcac ctggctggcg tggtccatga tggcgtgatt cagacgcaga cggccgagcg    4260
cctcgcgtgg gtgctggcgc cgaaggtgga cggggcgctg cacctgcacg agctgacgcg    4320
ggagctggat ctcgcggcgt tcgtgctgtt ctcgtcggcg gccggtacgt tgggcatggc    4380
gggccagggc aattacgcgg cggcgaatac gttcctcgac gcgttcgcgg cgcaccgccg    4440
cggccgcggg ctcgcggcga cgagcctcgc ctgggtgtc tggacaccgg ccggtggtgg    4500
catggcggca cagctggggg ccgcggagct ggcacggttc agtcgctacg gagtcgtgtc    4560
gatgtccgtg gaagaggggc tttcgctgct ggacgccgcg ctgtcacgcc ctgaagcgag    4620
cctggtccct atgcacctgg atctcgcgca gctgcagcgt gggctggagg ccaacggcga    4680
gctgccggcg ctgtttcgtg cgctgttgcg ccccagcttg cgcaaggcgt ccacggcgac    4740
gaggcgagac gcctcggcgc tgcgcgggcg cctctcggcg ctgccggagg cggagcggct    4800
gaatgcgctc atcgagctgg tgcggggcga ggtcgccgcg gtgctcgggc tccagcgcag    4860
cgaggccgtg ggggcggagc aggtgctgaa gggcctcggg ctcgactcgc tgatggcggt    4920
ggagctgcgc aaccgcctcg ccgcccggac ggagacgtcc ttgccggcga cgctggtctt    4980
```

-continued

```
cgactacccg acgccgcggg ccatcgcgga gttgctcctg aagctggcct tttcgggacc    5040
gcaggtgatg ggagcccgca gggggtgcg tcgtcatgcg gggaaagacg aggcggtggc    5100
gatcgtatcg atggcgtgcc ggctgccggg aggcgtcgag acgccggaag actactggcg    5160
tctcttggcc gagggaaag acgtgatcga gggcctccct gcgcgctggg agacgctttc    5220
ggtctacgac cccgacccgg aggcggtggg caagagctac gcgcgcgagg gtggattctt    5280
gcgggacatc gacctgttcg acgcggactt cttcgggata tcgccccgag aggcgcaggc    5340
gatggatccc cagcagcggc tggtgctgga cacggcatgg gaggcattgg agcgtgccgg    5400
cgtgcgcccg tcggcgctga gcgggagcgc caccggggtg tatctggggg ccgcgggttc    5460
ggactatggc gcttaccagg gtggcgggct ggagatgctg gacgggtacc ggggcatcgg    5520
gagcgcggcg agcgtgctct caggccgtgt ggcctacgtg ctcgggctgc atggcccagc    5580
gatgacggtg gacacggcgt gctcgtcgtc gctggtgtcg ctgcacctcg cgtgcacggc    5640
gttgcgtcag ggtgaatgcg acctggcgct ggccggcggg gtgacggtga tgagcacccc    5700
cgcgttgttc gtggagttca gccggctcaa ggggatggcc cgagacgcc gctgcaagag    5760 cttctctggg caggcggacg gcgcgggctg gtcgaggggg tgcgggatgc tggtgctgaa    5820
gcggctgtcg gacgcgcggc gcgacggtga ccgtgtgctt gcggtggtcc gtgggtcagc    5880
ggtgaaccag gacggtcgca gccaaggcct gacggcgccg aacggccccg cgcagcagcg    5940
ggtgatccag caggcgctgt cgtcgtgcgg gctgtcgccc gaggacatcg acgcggtgga    6000
ggcgcatggt acgggcacga gcctcggaga tccgatcgag gccggagcgc tcgcggaagt    6060
gttcgggcct gggcgcaagg ccgagcgacc gctgtacctt ggctcgtcga agtcgaacct    6120
tgggcacgcg caggctgcgg cggggtagcc ggtgtgctca agatggtgct gtcgatgcag    6180
cacgaggtgc tgccgaagac gctgcacgcg gagcagccga gcccgcacat gggtgggag    6240 gggagcgggc tgtcgttgct gcaagaggcg cgtccgtggc ggcgcaacgg ccgggcgcgg    6300
cgcgcgggcg tgtcgtcgtt cgggatcagc gggacgaacg cccatgtcat cctcgaagag    6360
gcgccggtgg aggcggctcg cgagccggtg gaggcggtgc gcgagccggt ggaggcggag    6420
ggtgttgcga taccgctgtt gctgtcgggg cgagacgagg cctcggtggc ggcgcaggcg    6480
gggcggtggg cgaagtggct ggaagagcac ggggaggtgg ggtggtcgga cgtggtgagg    6540
acggcggcgc tgcaccggac gcacttcgag tcgcgggcgt cggtgcttgc ggcgagcgct    6600
gcgggagctg tggagggtct tcgcgcgctg tcgtcgggc ggccggatgc ggcggtggtg    6660
agcgggacgg cgaagcgagg cgggaagctt gcggtgctgt tcacggggca gggcagccag    6720
cggctcggga tggggaagag gctttacgaa gtgtaccccg tgttccgtgc ggcgttcgac    6780
gaggtgtgcg aggcgctgga cgcgcatctc gaccgtgggt tgagagaggt ggtgttcgcg    6840
gccgcgggca gcgaggaagg agcgttgctg gagcggacgg agtacacgca gcccgggctg    6900
tttgcgctgg aagtggcgct gtaccgtcag tgggagtcgt kggggctgaa rcccgctgcg    6960
ctkctkgggc actcgatagg agagctgagc gctgcgcacg tggcgggtgt gctgagcctt    7020
gcggacgcag cgaagctagt gtgcgcccgc ggtcggctga tgcagggtg cgaggccggg    7080 ggagcgatgg tgtcggtgga ggcctcggag ccggatgtgc agcggcgct gtcggaggtc    7140 ggggcgcagg ggcgactgag catcgcgggg ctgaacgcgc cgatgcagac ggtgctgagc    7200
ggggacgaag cggcggtgct cgcggtggcg cgacggctgg aggcgcaggg ccggcgcacg    7260
cggcgtctgc gtgtgtcgca cgcgttccac agcgcgcaca tggacgggat gctggaggag    7320
ttcgggaagg tggcgcgggg gtgcacgtac gcgcggccac ggctggcggt ggtgagcggc    7380
```

```
gtgacgggcg agctcggtgg cgaagaagcg ctgatgtcgg ccgagtactg ggtgaggcag      7440
gtgcgcgagg cggtgcgctt cctggacggg atgcgcacgc ttgcggcggc ggggtgagc       7500 acatacgtcg agtgtgggcc ggatggcgtg ctgtgcgcgc tggggcggg gtgcctgccg       7560 gagggagccg aggcgacgtt tgtgacgagc ctgcggcgag agcaggagga agagcgcgcg      7620
cttgcgacgg cggtggcgac agtgcacgtg caggggcacg aggtggactg ggcccaggtg     7680
ctgtcgggcc gtggcggccg gcccgtggag ctgccgacgt acgcgttcca gcggcagcgc     7740
tactggctga aggcgcccaa gacgacggcg gcacaggcga atgtctcgtg gccggagcgt     7800
gcgttgtggg acgcggtgca gaaaggcgaa ggcgttgcgg atctgctgga gctgcctgac    7860
gacgtgcgcg agagcgtcgc gccgctgctg ccgtaccttg cggcgtggcg ccggagaagg     7920
gacgcagaag ccacggtgtc tggctggttg tacgaggagg cgtggcaaag ggaagccagc     7980
gctgccaggg caagccgga cgtgaggggc agatggctgc tggtgtcatc tccgcgtgcc      8040
ggagggctga ccgcggcggt gagtgatgcg ctcggagctg cgggtgcaga ggtgatcatc    8100
gagccggcga ccgaagagcg agcgcagctg gcggcgaggt tgagagggct ggagggcgag    8160
ctgcgtggcg tcgtggcgct gagcgcgcct gggagcaagg tgcgctggag aagggcgag     8220 ggcctcgcgc agtgtacgag gtgctggcgc tggcgcaggc gctcggtgac gctgggctcg    8280
atgcgcggct ctgggtgttg acgcaggag cggtgagcac ggaggcaagc gaagggtgt      8340 ccgaccctgc gcaggcgctg acgtgggggt tgggcgggt ggtggggctg gagcaccccg     8400
agcgctgggg tggactggta gacctgccgg cggaggtgga cgcggaagcg gtgcagcagg    8460
tgctgaggac gctcgttgcc gaggaccacg aggaccaggt ggcggtgcga cgcggtgggc    8520
gtcttgtgcg gcgcatcgtg cgggtgagtg gagaggacgg cggagcgggg tggaagccgc    8580
gtggcacggt gctcatcacg ggtggagtgg gagggctcgg gagccatctg gctcgctggt   8640
tggcggagcg gggagcagag cacctggtgc tggcgtcacg ccggggcgcc gcggcagcgg    8700
gcgcgcgcga gcttcgggag gagcttgagg ggcggggcgc gcgcgtgacg cttgcggcgt    8760
gcgatgtgtc ggagcgagcg caggtcgagg cgctggtgag ggagcttgag caggacgaag    8820
cgccgctgag cgcggtggcg catctggcgg ggatagtccg ccgcgtgccg gtgcgagagc    8880
tcgcgcccga gatgctggcg caggagctcg cggcgaaggt caacggagca tggcacctgc    8940
aggagctgct ggcagagcgc gagctggatg cgttcgtgct ttatggcagc atcgctgggc    9000
tgtggggctc tgggacgcag gccgggtacg gcgcggcgaa cgcagggctc gacgccctcg    9060
cgcgctaccg gcgtgcccga gggcagacgg cgacggtgct gcactgggc ccgtggtccg    9120 gaggcgggat ggtgagcgac gaggccgagc cgcagctccg gagccgcggg ctggtgccga    9180
tgtcgccgga caaggcgctt tgcgggctcg aggttgggct gcggcgcacg tcggtggcga    9240
tcgcggacgt ggactggtcg cgcttcgcgc cgctgttctg cgcggcgcgg ccgaggccgc    9300
tgctgtacgg gatcgagcaa gcgcgccatg cgctggaggg ccggacaccg cagcaggccg    9360
cgggcggagc gggggacaag gcgctgcggg agatgctgct cggcctgccg gctgtggagc    9420
ggagcgagcg gctgcgcgag ctcgtggcga gcgagacggc ggcggtgctg ggcgtgaagg    9480
atccgagcgg gctggacccg gagcgaggct ttctggacct cgggctggac tcgttgatgg    9540
cggtggagct gtcgaagcgg ctgcagcagc ggacgggggt gtcggtcaca aggacgttga    9600
tcttcgatta tccgacgcaa ggcgaggtaa cgcgctggct gctggagcag ctgatgccgc    9660
cggagcgacc ggcggcggac gagcacggcg tgagccgtgg accggagcgg agcgcgccga    9720
```

-continued

| | |
|---|---|
| tagcgatcgt gggcgtgggg ctgcgcatgc cgggcggagc gaacgatctg gagagcttct | 9780 |
| ggcaagtgct cgtggagggg cgggatacgc taaggccgat cccgaccgac cgtttcgacg | 9840 |
| tggaggcgat gtacgatcct aaccccgagg ccaagggcaa gacgtacgtg aagcatgcct | 9900 |
| cgctgctgga cgacgtggca tcgtttgacg cggggttctt cgggataagc ccgcgcgagg | 9960 |
| cggagccgat ggatccgcag caccggctgc tgctggagac tgcgtggagc gcgctggagg | 10020 |
| acgcgggagt gcgtccagac cagctgaagg gctcggacac gggtgtgttc gtgggcgtgg | 10080 |
| cgccgagcga gtatgcgagc tatcgcggca agagcgcgaa cgaagatgcg tatgcgctga | 10140 |
| cggggaccgc gctgagcttc gcagcgggcc gtgtggcata tcatctcggg ctgcaaggcc | 10200 |
| ctgcggtgtc ggtcgatacg gcgtgcagct cgtcgctggt gcgctgcacc tggcgtgcga | 10260 |
| cgcattgagg cgcggcgatt gcgaggtggc tctggcggcc ggcgtgcagg tgctcgcgaa | 10320 |
| cccggcgggg tttgtgctgc tgtcgcgcac gcgtgcggtc tcgcccgacg gacggtgcaa | 10380 |
| gacgttctcg caggcggccg acggctacgg ccgcggcgag ggcgtcgggg tggtggtgct | 10440 |
| gatgcgtctt tcggacgcac aggcgcaggg gatgcgggtg ctgggcgtgg tgcggggcac | 10500 |
| ggcggtcaat caggacggcg cgagcagcgg gatcacggcg ccgaacggca cggcccagca | 10560 |
| gaaggtggtg cgcgcggcgc tgcggaacgc ggggctggag gcgtcgagca tcgatgtggt | 10620 |
| cgagtgccac ggtacgggca cgtcgctggg cgatccgatc gaggtgcaag cgctcggcgc | 10680 |
| ggtgtacggg caaggcaggg aggcgactcg cccgctgcgg cttggagcgg tcaagagcaa | 10740 |
| catcggtcac ctggagtcgg ccgccggcat cgccggagtg tgcaagatcc tggcggcgtt | 10800 |
| tcggcatgag gccctgccgg cgacgttgca cagctcgccg cgcaaccccc agatctcctg | 10860 |
| ggagagtctg ccggtgcagg tggtcgaccg cctgaccggc tggcctcggc gcgccgacgg | 10920 |
| cctcccccgc tttgcgggcg tgtcgtcgtt tggcatcagc gggacgaacg cgcatgtcat | 10980 |
| cctcgaagag gcgccgcttg aggcggtgcg cgagccggcg gcggtgcgcg agccgttggc | 11040 |
| ggcggagggt gtcgcgatcc cgctgttgct gtcggggcga gacgaggcct cggtgggggc | 11100 |
| gcaggcggag cgctgggcga agtggctcgg agagcacgcg gaggtgcggt ggccggacgt | 11160 |
| ggtgagaacg gcggcgctgc accggacgca cttcgcctgg cgcgcatcgg tgcaggcggc | 11220 |
| gagcgtgtcg gaggcggtgg aggggctgag gcgctgtcg gagggtcgag ccgcggcagg | 11280 |
| tgtggtgcgc gggacgggag ggcgcggggg gaagcttgcg gtgctgttca cggggcaggg | 11340 |
| gagccagcgg ctcgggatgg ggaagagact ttacgaagtg tacccgtgt tccgtgcggc | 11400 |
| gttcgacgag gtgtgcgagg cgctggacgc gcatctcgac cgtgggttga gagaggtggt | 11460 |
| gttcgcggaa gcgggcagcg agcaggaggc gctgctggag cggacggagt acacgcagcc | 11520 |
| cgggttgttt gcgctggaag tggcgctgta ccggcagtgg gaggcgtggg gagtgaggcc | 11580 |
| cgcggcgctg ctggggcact cgataggaga gctgagcgct gcgcacgtgg cgggcgtgct | 11640 |
| gagccttgcg gacgcagcga agctagtgtg cgcccgcggt cggctgatgc agaggtgcca | 11700 |
| ggcgggcgga gcgatgatgt cggtggaagc gtcggagccg gaggtgcagg gggcgctgtc | 11760 |
| ggcgatgggg ctggagggcc ggcttgggat cgcgggcatc aacggtccga gccagacggt | 11820 |
| gctgagcggg gacgaagcgg cggtgctgga ggtgggcagg cggttcgagg cgcagggccg | 11880 |
| gcgcacgcgg cgtctgcgcg tgtcgcacgc attccacagc gcgcacatgg acgggatgct | 11940 |
| ggaagagtac gggagggtgg cgcgggagtg cgcgtatggg aggccgcagg tacccgtggt | 12000 |
| gagcggcgtg acggcgagc tcggtggcga agaatcgctg atgtcggccg agtactgggt | 12060 |
| gaggcaggtg cgcgaggcgg tgcgcttcct ggacgggatg cgcacgcttg cggcggcggg | 12120 |

-continued

```
ggtgagcaca tacgtcgagt gcggtccgga tggcgtgctg tgcgcgctgg gggcggggtg    12180
cctgccggag ggagccgagg cgacgtttgt ggcgagcctg cggcgagagc aggaggaaga    12240
gcgcgcgctt gtgacggcgg tggcgacggt gcacgtgcaa gggcacgagt ggactgggcc    12300
caggtgctgt cgggccatgg cggccggccc gtggagctgc cgacgtacgc gttccagcgg    12360
cagcgctact ggctggaggc gccgagggcg cgcggcgacg tgggctcggc ggggctgaag    12420
gcggccgccc atccgctgct cggcgccgcg acgaagctcg ccgacggcga ggggcacctg    12480
ttcacaggga ggctgtcgct ggcggagcat gcgtggcttc gggatcatca ggtgtttggc    12540
aaggtggtgt ttccgggcac ggggatgctg gagctggcgc tggcggcggg gcgcgcggtg    12600
ggcagccgga cgctgtcgga gctggttctg gccgagccgc tggtgctggc cgaggaggcc    12660
gcggcgcggc tgcagctgtc ggtcggagcg ccggacgcgg cgggccggcg cgaggtaggg    12720
ctgtacagcc agtccgagca ggcgccggag gacgcgccgt gggtgcagca cgccacgggc    12780
gtgttgacgg acgagatccc cggcgccccc ggcgagctcg acgagctgtc gacgtggcct    12840
gtgccgggcg cggaggaggt ggacctgtcc gggttttacg agcggctgcg tgagggcggg    12900
ctcgactacg gtccggtgtt ccagggcctc gtggagctct ggcgtcgagg cgcgaggctt    12960
tacgccgggt ggtgttgcc cgggagcgcg aggggcagcg ccgaggcgta tggggtgcat    13020
ccggcgctga tggacgccgc gctccacacg atggtcgcag ctttctctca gatgtcaggg    13080
ccagacggcg tgttgttgcc gttcgcctgg tcggacgtgg cgccgcacgc gacggggcg    13140 agcgagcttc ggatccgagt ggagatgcag gaacaaagcg cacagcagcc agcggcttcg    13200
ctgtacgtcg cagactgcac ggggcaggtc gtggcgagca tcggcgctct acgtctgcgc    13260
cgggcgacgg ccgagcagct gcggaccgcc gttcacgctg gtggccaaca tatgtatcag    13320
gtgagcttcc agcctgtgga cctcgcagca cctcccttgg tgacgggctc gctggtggtc    13380
atcggtgcac cgaagggagg agcgcggctg gccgaagccc tgggggcgga ggcgattgcc    13440
gatctcgatg cattggttgt gcgcctcgag catggcgcga gcgcgcctga gcgggtggtg    13500
gtcgacgtca ccgccgcgag cccgagcccg ttggacgtgc cggggtcgtc gcatgaggcg    13560
acgaggcagg cgctgtcgct gctgcaagcg tggctgtcgg agccgcggct cgaagcgacc    13620
gagctggtgt ggatcacgcg gggcgcggtg ggcgcggcgc cagacgacgc cgtcgaggac    13680
ctggcgcgcg cgccgctgtg ggggcttgtc cgccgcgcgc gaagcgagca ccccgaacgc    13740
gggctgcgct tgatggatgt ggggaccgag cccgtggacg ctgggctgct ggcgcgggcg    13800
ctggcgacgg cggcggagcc ggagcttgcg ctgcgcgggg gcgctgcgct ggccgcgcgc    13860
ctggtgcgcg cacaggcggt agcggaagag ctcacccgag cccgcgagct ggaccctgcg    13920
ggcacggtgc tggtgaccgg cgggacaggg gagctgggtc aggcggtcgc ggcgcacctg    13980
gtgcgcgcgc acggggtgcg gcaccttgtg ctgacgtcgc ggcgcgggct ggaggcgccc    14040
ggggcccgcg agcttgtgga atcgctcgcg gagctcggcg ccgagacggt gacggtggcc    14100
gcgtgcgacg tgtcgaagcg ggaggaggtc gcgcgtgtgc tggccggcat cgacgcggcg    14160
cgcccgctga gcgcggtgct gcacctggcc ggcgcgctcg acgacggcgt gctcgccggc    14220
cagacggccg agcgcctctc gcgggtgctg gcgccgaagg tggacgggc gctgcacctg    14280 cacgagctga cgcgggagct ggatctcgtg gcgttcgtgc tgttctcgtc ggtggcggta    14340
cgtttggcac ggcgggccag agcaactacg cggcggcgaa tacgttcctc gacgcgctcg    14400
cggcgcaccg gcgcggctgc gggctcgcgg cgacgagcct ggcgtggggg ttgtgggcgc    14460
```

```
aagcgggcgt ggggatgaca gcgcacctgg gcgaggccga actgtcgcgc atcaggcgcg   14520
cagggctcgt gccgatatcg gtcgacgagg gcctcgctct gctggacgcc gcgctctcac   14580
gctctgaagc gagcctggtc ccagtgcacc tggatctcgc gcagctgcag cgtgggctgg   14640
agtccagcgg cgagctgccg gcgctgcttc gcgcgctggt gcgcccgggg ctgcgcaagg   14700
cgtcctctgc cgcgaggaag gaggcgtcga cgctccgcga gcgcctctcg gcgctgccgg   14760
aggcggagcg cctgagctcg ctcatcgacc ttgtgcgggc cgaggtcgcc gcggtgctcg   14820
ggcttcagcg cggtgacgcg attcctacgg cccagccctt gagggagctc ggaatggatt   14880
cgctcatggc cgtcgaagtc cgcaatcggc tcgccttgct ggtcggaagc aacttgcctg   14940
ccactttgct tttcgaccat ccatctgcca cgcacatcgc gaagttcctc ctgtcaaagt   15000
tcggaaacgg tgagcgccgg aatctgctgc gtacagcgga ctccatgtcc gacgaggaaa   15060
ttcgcgcgtt catgctcagc ctctccgtca gtctcgtgcg tcgttcaggc ctcctcccca   15120
agctcttgga gctgcggggg ccgtccgaaa catccgtcga ggttccggtt cccatttccg   15180
atttcgaaga tctcgccgac gagcagctgg ccttgcaagc cttgcaaatg atttcgaact   15240
cagaggatct ccatgaatag cagcgccgcc tctcctacgc ttcgtgaggc gttgacccgt   15300
gcattgaaag agttgcagag gctgcaggcc agccactcgg atctccgttc agggcccatc   15360
gccatcgtat cgatggcgtg ccggctgccg gggggcgtcg ctacgccgga agactactgg   15420
cgtctcctgg aggaggggag agatgcgatc gaggccttcc ctgcgcgctg ggatgcacct   15480
tcgatttacg accccgatcc ggaggcgtg ggcaagacct acgtgcgcga gggtggattc   15540
ctgcgggaca tcgacctgtt cgatgcgggt ttcttcggga tatcgccccg agaggcgcag   15600
gcgatggatc cccagcagcg gctggtgctg agacgcgcg gggaggcact ggagcgggct   15660
ggcgtgcgcc cgtcggcgct gagcgagagc tccaccgggg tgtacctggg ctcgatgggc   15720
tcggactacg gtgctctta cggcagcgac ctggcggcgt tggacggcta ccggggcacc   15780
gggagcgcgg cgagcgtgct ctcaggccgt gtggcgtacg tgctcgggct gcagggccca   15840
gcgatcacgg tggacacggc gtgctcgtcg tcgctggtgt cgctgcacct ggcgtgcacg   15900
gccctgcgtc agggcgagtg cgatctggcc ttgaccggtg gggtgatggt gatgaccaca   15960
cccgcgggat tcgtggagtt cagccgcctc aaggcccttg cacgggacgg tcgttgcaag   16020
agcttctctg cgcgagctga cggcgtcatc tggtccgagg ggtgcgggat gctggtgctg   16080
aagcggctgt cggacgcgcg gcgcgacggt gaccgtgtgc tggcggtgat ccgtgggtca   16140
gcggtgaacc aggacggtcg cagccagggt ttgacggcgc gaacggccc tgcccagcag   16200 cgggtgatcc aacaggcgct ctcgtcgtgc cggctgtcgc ccgaggacat cgacgcggtg   16260
gaggcgcatg ggacgggcac gaacctgggc gacccgatcg aggccggagc gctcgtggag   16320
gtgttcgggc ctgggcgcaa ggccgagcgg ccgctgtacc ttggctcgtc gaagtcgaac   16380
ctggacacgc ggggcctgcg gcgggcgtcg ccggtgtgct caagatggtg ctgtcgatgc   16440
agcacgaggt gctgccgcgg acgctgcacg cggagcagcc gagcccgcac attgggtggg   16500
aggggagcgg gctgtcgttg ctgcaagagg cgcgtccgtg gcggcgcaac ggccgggcgc   16560
ggcgcgcggg cgtgtcgtcg ttcgggatca gcggacgaa cgcgcatgtc atcctcgaag   16620
aggcgccggt ggaggcggcg cgcgagccgg tgaggcaat gcgcgagccg ttggcgacgg   16680
aggtgtttgc gatgccgctg ttgctgtcgg ggcgagacga ggcctcggtg ggggcgcagg   16740
cggagcgctg ggcgaagtgg ctcggagagc acggggaggt gcagtggtcg gacgtggtga   16800
ggacagcggc gctgcaccgg acgcacttcg cctcacgcgc atcggtgctt gcggcgagcg   16860
```

-continued

```
tgtccgaggc ggaggaggcg ctgcgggcgc tgtcgcaggg tcgcggccac cgggcggtgt    16920
cggcgggtac ggcgcgtgcg cgaggcaagg tggtgttcgt gttccccggc caagggagcc    16980
agtggccggg gatgggccgg gcgctgctgg agcagagcgg ggcgttcgcg gaggcggtgc    17040
aggcgtgcga tgaggcgctg cggccgtgga cgggctggtc tgtgctgtcg gtgctgcgcg    17100
gagatggcgg ggaggagcag ccgtcgctgg agcggtgga cgtggtgcag cccgcgctgt    17160
tcgcgatgtg cgtgggtctg gccgcggcgt ggcggtcgct ggggctggag cctgcggcgg    17220
tggtgggcca cagccagggc gaggtgtcgg cggcggtggt gtgcggagcg ctgtcgcttg    17280
cggagggagc gcgggtagtg gcgctgcgca gccaggcggt gcggcagcgg tcggggatgg    17340
gggcgatgat gctggtcgag cggccggtgt cggaggtgca ggagcgcatc gcgccgtacg    17400
gggaggcgct tgcgatagcg gcggtgaaca cgtcgagctc gacggtggtg tcgggtgacg    17460
tggaggcggt ggacgggctg atggtggagc tgacggcaga aggtgtgttc tgccggaagg    17520
tgaacgtcga ctacgcgtcg cacagcgcgc acatggatgc gctgctgccc gagctaggag    17580
cgaagctgtc gtcgctcagg ccgaaggcga cgcagctgcc gttttactcg acggtgacag    17640
gagaggtgtc gcggggcgag gcgctggacg gcgagtactg gtgccgcaac cttcggcgga    17700
cggtgcgcct ggaccgagcg ctgtcgaagc tgctggagga cgggcacggt gtgttcgtgg    17760
aggtgagcgc gcacccggtg ctggcgatgc cgctgacgac ggcgtgcggg gaggcgcagg    17820
gggtggtggt ggggagcctg cagcgcgacg aaggtgggtt gtcgcagctg tacaggacgc    17880
tggggcagct gcacgtgcag gggcacgagg tggactggac acgggtgctg tcgggccacg    17940
gcggtcgtgt cgtggagctg ccgacgtacg cgtttcagcg gcagcgttac tggctggata    18000
tctcgaaggc gcgtagcgac gtgagctcgg cggggctcaa ggcagcagca caccgctgc    18060 tcggcgccgc gacgaggctc gccgacggcg agggcacct gttcacaggg cggctgtcgc    18120
tggcggagca tccgtggctt cgggatcatg aggtgtttgg ccaggtggtg cttccgggca    18180
cggggacgct ggagctggtg ctggcggcgg ggcgcgcgt gggcagccgg tcgctgtcgg    18240
agctcacgct ggccgagccg ctggtgctgg ccgagggcgc ggcgcggctg caggtgatga    18300
tcggagcgcc ggacgcggcg ggccggcgcg aggtggggct gtacagccag cctgagcagg    18360
ccccggagga cgcgccgtgg gtgcagcacg cgacgggagt gttgacggac gagcccccg    18420 gcatccctgt cggctcgacg agctgtcgac gtggcctgtg ccgggcgcgg aggaggtgga    18480
cctgtccggg ctttacgagc ggctgcgtga gcgcgggctc cactacggcc cggcgtttca    18540
agggctcgtg gagctgtcgc gccaaggcac aacctacttc ggtcgggtgg tgctgccggg    18600
gaccgagaag gacagggcgg aggcgtatgg cgtgcacccg gcgttgatgg acgccgcgct    18660
ccacacgatg gtcgcggcct ctccgagag cccaggggcg aacgaggtgc tcgtgccgtt    18720
tgcctggtcg gacgtggcgc tgcacgcgac ggggcgagc gagcttcggg tccgggtaga    18780
gctccaggac ggaggcgcac accaggacac cgcttcgctg caagtcgcag actccacggg    18840
gcaggccgtg gcgagcatcg gcgctctaca tctgcgccgg gcgacggccg agcagctgcg    18900
gaccgccgtt cacgctggtg gccaacatat gtatcaggtg agcttccagc ctgtggagct    18960
cgcggcagcc ccctggagg cgggctcgct ggtggtcgtc ggtgcagcgg agggacgagg    19020
caggctggcc gaagccctga gggcggaggc gattgccgat ctcgaagcat tggttgcgcg    19080
cctcgagcag ggcgcgagcg cgcctgcgcg ggtggcggtc gacacgacag ctttaggaca    19140
gagtcagtcg ggagtggcgt cgttgtccca cgaggcgacg aggcaggcgc tgtcgctgct    19200
```

```
gcaagcgtgg ctgtcggagc cgcggctcga cgctgtcgag ctggtgtggg tgacgcgggg   19260
cgcggtgggc gcggcgccgg acgacgccgt ccaggatctg gcgcgcgcgc cgctgtgggg   19320
gcttgttcgc gcggcgcgca gcgagcaccc cgagcgccgg ctgcgcttga tcgatgtggg   19380
gaccgagccc gtggacgctg ggctgctggc gcgggcgctg gcgacggcgg cggagccgga   19440
gcttgcgctg cgcggggggcg ctgcgctggc cgcgcgcctg gtgcgcgcgc aggcggcagc   19500
```

```
ggtacgggca cgagccttgg agacccgatc gaggccggag cgctggcgga ggtgtttgga    21660
ccggagcgta gccccgagcg tccgctgtac ctgggatcgt cgaagtcgaa cctcggacat    21720
gcgcaggcgg cggcgggcgt ggcgggcgtg atcaagatgg tgctgtcgat gcagcacgag    21780
gtgctgccga agacgctgca cgcggagcag ccgagcccgc acattgggtg ggaaggaagc    21840
gggctgtcgc tgctgcaaga ggcgcgtccg tggcggcgca acggccgggt ccgtcgtgcc    21900
ggcgtgtcgt cgttcgggat cagcgggacg aacgcgcata tcatcctcga agaagcgccg    21960
gccgaggcgc ggcgcgagcc tgtcgaggcc gaggcggcgc ctgcgctatt gccgctggtg    22020
ctgtcgggtc gagacgaggc cgcggtgaat gcgcaggcgg ggcggtgggc gaagtggctg    22080
gaagagcacg gggaggtggg gtggtcgacg tggtgcgca cggcggcgct gcaccggacg    22140
cacttcgagt cgcgggcgtc ggtgcttgcg gcgagcgctg cgggagctgt ggagggtctt    22200
cgcgcgctgt cgtcggggcg gccggatgcg gcggtggtga gcgggacggc gaagcgaggc    22260
gggaagcttg cggtgctgtt cacggggcag ggcagccagc ggctcgggat ggggaagagg    22320
ctttacgaag tgtaccccgt gttccgtgcg gcgttcgacg aggtgtgcga ggcgctggac    22380
gcgtatctcg accgtgggtt gagagaggtg gtgttcgcgg ccgcgggcag cgaggaagga    22440
gcgttgctgg agcggacgga gtacacgcag cccgggctgt ttgcgctgga agtggcgctg    22500
taccgtcagt gggagtcgtg ggggctgagc ccgctgcgct gctgggcac tcgataggag    22560
agctgagcgc tgcgcatgtg gcgggtgtgc tgagccttgc ggacgcagcg aagctagtgt    22620
gcgcccgagg tcggctgatg caagggtgcg aggccggggg agcgatggtg tcggtggagg    22680
cctcggagcc ggaggtgcag cgggcgctgt cggaggtcgg ggcgcagggg cgactgagca    22740
tcgccgggct gaacgcgccg atgcagacgg tgctgagcgg ggacgaagcg gcggtgctcg    22800
cggtggcgcg gcggctggag gcgcagggcc ggcgcacgcg gcgtctgcgt gtgtcgcacg    22860
cgttccacag cgcgcacatg gacgggatgc tggaggagtt cgggaaggtg gcgcgggagt    22920
gcacgtacgc gcgccacgg ctggcggtgg tgagcggcgt gacgggcgag ctcggtggcg    22980
aagaagcgct gatgtcggcc gagtactggg tgaggcaggt gcgcgaggcg gtgcgcttcc    23040
tggacgggat gcgcacgctt gcggcggcgg gggtgagcac atacgtcgag tgtgggccgg    23100
atggcgtgct gtgcgcgctg ggggcggggt gcctgccgga gggagccgag gcgacgtttg    23160
tgacgagcct gcggcgagag caggaggaag agcgcgcgct ggcgacggcg gtggcgacag    23220
tgcacgtgca ggggcacgag gtggactggg cccgggtgct gtcgggccgt ggcggccggc    23280
ccgtggagct gccgacgtac gcgttccagc ggcagcgcta ctggctggaa gcgccgaaga    23340
gcgcggcgac cgaggtgaat gtctccagcg cggagcaggc gctgtggaat gcggcgctgg    23400
agggcgaggg agatggcgtt gcggagctgc tggagctgcc tgacgacgtg cgcgccagcg    23460
tcgggccgct gctgccgtac ctcgcggcgt ggcgccagaa aaagcaggca gaagcggcgg    23520
cggcgagctg gctgtatgag gaagcgtggc aaaaccgtcc gaggcgtgtg acgggtagtc    23580
cggatgtaag gggcacctgg ctcgtggtgt cacctccgct tgccggagag cttgcggagg    23640
tggtgcgtgg tgcgctcggc gccgcggggg ccgaggtgat cgtgcacatc gcggccgtgg    23700
agcgagcgca gctcgcagcg tggctgagag agcaagcgcg cctgagaaag gaggagggcg    23760
agctgcgtgg cgtcatcgcg ctcacggcct caggcgagga aggcgcgctg gagcaagggc    23820
aggcgccccg cagcctgtac cagacgctgg cgtggtgca ggcgctcggc gacgccggaa    23880
tcggcgcgcg gctgtggttg ctcacgcagg gagcggtcag caccgagcca agcgaagcgg    23940
```

-continued

```
tggtgcaccc gttgcaggcg ctgacgtggg gactgggacg ggcgttgggg ctggagcacc    24000
ccgagcgctg gggcgggctg ctggacgtgc cggcggagct ggacgcgggc gtgatgcagc    24060
acgtcttgac cacgcttgtg tccgacgaca acgaagatca ggtggcggtg cggcgcggcg    24120
ggcgcctcgt gaggcgcatt gtgcgtgtgc gcggcgaggg cgacggcgag ggctggaagc    24180
cgcgcggcac ggtgctcatc acgggcggcg tgggcgggct cggaggtcat cttgcccgct    24240
ggctggccgg gcgtggcgca gagcaccttg tgctggcgtc gcgccgcggc gcgtcggcgc    24300
ccggggcgag cgagctgcgg gacgagcttg tggcgcgggg cattcgggtg acgctggcgg    24360
cgtgtgacgt gtcggagcgc gcgcagctcg cggcgctgct cgcggagctg gagcaggatg    24420
aagcgccgct gagggcggtg gcgcacctcg cgggcatagg ccgccgtgtt ccgctgcgag    24480
agctcgagcc tgagcagctc gagcaggagc tcgcggcgaa ggtgaagggg gcgtggcacc    24540
tgcatcagct gctggggaag cgggagctgg atgcgtcgtg ctctatggca gcatcgccgg    24600
gctgtggggc tccggggcgc aggctgggta cggcgcagcc aacgcagggc tggacgcgct    24660
cgcgcggtac cggcgcgcgc gagggcaggc tgcgacggtg ttgcactggg gcccctgggc    24720
gggagaaggg atggtgacca gcgagctcga gtcgcagctg cggatccgcg gggtcgcggt    24780
gatgtcgccc gacaaggcgc tcgccgggct ggagatggcg ctgcggctgg ggcgcacgtc    24840
ggtggcgatc gccgacgtgg actggtcgcg cttcgcgccg tcgttcagcg cggcgaggcc    24900
gaggccgctc ctggacggga tcgaggaggc ccgcggggcg caggagagcc gcggcccgca    24960
gccggccgca ggcgggaccg cgctgagaga caccttgctg ggcctgagcg aggccgagcg    25020
gcgcgagcgg gtacgtcagc tggtggcgag cgagacggcc gcggtactgg gcatgacgga    25080
cccgagccgg cttgacccgg accgtggctt tctggacctc gggctggatt cgctgatggc    25140
ggtggagctg tcgaagcggc tgcagaagcg cacgggcatg acggtaccga gcacgctgag    25200
cttcgatcac ccgacgcaga gcgacgtggc gcgctggctg ctggagcagc tcacacctca    25260
gccgcgaccg gagccggcgg tgcgcgaggt gagccgggaa gaggggtgga gcacgccgat    25320
agcgatcgtg ggcgtggggc tgcgcatgcc tggcggagcg agcgacctgg agagcttctg    25380
gcaggtgctg gtcgaagagc gggatacgct gcggccgatc ccggcccaac gattcgacgt    25440
cgaggcgctg tacgatcctg acccgacgc gaagggcaag acgtacgtgc ggaacgcgtc    25500
gctgctcgac gacgtggcgt cgttcgaccc tgggttcttc gggataagtc cgcgggaggc    25560
ggagccgatg gatccgcagc accggctgct gctggagacg cgctggagcg ccctggagga    25620
cgcgggggtg cgtccagagc acctgaaggg ctcggacacg ggagtgttcg tgggcgtggc    25680
gccgagcgaa tacgcgagct accgaggaaa gagcgcgaac gaagatgcgt atgcgctgac    25740
agggacggcg ctgagctttg ctgcgggacg ggtggcctac cacctcgggc tgcaaggccc    25800
tgcggtgtcg accgacacgg cctgcagctc gtcgctggta gcggtgcacc tggcgtgcga    25860
cgcgctgcgc cggggcgatt gcgaggtggc gctggcggca ggtgtgcagg tgctggcgaa    25920
cccggcgggg tttgtgctgc tgtcgcgcac gcgcgcgttg tcgccggacg ggcggtgcaa    25980
ggcgttctcg caggcggcgg acggttatgg ccgtggcgag ggagtcgggg tgctggtgct    26040
gatgcggctg tccgaggcgc agcagcaggg gaagcgggtg ctgggtgtgg tgcgcggcac    26100
ggcggtcaat caggacggcg cgagcagcgg gatcacggcg ccgaacggca cggcgcagca    26160
gaaggtggtg cgcgcggcgc tgcggaacgc ggggctggag ccggcgagca tcgatgtggt    26220
ggagtgccac ggtacgggca cgtcgctggg cgacccgatc gaggtgcagg cgctcggcgc    26280
ggtgtacggg caaggtcggg atatggctcg tccgctgcag ctgggcgcgg tcaagagcaa    26340
```

-continued

```
tatcggtcat ctcgagtccg ccgcgggcat cgcagggdtg tgcaagatcc tggcggcgtt   26400
ccgttacgag tcgctgccgg cgacgctgca cagctcgccg cgcaatcccc gcatcccgtg   26460
ggagaacctg ccggtgcagg tggtcgatcg cctgaccccc tggcctcggc gcgcagaggg   26520 cccccgcgc cgtgccggcg tgtcgtcgtt cgggatcagc gggacgaacg cgcatgtcat   26580
cctcgaagaa gcgccggccg aggcgcggcg cgagcctgtc gaggcgaggc ggcgcctgcg   26640
ctattgccgc tggtgctgtc gggtcgagac gaggccgcgg tgaatgcgca ggcggggcgg   26700
tgggcgaagt ggctggaaga gcacggggag gtggggtggt cggacgtggt gcgcacggcg   26760
gcgctgcacc ggacgcactt cgagtcgcgg gcgtcggtgc ttgcggcgag cgctgcggga   26820
gctgtggagg gtcttcgcgc gctgtcgtcg gggcggccgg atgcggcggt ggtgagcggg   26880
acggcgaagc gaggcgggaa gcttgcggtg ctgttcacgg ggcagggcag ccagcggctc   26940
gggatgggga agaggctta cgaagtgtac cccgtgttcc gtgcggcgtt cgacgaggtg   27000
tgcgaggcgc tggacgcgca tctcgaccgt ggggttgagag aggtggtgtt cgcggccgcg   27060
ggcagcgagg aaggagcgca gctggagcgg acggagtaca cgcagcccgg gctgtttgcg   27120
ctggaagtgg cgctgtaccg tcagtgggag tcgtgggggc tgaagcccgc tgcgctkctg   27180
gggcactcga taggagagct gagcgctgcg cacgtggcgg gtgtgctgag ccttgcggac   27240
gcagcgaagc tagtgtgcgc ccgcggtcgg ctgatgcagg ggtgcgaggc cgggggagcg   27300
atggtgtcgg tggaggcctc ggagccggag gtgcagcggg cgctgtcgga ggtcggggcg   27360 cagggcgac tgagcatcgc cgggctgaac gcgccgatgc agacggtgct gagcggggac   27420
gaagcggcgg tgctcgcggt ggcgcgacgg ctggaggcgc agggccggcg cacgcggcgt   27480
ctgcgtgtgt cgcacgcgtt ccacagcgcg cacatggacg ggatgctgga ggagttcggg   27540
aaggtggcgc gggagtgcac gtacgcgcgg ccgcagctgg cggtggtgag cggcgtgacg   27600
ggcgagctcg gtggcgaaga agcgctgatg tcggccgagt actgggtgag gcaggtgcgc   27660
gaggcggtgc gcttcctgga cgggatgcgc acgcttgcgg cggcgggggt gagcacatac   27720
gtcgagtgtg ggccggatgg cgtgctgtgc gcgctggggg cggggtgcct gccggaggga   27780
gccgaggcga cgtttgtggc gagcctgcgg cgagagcagg aggaagagcg cgcgctggcg   27840
acggcggtgg cgacagtgca cgtgcagggg cacgaggtgg actgggccca ggtgctgtcg   27900
ggccgtggcg gccggcccgt ggagctgccg acgtacgcgt tccagcggca gcgctactgg   27960
ctggaagcgc cgaaggcgcg taccgacgtg ggctcggcgg gcttgaggga gtcggggcat   28020
ccgctgctcg gagcggcaac gaagctggcc gacggcgacg gccatctatt cacaggccgg   28080
ctgtcgctgg gcgagcagcc gtggcttcgc gaccatgcgg tgtttggcga ggtggtcttc   28140
ccgggcacgg ggatgctgga cctcgcgctg gcggctgggc gcacggtggg cagcggggcg   28200
ctgtcggagc tcacgatctc cgagccgctg atgctcgcgg aggacgtggc cgtgcggctg   28260
cagctctcgg tcggggcgcc cgacgccgcg gggcggcgtg cgtttgggct gtacagccag   28320
ccggagcagg gaccggggaga tgcccctgg gtgcagcacg cgacgggcgt gttgaccgac   28380
gagaccctcg ccacctccgg cgagctcgat gagctgacga cgtggccagt gccggcgcc   28440 gaggcggtgg acctctccgg gttctacgag cggctgcatg agcgtggact ccgctacggc   28500
ccggccttcc aggggctcgt ggagctgtcg cgtcgagacg cgaccttctt cggccgggtg   28560
gtgttgccca aagacgcgac cgacagcgcc gaggactacg gggtgcatcc ggcgctgatg   28620
gacgccgcgc tgcatacgat ggtcgcagcg tttgcggagg tatcagcgcc ggcgacgtgc   28680
```

```
tgctgcctttctcgtggtcggacgtggcgttgcacgccacggggggcgagcgagctccggg        28740 tgaggctggagctcgcaggaggcagagactcggcacaggcagccgcctcgctgcgcgtta        28800 cagatgccgccggccagccggtggtgagcgtcggtgccctgcatctgcgccgggcgacgg        28860 ccgagcagctgcgggcagcgacgcatgccgaggcgcagcacctgtaccgggtggacttcc        28920 agctcgtgagcctcgtggagcgggctcgaagtggactcgctggtggtgctccgtgcgc        28980 ctgaggggcgagggcgactgggcgaagcgctgggtgtggaggcgatcgcaggcctcgatg        29040 cattgctcgcgcgatcgagcagggaaccgcgattgcctgagcgggtgctggtcgacatga        29100 cggctggcagctcacagcgctcggacatggtgatatcgtcgcacgaggcgacgggacagg        29160 cgctgtcgctgctgcaagcgtggctgtcggagccccggctcgaggggtgagctggtgt        29220 gggtgacgcgagatgcggtcagcgccgctccgggcgacggtgtccaagactggcgcacg        29280 cgccgctgtggggcttgttcgcacggcggaagcgagcaccccgagcgccggctgcgcc        29340 tgatcgacgttgggaccgagcctctggacgccgggctgctggcgcgcgcgctggcgacgg        29400 cgacggagccggagcttgcgctgcgtggcgcgcggcgatggcggcgcgctggtgcgcg        29460 tgccggcggcagcggaagggctcacgccggcgcgcgggctggacccgacggggcacggtcc        29520 tggtgaccggaggaacaggcgagctgggtcaggccgtcgcggagcatctggtgcgcgcac        29580 acggggtgcggcacctcgtgctgacgtcgccgtgggctggaggcgcccggggcccccag        29640 gcttcgtgcaggcgctggagaagctcggtgccgagaccgtgacggtggcggcgtgtgacg        29700 tgtcgaagcgggaggaggtcgcgcgcgtgctggccggcatcgaggccgcacatccgctga        29760 ccgcggtgctgcacctggccggcgtgctcgacgatggcgtcatcaccgcgcagacgcccg        29820 agcgtctctcgcgggtgctggcgccgaaggtgaacggggcgctgcacctgcacgagctga        29880 cagaggatctcgatctctcggccttcgtgctgttctcctcgatgtccgggacgctcggga        29940 cggcgggccagagcaactacgcggcggccaacagcttcctcgacgcgttcgcggcgcatc        30000 gccgcagccgcgggctcgcggcgacgagcctggcgtggggcttctgggcgcaaacgggcg        30060 tgggcatgacagcgcacctggcgcgaggcggagctctcacgtatccagcgcgccggacttg        30120 tgccgatacgggtcgaggagggcctttcgctgctggacgccgcgcttctgcgccccgaag        30180 cgagcctggtgcctgcgcacctcgatcttgcgcagatgcagcggggggctgaggccagcg        30240 gcgagctgccgcgctgcttgcgcgcgctgctgccgccctgggctgcgcaagcgtcatccg        30300 ccacgaggaaggaagcctcggcgctccgcgagccgcctctcggagctgccggaggcggagc        30360 gcctgagctcgctcgtcgagctggttcgggccgaggtggccgcggtgctcgggctgccgc        30420 gcagcgaggccgttgcggtagatcaggtgctgaaggacctagggctagatcgttgatgg        30480 cggtggagctgcgcagtcggctcagcgcccgagccgagatccccctcccgcgacgctgg        30540 tgttcgactacccgacgccgcgcgccgtcgcagagctgctcctgagacagctttctcga        30600 agcagcaggtgacggcagcgcgggcgcgtcgccggacgaaggaagacgagcgatcgcga        30660 tcgtatcgatggcgtgccggttgccaggggcgtggcgacgccggaagactactggcgtc        30720 cctggcggaagggaaggacgccatcgagcgctttccctcccgttatgacgcgttctctgt        30780 ttatgaccccgatccggaggcggtgggcaagagctacgtgcgcgagggtgattcctgcg        30840 ggatatcgatgtcttcgacgcaggcttcttcgggatctcgccgcgcgaggcgcaggcgat        30900 ggatccccagcagcggctggtgctggagacggcgtgggagcgctggagcgagccggcgt        30960 gcggccctcgatgctgagcgagagcgccaccggggtatacctgggctggatgggctcgga        31020 ctacggtgctcttctcggcaatgacctcgccgcgctggacgggtaccaggtacggggag        31080
```

```
cgcggcgagc gtgctttcag gccgggtggc ttacgtgctg gggcttcagg gcccagcgat   31140
cacggtggac acggcgtgct cgtcgtcgct ggtgtcgctg cacctggcgt gcacggcgct   31200
gcgccagggc gaatgcgacc tggcgctgac cggcggggtg atggtgatga ccacgcccgc   31260
gggattcgtt gagttcagtc gtgcccgggg gcttgcgcga gacggtcggt gcaagagctt   31320
ctctgcccag gctgacggcg tcatctggtc cgaaggtgtg cgggatgctgt tgctgaagcg   31380 gctgtctgac gcgcggcgcg acggcgaccg tgtgctgggg gtgatccgtg gctctgcggt   31440
gaaccaggac ggtcgcagcc aggtctgacg gcgccgaac ggccctgccc agcagcgggt   31500
gatccggcag gcgctgtcgt cgtgtggtct gtcgcccgag gacatcgacg cggtggaggc   31560
gcatgggacg ggtacgagcc tcggagaccg gatcgaggcc ggagcgctgg cggaggtgtt   31620
tggaccggag cgtagccccg agcgtccgct gtacctgggg tcgtcgaagt cgaacctggg   31680
acatgcgcag gcggccgcgg gtgtggcggg cgtgatcaag atggtgctgg cgctgcagca   31740
cgaggtgctg ccgaagacgc tgcatgcgga gcagccgagc ccgcacatcg cgtgggaggg   31800
gagcgggctg tcattgctgc aagaggcgcg tccgtggcgg cgcaacggcc gggtccgtcg   31860
tgccggcgtg tcgtcgttcg ggatcagcgg gacgaacgcg catatcatcc tcgaagaagc   31920
gccggccgag gcgcggcgcg agcctgtcga ggccgaggcg gcgcctgcgc tattgccgct   31980
ggtgctgtcg ggtcgagacg aggcctcggt ggcggcgcag gcggggcggt gggcgaagtg   32040
gctggaagag cacggggagg tggggtggtc ggacgtggtg cgcacggcgg cgctgcaccg   32100
gacgcacttc gagtcgcggg cgtcgatgct tgcggcgagc gtgtccgagg tggtggaggt   32160
gctgcgggcg ctgtcagagg gtcgcggcca ccgggcggtg tccgtgggca cggcgcgtgc   32220
gcgaggcaag gtggtgttcg tgttccccgg ccaagggagc cagtggccgg ggatgggccg   32280
ggcgctgctg gagcagagcg cagcgttcgc ggaggcggtg caggcgtgcg atgaggcgct   32340
gcggccgtgg acgggctggt ctgtgctgtc ggtgctgcgc ggagatggcg gggaggagca   32400
gccgtcgctg gagcgggtgg acgtggtgca gcctgcgctg ttcgcgatgt gcgtgggtct   32460
ggccgcggcg tggcggtcgc tggggctgga gcctgcggcg gtggtgggcc acagccaggg   32520
cgaggtgtcg gcggcggtgg tgtgcggggc gctgtcgctt gcggagggag cgcgggtagt   32580
ggcgctgcgc agccaggcgg tgcggcagca gtcggggatg ggggcgatga tgctggtcga   32640
gcagccggtg tcggaggtgc aggagcgcat cgcgccgtac ggggaggcgc ttgcgatagc   32700
ggcggtgaac acgtcgaact cgacggtggt gtcgggtgac gtggaggcgg tggacgggct   32760
gatggtgggc tgacggcaga aggtgtgttc tgccggaagg tgaacgtcga ctacgcgtcg   32820
cacagcgcgc acatggatgc gctgctgccc gagctaggag cgaagctgtc gtcgctcagg   32880
ccgaaggcga cgcagctgcc gttttactcg acggtgacag gagaggtgtc gcggggcgag   32940
gcgctggacg cgagtactg tgccgcaac cttcggcaga cggtgcgcct ggaccgagcg   33000
ctgtcgaagc tgctggagga cgggcacggt gtgttcgtgg aggtgagcgc gcacccggtg   33060
ctggcgatgc cgctgacgac ggcgtgcggg gaggcgcagg ggtggtggt ggggagcttg   33120 cagcgcgacg aaggtgggtt gtcgcagctg tacaggacgc tggggcagct gcacgtgcag   33180
gggcacgagg tggactgggc acgggtgctg tcgggccatg tggtcgtgc cgtggagctg   33240 ccgacgtacg cgttccagcg gcagcgctac tggctggata tctcgaaggc gcgtagcgac   33300
gtgagctcgg cggggctgaa ggcggccgcc catccgctgc tggagcagc aacgaagctg   33360 gctgagggcg atggccatct gttcaccggc cggctgtcgc tgggcgagca tgcgtggctc   33420
```

```
cgcgaccatg aggtgtttgg taacttggtg ttcccccggg cgcggggrat g

-continued

```
<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" represents A, T, C or G

<400> SEQUENCE: 7
rtgsgcrttv gtnccrct                                                18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" represents A, T, C or G

<400> SEQUENCE: 8
gacacvgcnt gytcbtcv                                                18
```